United States Patent
Hattori et al.

(10) Patent No.: US 7,226,965 B2
(45) Date of Patent: Jun. 5, 2007

(54) POLYMERIC-TYPE ELECTRIC RESISTANCE CONTROL AGENT AND POLYMER COMPOSITION CONTAINING THE SAME

(75) Inventors: Takayuki Hattori, Hyogo (JP); Katsumi Terakawa, Hyogo (JP); Tetsuo Mizoguchi, Hyogo (JP); Kenichi Uesaka, Hyogo (JP); Toshiaki Sakaki, Hyogo (JP); Hiromasa Okubo, Hyogo (JP); Noriaki Fujihana, Osaka (JP); Yoshiharu Tatsukami, Osaka (JP)

(73) Assignees: Sumitomo Rubber Industries, Ltd., Kobe-shi (JP); Sanko Chemical Industry Co., Ltd., Osaka (JP)

( * ) Notice: Subject to any disclaimer, the term of this patent is extended or adjusted under 35 U.S.C. 154(b) by 59 days.

(21) Appl. No.: 10/756,414

(22) Filed: Jan. 14, 2004

(65) Prior Publication Data

US 2004/0220301 A1    Nov. 4, 2004

(30) Foreign Application Priority Data

Jan. 15, 2003  (JP) ............................. 2003-007083
Feb. 17, 2003  (JP) ............................. 2003-038168

(51) Int. Cl.
*C08K 5/00*     (2006.01)
*C08K 5/42*     (2006.01)
*C08L 21/00*    (2006.01)

(52) U.S. Cl. ................... 524/157; 524/159; 524/161; 524/164; 524/166; 524/462; 524/500; 524/505; 524/612; 525/90; 525/240

(58) Field of Classification Search ............... 524/157, 524/159, 161, 164, 166, 462, 500, 505, 612; 525/90, 240
See application file for complete search history.

(56) References Cited

U.S. PATENT DOCUMENTS

| 5,604,284 | A | | 2/1997 | Ueda et al. |
| 5,652,326 | A | | 7/1997 | Ueda et al. |
| 5,814,688 | A | * | 9/1998 | Hilti et al. ...................... 524/9 |
| 5,886,098 | A | | 3/1999 | Ueda et al. |
| 5,955,517 | A | | 9/1999 | Hilti et al. |
| 5,959,015 | A | * | 9/1999 | Helms et al. ............... 524/394 |
| 6,194,497 | B1 | * | 2/2001 | Willems et al. ............. 524/165 |

FOREIGN PATENT DOCUMENTS

| EP | 0 789 049 A1 | 8/1997 |
| EP | 0 897 950 A2 | 2/1999 |
| EP | 1 376 617 A2 | 1/2004 |
| JP | 64-9258 A | 1/1989 |
| JP | 1-178554 A | 7/1989 |
| JP | 01178554 A * | 7/1989 |
| JP | 2-255852 A | 10/1990 |
| JP | 3-135784 B2 | 6/1991 |
| JP | 8-34929 A | 2/1996 |
| JP | 8-169985 A | 7/1996 |
| JP | 9-132677 A | 5/1997 |
| JP | 9-227717 A | 9/1997 |
| JP | 9-227743 A | 9/1997 |
| JP | 10-182988 A | 7/1998 |
| WO | WO 99/67331 A1 | 12/1999 |

* cited by examiner

Primary Examiner—Kelechi C. Egwim
(74) Attorney, Agent, or Firm—Birch, Stewart, Kolasch & Birch, LLP

(57) ABSTRACT

The present invention provides a polymeric-type antistatic agent containing a polymer composition consisting of a polymeric-type antistatic agent containing a resin or/and an elastomer as a main component thereof; or/and a thermoplastic resin having a polar group or/and an elastomer having the polar group. At least one kind of an anion-containing salt, having a fluoro group and a sulfonyl group, is added to the polymer composition without intermediary of a medium consisting of a low-molecular-weight polyether-containing compound or a low-molecular-weight polar compound whose number-average molecular weight is not more than 5000. The present invention also provides a composition, for a conductive roller or the like, containing polymer components and the polymeric-type antistatic agent dispersed in the polymer components.

24 Claims, 8 Drawing Sheets

POLYMERIC-TYPE ELECTRIC RESISTANCE CONTROL AGENT AND POLYMER COMPOSITION CONTAINING THE SAME

This Nonprovisional application claims priority under 35 U.S.C. § 119(a) on Patent Application No(s). 2003-007083 filed in Japan on Jan. 15, 2003, and 2003-038168 filed in Japan on Feb. 17, 2003, the entire contents of which are hereby incorporated by reference.

BACKGROUND OF THE INVENTION

Field of the Invention

The present invention relates to a polymeric-type antistatic agent, an antistatic (conductive) polymer composition containing the polymeric-type antistatic agent, a method of manufacturing the polymeric-type antistatic agent and the antistatic (conductive) polymer composition, and products formed from the antistatic polymer composition. More particularly, the present invention relates to the polymeric-type antistatic agent that does not deteriorate properties of the composition, nor generates breeding or blooming, nor stains a photosensitive member owing to the migration of an additive contained therein, and is capable of continuously displaying sufficient charge prevention performance even at a low temperature and humidity, the antistatic polymer composition, the method of manufacturing the polymeric-type antistatic agent and the antistatic (conductive) polymer composition, and antistatic products formed from the antistatic polymer composition.

In recent years, it has become important to impart antistatic properties to polymer materials such as a thermoplastic resin and a thermoplastic elastomer. To this end, a method (first method) of applying a charge prevention agent such as a surface active agent to the surface of a molded product is known. In addition, a method (second method) of kneading the charge prevention agent into the polymer material is also known.

The first method has a disadvantage that the antistatic properties deteriorates greatly with a long elapse of time. Thus it is difficult to use the polymer material treated with the charge prevention agent into conductive (antistatic) members as a durable antistatic resin or elastomer. In addition, the first method has another disadvantage that the charge prevention agent migrates to other members of an image-forming apparatus or the like and stains them.

According to the conventional art, the charge prevention agent has a low degree of compatibility with the polymer material. Thus the second method has a disadvantage of deteriorating the properties thereof greatly. Unless a large amount of the charge prevention agent is added to polymer material, polymer material is incapable of obtaining a sufficiently low electric resistance. That is, the problem of the second method is that the addition of the charge prevention agent to polymer material deteriorates the properties thereof and makes the manufacturing cost high. Further in dependence on the kind of the charge prevention agent, polymer material has a high electric resistance at a low temperature and humidity and cannot display sufficient charge prevention performance. In addition, some of the charge prevention agents used in the method (second method) of kneading the charge prevention agent into polymer material bleeds or blooms on the surface of a product formed from polymer material to thereby obtain a sufficiently low electric resistance. These charge prevention agents migrate to the photosensitive member and stain it. In addition, it takes as long as one to three days until the charge prevention effect can be obtained from the time when polymer material is molded.

In addition to the above-described methods, a method of kneading carbon black or carbon fibers to resin or rubber is proposed. This method allows charge prevention performance to be effective and continue for a long time and does not cause bleeding or blooming, but has a problem that it is impossible to color the resin or the rubber as desired. Moreover, the addition of the carbon black thickens the resin or the rubber, which leads to poor moldability in injection molding and extrusion molding and the increase of the hardness, deterioration of tensile elongation, tear strength, and compression set.

In addition to carbon, in a known method, conductive fillers such as metal oxides are added to a polymer material. In the method of using the carbon black and the method of using the metal oxide, it is necessary to use a large amount thereof. Consequently the properties of the polymer material deteriorate and the material cost becomes high.

In the case where the conductivity-imparting agents (electroconductive fillers) such as the carbon black, the carbon fibers or the metal oxide is used, the electric resistance of the polymer composition changes rapidly with a slight change of an addition amount of the conductivity-imparting agents. Thus it is very difficult to control the electric resistance of the polymer composition. In addition, because it is difficult to disperse the conductivity-imparting agents uniformly in the polymer composition, there occurs a problem of large variations of the electric resistance in a product formed from the polymer composition and among products.

In the case where a product formed from the polymer composition is used as a conductive roller and a conductive belt for use in an image-forming apparatus such as a copying apparatus, a printer, a facsimile, and the like, the electric resistance of a conductive polymer composition containing the electroconductive filler depends on a voltage applied thereto and is not constant. In the case where the carbon black is used as the conductive filler, the variation of the electric resistance is conspicuous. Thus it is difficult to accomplish mechanical control of an image-forming process including charging, development, transfer, and fixing, which may lead to the increase of the manufacturing cost.

To achieve the above-described object and meet demands for development of an antistatic material having performance of reducing the electric resistance and colorability, various proposals have been made. For example, in Japanese Patent Application Laid-Open Nos. 64-9258 and 2-255852, there are disclosed the vinyl chloride resinous compositions, having charge prevention performance, containing lithium perchlorate or quaternary ammonium salt of perchloric acid. In Japanese Patent Application Laid-Open No. 10-182988, there is disclosed the polymer composition, having charge prevention performance, containing the ester group-containing plasticizer having the specific structure and an alkali metal salt or an alkali earth metal salt added thereto.

In Japanese Patent Application Laid-Open No. 9-227743, there is disclosed the transparent conductive resinous composition containing vinyl chloride resin, a plasticizer, and lithium-bis (trifluoromethanesulfonyl) imide.

In Japanese Registered Patent No. 3135784, there are proposed the resinous compositions, having a high degree of permanent charge prevention performance, consisting of the vinyl polymer having polyether ester amide and a sulfonic group (sulfonate); the block polymer having the polyolefin part and the aromatic vinyl-based polymeric part; the polymer composed of styrene used as the unit. In Japanese Patent Application Laid-Open No. 9-227717, there is disclosed the polymer consisting of a polar adsorptive organic material or a polar adsorptive inorganic material, and a polar charge prevention agent.

However, in the compositions disclosed in Japanese Patent Application Laid-Open Nos. 64-9258, 2-255852, 10-182988, and 9-227743, the plasticizer bleeds on the surface of a product and stains it. When metals are packed with a film or a sheet formed from the antistatic composition containing the chlorine-containing salt such as lithium perchlorate, a metal surface is corroded, rusted or stained. Similarly, there is a possibility that a metal shaft and a driving shaft are corroded at a high humidity, when conductive products such as a conductive roller, a conductive belt, and the like, for use in a copying apparatus, a printer, and the like, are formed from the antistatic composition containing the chlorine-containing salt. Moreover, the compositions disclosed in the above-described publications are dispersed comparatively uniformly in resins such as vinyl chloride, polyamide, polyester and an elastomer, thus obtaining sufficient antistatic properties. However, the compositions disclosed in these publications are liable to generate bleeding for resins such as polyolefin, polystyrene, and the like and elastomers having these structures and incapable of obtaining a low electric resistance.

The resinous composition disclosed in Japanese Registered Patent No. 3135784 and the polymer disclosed in Japanese Patent Application Laid-Open No. 9-227717 are preferable in that they do not stain a photosensitive member by the migration of an additive contained therein nor generate bleeding, but have room for improvement of the performance of reducing the electric resistance thereof. When a large amount of the conductive filler is used to increase the performance of reducing the electric resistance of the polymer material, the dynamic properties thereof such as the compression set and the hardness deteriorate and the material cost becomes high. It is necessary to improve the performance of securing the antistatic properties of resin such as polyolefin, polystyrene, and the like and the elastomers having these structures.

From the above-described view point, as a recent tendency, in the copying machine, the printer and the like capable of forming high-quality images by using digital image processing technique and color image processing technique, an ionic-conductive polymer composition such as epichlorohydrin rubber is used rather than a polymer composition containing the electroconductive filler.

However, as described above, the conventional ionic-conductive agent is incapable of reducing the electric resistance of the polymer composition efficiently and generates bleeding when it is used in a large amount. Some ionic-conductive agents are unstable at a high temperature. Thus they cannot be applied to resin or a thermoplastic elastomer required to be processed at a high temperature. In this case, it is necessary to take a explosion-proof measure. Thus the manufacturing cost becomes high.

Chlorine is contained in the epichlorohydrin rubber which is used for the conductive roller and the conductive belt for use in the copying apparatus, the printer, and the like, a fuel hose, an oil-resistant hose, and the like. Thus in recent years, to exclude the possibility of generation of dioxin or the like and prevent accidents from occurring owing to static electricity caused by the use of a charge prevention agent for the epichlorohydrin rubber, there is a demand for replacing the epichlorohydrin rubber with a material not containing chlorine and having a electric resistance almost equal to that of the epichlorohydrin rubber.

When a material such as a polymer, having a cyano group, which does not contain chlorine is used instead of the epichlorohydrin rubber, the electric resistance of the polymer rises. Thus the polymer cannot be used as it stands.

That is, the cyano group (—CN) of acrylonitrile-butadiene rubbers having the cyano group is capable of stabilizing ions to some extent. Thus the acrylonitrile-butadiene rubber has a volume resistivity of $10^{9.5}$ to $10^{11.0}$ ($\Omega \cdot cm$). But it is difficult to reduce the electric resistance of the polymer composition sufficiently by using only the acrylonitrile-butadiene rubber for the polymer composition to prevent it from being statically charged.

In recent years, there is a demand for further reduction of the electric resistance of rollers or belts which rotate at a high speed and repeat contact and non-contact with other members, namely, the rollers or belts which are used in severe conditions to prevent generation of static electricity. In particular, there is a demand for further reduction of the electric resistance (volume resistivity in particular) of these conductive rollers and conductive belts for use in a color copying machine, a color printer, and the like to save energy. These conductive rollers and conductive belts are also demanded to have a low compression set, a uniform electric resistance, and a low degree of dependence on environment in the electric resistance thereof.

Industrial products such as a fuel hose, an oil-resistant hose, and the like conveying gas, fuel, organic solvent, and a shoe sole, and the like are also demanded to be safe against a electric charge-caused ignition. Therefore there is a tendency of making the electric resistance of the polymer composition lower than that of the NBR (acrylonitrile-butadiene rubber) to thereby solve the problem caused by static electricity. It is important to impart charge prevention performance to rubber products which may give obstructions to electrical appliances such as a computer to prevent an electric charge from accumulating therein. That is, it is important to reduce the electric resistance the polymer composition.

To reduce the electric resistance of the polymer having the cyano group, the use of a surface active agent, a low-molecular-weight ionic conductivity-imparting additive such as a low-molecular-weight ionic conductivity-imparting additive containing polyether, an ionic-conductive plasticizer, and the like is proposed.

In Japanese Patent Application Laid-Open No. 9-132677, there is disclosed a rubber composition containing quaternary ammonium salt of perchloric acid or/and aliphatic diester of monocarboxylic acid of polyalkylene glycol added to acrylonitrile-butadiene rubber (NBR) or hydrogenated nitrile rubber (HNBR). In the disclosure, imparting conductivity to the rubber composition to secure charge prevention performance are proposed. Facilitating the control of the electric resistance thereof is also proposed.

In the above-described Japanese Patent Application Laid-Open No. 10-182988, there is disclosed the polymer composition, having charge prevention performance, which contains lithium perchlorate or barium perchlorate mixed with the specific low-molecular-weight compound having the polyether structure to reduce the electric resistance thereof.

In Japanese Patent Application Laid-Open No. 8-34929, there is disclosed the polymeric solid electrolyte obtained by dipping the crosslinked mixture of NBR latex and SBR latex in an electrolyte obtained by dissolving various metal salts in the low-molecular-weight medium such as a solvent of the mixture of propylene carbonate and 2-methyltetrahydrofuran.

However, in the rubber composition disclosed in Japanese Patent Application Laid-Open No. 9-132677, the reduction of the compression set accomplished by the use of the quaternary ammonium salt of perchloric acid is insufficient. That is, chlorine contained in the quaternary ammonium salt makes a secondary reaction, which deteriorates the compression set of the rubber composition. Accordingly the conductive roller or the conductive belt formed from the rubber composition has a problem in its durability and dimensional stability. Because the rubber composition contains chlorine, there is a possibility that dioxin or the like is generated. Further a sufficient reduction of the electric resistance of the rubber composition can be obtained by the use of a considerably large amount, namely, 20 parts by weight of the quaternary ammonium salt of perchloric acid and a considerably large amount, namely, 60 parts by weight of the aliphatic diester of monocarboxylic acid of polyalkylene glycol. Thus the rubber composition cannot be put to practical use because the material cost is high, the hardness thereof changes, stains a photosensitive member owing to the migration of an additive or the like contained therein, and generates bleeding.

The polymer composition having charge prevention performance disclosed in Japanese Patent Application Laid-Open No. 10-182988 is capable of reducing the electric resistance thereof to some extent, but has a high degree of dependence on environment. Further because the polymer composition contains the metal salt of the perchlorate, the compression set of the polymer composition deteriorates. Moreover because the low-molecular-weight compound used as the medium is not fixed to the polymer, it generates bleeding and stains the photosensitive member owing to the migration thereof.

The polymeric solid electrolyte disclosed in Japanese Patent Application Laid-Open No. 8-34929 is capable of reducing the electric resistance thereof to some extent, but the low-molecular-weight solvent used to disperse the salt adversely affects other properties of the polymeric solid electrolyte. That is, the hardness and strength of the polymeric solid electrolyte become lower. Further the polymeric solid electrolyte generates bleeding and stains the photosensitive member owing to the migration thereof.

SUMMARY OF THE INVENTION

The present invention has been made in view of the above-described problems. Therefore it is an object of the present invention to provide a polymeric-type antistatic agent and a antistatic polymer composition which keep excellent antistatic properties for a long time, do not generate bleeding or blooming, nor stains a photosensitive member or the like owing to the migration of an additive contained therein, nor deteriorate the properties thereof; a method of manufacturing the polymeric-type antistatic agent and the antistatic polymer composition; and products formed from the antistatic polymer composition. Particularly, the present invention is intended to impart sufficient antistatic properties to a resin such as polyolefin and polystyrene having a low polarity and to an elastomer having these structures without staining the photosensitive member or the like owing to the migration of the additive, deteriorating the properties thereof, and increasing the manufacturing cost much, although the conventional art has difficulty in doing so.

It is still anther object of the present invention to provide a conductive polymer composition whose electric resistance depends to a low extent on environment by controlling the electric resistance thereof in a wide range and by reducing the volume resistivity thereof in a normal condition and at a low temperature and humidity at which static electricity is apt to be generated.

It is still anther object of the present invention to provide a high-performance conductive roller and a high-performance conductive belt whose electric resistance depends to a low extent on environment by reducing the volume resistivity thereof in the normal condition and at the low temperature and humidity at which static electricity is apt to be generated; and industrial products that display sufficient charge prevention function sufficiently even at the low temperature and humidity.

To achieve the object, as the first invention, the present invention provides a polymeric-type antistatic agent including:

a polymer composition containing a polymeric-type charge prevention agent containing a resin or/and an elastomer as a main component thereof; or/and a thermoplastic resin having a polar group or/and an elastomer having the polar group; and an anion-containing salt, having a fluoro group and a sulfonyl group, which is added dispersedly in the polymer composition without intermediary of a medium consisting of a low-molecular-weight polyether-containing compound or low-molecular-weight polar compound whose number-average molecular weight is not more than 5000.

The present inventors have formed a large number of charge prevention agents and additives and energetically studied various components to be mixed with one another and mixing ratios by conducting experiments. As a result, they have found that it is possible to prevent the polymeric-type antistatic agent from generating bleeding and blooming and staining a photosensitive member and obtain excellent antistatic properties without deteriorating the properties thereof such as the compression set, hardness, and the like and realize continuous charge prevention performance by adding the anion-containing salt having the fluoro group and the sulfonyl group to the polymer composition without the intermediary of the medium and uniformly dispersing the anion-containing salt having the fluoro group and the sulfonyl group in the polymer composition which contains the polymeric-type charge prevention agent or/and the thermoplastic resin having the polar group or/and the elastomer having the polar group and which contains the resin or/and the elastomer as the main component thereof.

The polymer composition contains containing the polymeric-type charge prevention agent containing the resin or/and the elastomer as its main component or/and the thermoplastic resin having the polar group or/and the elastomer having the polar group. Therefore ions generated from the anion-containing salt having the fluoro group and the sulfonyl group can be stabilized. Consequently it is possible to uniformly disperse the salt in the polymer composition. The resin or/and the elastomer should be contained in the polymer composition at favorably not less than 80 wt % and more favorably not less than 90 wt % of the entire weight of the polymer composition. Various rubbers and thermoplastic elastomers can be used as the elastomer.

As the anion-containing salt having the fluoro group and the sulfonyl group, a salt having at least one kind of an anion selected from among chemical formulas 1 through 3 shown below is preferable.

chemical formula 1

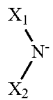

chemical formula 2

chemical formula 3

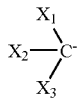

where $X_1$, $X_2$, and $X_3$ denote functional groups containing C, —F, and —$SO_2$— and having one to eight carbon atoms.

In the anion of the above-described chemical formulas 1 through 3, each of $X_1$, $X_2$, and $X_3$ indicate a functional group including C, —F, —$SO_2$— and having 1 to 8 carbon atoms.

In the above-described anion-containing salt, anions are stable because the electric charge are not localized by a strong electron attraction effect provided by the fluoro group (—F) and the sulfonyl group (—$SO_2$—). Thus the salt shows a high degree of dissociation in the polymer composition and is capable of realizing a very high ionic conductance. The anion-containing salt is compatible with the polymer composition of claim 1. Therefore it is possible to reduce the electric resistance of the polymeric-type antistatic agent greatly by adding a small amount of the anion-containing salt to the polymer composition. In this case, other properties of the polymeric-type antistatic agent deteriorate very little. Thus it is possible to obtain a target low electric resistance without deteriorating the other properties of the polymeric-type antistatic agent by adjusting the amount of the salt and the kind of the salt. Further it is possible to provide the polymer composition with a very low volume resistivity than that obtained by a composition containing acrylonitrile-butadiene rubber or the like and alter the volume resistivity thereof as desired in a wide range of $10^7$ to $10^{13}$ ($\Omega \cdot cm$) without deteriorating the other properties thereof. Because the anion-containing salt does not cause the polymer composition to be black unlike carbon black, the use of the anion-containing salt allows preferable colorability to be obtained.

The number of carbon atoms of the functional group shown by the above-described chemical formulas 1, 2, and 3 is one to eight. To obtain a higher degree of dissociation, the number of carbon atoms thereof is favorably one to four and more favorably one to two.

As the functional group $X_1$ and $X_2$, groups such as R—$SO_2$— (R indicates hydrocarbon group having one to eight carbon atoms replaced with fluorine atom) are listed.

As the hydrocarbon group having one to eight carbon atoms, it is possible to list the following groups: alkyl groups such as methyl group, ethyl group, n-propyl group, isopropyl group, n-butyl group, isobutyl group, tert-butyl group, n-pentyl group, isopentyl group, tert-pentyl group, n-hexyl group, 1,1-dimethylpropyl group; a alkenyl group such as vinyl group, aryl group, 1-propenyl group, isopropenyl group, 2-butenyl group, 1,3-butadienyl group, and pentenyl group; alkynyl group such as ethynyl group, 2-propynil group, 1-butynil group, and 2-butynil group. The number of fluorine atom serving as the substituting group and the substituting position are not limited to specific ones.

In the anion of the above-described chemical formulas 1, 2, and 3, it is preferable that $X_1$ is $C_{n1}H_{m1}F_{(2n1-m1+1)}$—$SO_2$—, that $X_2$ is $C_{n2}H_{m2}(2n2-m2+1)$—$SO_2$—, and that $X_3$ is $C_{n3}H_{m3}F_{(2n3-m3+1)}$ (n1, n2, and n3 may be identical to each other or different from each other and are integers not less than 0, and m1, m2 and m3 may be identical to each other or different from each other and are integers not less than 0) in terms of stability, cost, and handling properties.

Of the anion-containing salt having the fluoro group and the sulfonyl group and the anion-containing salts shown by the chemical formulas 1 through 3, lithium-bis (trifluoromethanesulfonyl) imide $(CF_3SO_2)_2NLi$), potassium-bis (trifluoromethanesulfonyl) imide $(CF_3SO_2)_2NK$), and lithium trifluorosulfonic acid $(CF_3SO_3Li)$ are preferable. These salts are stable at high temperatures. Therefore different from perchlorates conventionally used as an ionic-conductive agent, it is unnecessary to take an explosion-proof measure. Further these salts are superior in that they hardly deteriorate other properties of the polymeric-type antistatic agent and suppress the rise of the electric resistance thereof at a low temperature and humidity. In this respect, these salts are capable of reducing the manufacturing cost, securing safety, and functioning as a antistatic agent or an electric conduction-imparting agent to a high extent.

The following salts are preferable as the anion-containing salt shown by the chemical formulas 1 through 3: $(C_2F_5SO_2)_2$ NLi, $(C_4F_9SO_2)$ $(CF_3SO_2)$ NLi, $(FSO_2C_6F_4)$ $(CF_3SO_2)$ NLi, $(C_8F_{17}SO_2)$ $(CF_3SO_2)$ NLi, $(CF_3CH_2OSO_2)_2$ NLi, $(CF_3CF_2CH_2OSO_2)_2NLi$, $(HCF_2CF_2CH_2OSO_2)_2NLi$, $((CF_3)_2CHOSO_2)_2NLi$, $(CF_3)_2SO_2)_2CLi$, $(CF_3CH_2OSO_2)_3$ CLi, $C_4F_9SO_3Li$, $(C_2F_5SO_2)_2$ NK, $(C_4F_9SO_2)$ $(CF_3SO_2)$ NK, $(FSO_2C_6F_4)$ $(CF_3SO_2)$ NK, $(C_8F_{17}SO_2)$ $(CF_3SO_2)NK$, $((CF_3)_2CHOSO_2)_2NK$, $(CF_3CF_2CH_2OSO_2)_2NK$, $(HCF_2CF_2CH_2OSO_2)_2NK$, $((CF_3)_2CHOSO_2)_2NK$, $(CF_3SO_2)_2CK$, $(CF_3CH_2OSO_2)_3$ CK, and $C_4F_9SO_3K$.

The anion-containing salt having the fluoro group and the sulfonyl group and the anion-containing salt shown by the chemical formulas 1 through 3 can be used singly or in combination respectively.

It is preferable that the cation making a pair with the anion having the fluoro group and the sulfonyl group and with the anion shown by the chemical formulas 1 through 3 to form the salt is the cation of any one of alkali metals, group 2A metals, transition metals, and amphoteric metals. The alkali metals are more favorable than the other metals, because the alkali metals have smaller ionization energy and thus form stable cations readily.

For the above-described reason, as the anion-containing salt having the fluoro group and the sulfonyl group, it is optimum to select at least one salt from among the group of an alkali metal salt of bis (trifluoromethanesulfonyl) imide, an alkali metal salt of tris (trifluoromethanesulfonyl) methide, and an alkali metal salt of trifluoromethanesulfonic acid. Lithium-bis (trifluoromethanesulfonyl) imide is particularly preferable.

In addition to cations of metal, it is possible to use cations shown by the following chemical formulas 4 and 5:

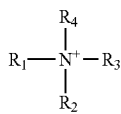

Chemical formula 4 where $R_1$ through $R_4$ indicate alkyl group, having one to 20 carbon atoms, which may have substituting group. $R_1$ and $R_4$ may be identical or different from each other.

Chemical formula 5 where $R_5$ and $R_6$ indicate alkyl group, having one to 20 carbon atoms, which may have substituting group. $R_5$ and $R_6$ may be identical or different from each other.

As the alkyl group having one to 20 carbon atoms in "the alkyl group, having one to 20 carbon atoms, which may have substituting group" indicated by $R_1$ to $R_6$, methyl, ethyl, n-propyl, I-propyl, n-butyl, s-butyl, t-butyl, n-heptyl, n-hexyl, n-decil are listed.

As the substituting group, halogen (preferably fluorine, chlorine, bromine), oxo group, alkylene oxide group, alkanol group, (preferably $C_{1-8}$), alkanol oxy group, (preferably $C_{1-8}$), alkanolamino group, (preferably $C_{1-8}$), carboxyl group, alkoxy carbonyl group, (preferably $C_{2-8}$), haloalkyl carbonyl group (preferably $C_{2-8}$), alkoxy group (preferably $C_{1-8}$), haloalkoxy group (preferably $C_{1-8}$), amino group, alkylamino group (preferably $C_{1-8}$), dialkylamino group (preferably $C_{2-16}$), cyclic amino group, alkylaminocarbonyl group (preferably $C_{2-8}$), carbamoyl group, hydroxyl group, nitro group, cyano group, mercapto group, alkylthio group (preferably $C_{1-8}$), alkylsulfonyloxy group (preferably $C_{1-8}$), alkylsulfonylamino group (preferably $C_{1-8}$), and phenyl group.

As the cation shown by the chemical formula 4, trimethyl-type quaternary ammonium cations is particularly preferable. In the trimethyl-type quaternary ammonium cations, three of $R_1$ through $R_4$ consist of a methyl group and one of $R_1$ through $R_4$ consists of an alkyl group, having 4 to 20 carbon atoms, which may have a substituting group. This is because three methyl groups having strong electron-donating property is capable of stabilizing the positive electric charge of nitrogen atoms. In addition, the alkyl group is capable of improving compatibility of the salt having the cations with the polymer component. In the cations shown by the chemical formula 5, $R_5$ or $R_6$ having a stronger electron-donating property is capable of stabilizing the positive electric charge of nitrogen atoms. Thereby it is possible to increase the degree of stability of the cations and thereby form salts having a higher dissociation degree and superior conductance-imparting performance. Therefore it is preferable that $R_5$ or $R_6$ consists of methyl group or ethyl group because they have preferable electron-donating property.

The above-described specified amount of the anion-containing salt having the fluoro group and the sulfonyl group is contained in the polymer composition without the intermediary of a medium selected from among a group of a low-molecular-weight polyether-containing compound and a low-molecular-weight polar compound each of which is not fixed by crosslinking and has a number-average molecular weight which should be not more than 5000, favorably not more than 7000, more favorably not more than 10000 (weight-average molecular weight should be not more than 10000, favorably not more than 12000, and more favorably not more than 13000).

When the anion-containing salt is added to the entire polymer component without the intermediary of the medium consisting of the low-molecular-weight polyether-containing compound or the low-molecular-weight polar compound not fixed by crosslinking, the medium migrates to a surface of a product such as a photosensitive member formed by the polymer composition and oozes out of the product with a long elapse of time, thereby bleeding or staining the product. Further the addition of the medium to the polymer component causes deterioration of the properties of the polymer composition such as its tensile strength and moduli or increasing its compression set. The above-described low-molecular-weight polyether-containing compound and low-molecular-weight polar compound are liable to migrate and stain the product such as the photosensitive member and deteriorate the compression set of the polymer composition.

On the other hand, when the anion-containing salt is contained in the polymer composition without the intermediary of the above-described the low-molecular-weight medium, the polymeric-type antistatic agent is allowed to have a low electric resistance without causing bleeding, stain of the photosensitive member which occurs owing to migration of the medium and without deteriorating the mechanical properties thereof (deterioration of tensile strength, moduli, increase of compression set). Particularly, it is possible to suppress the rise the electric resistance of the polymer composition to a low extent when an electric field is applied to the polymer composition repeatedly or successively. Therefore the polymeric-type antistatic agent can be suitably used for a conductive roller and a conductive belt for use in an image-forming apparatus such as a copying apparatus, a printer, a facsimile, and the like to which an electric field is applied repeatedly or successively.

As the low-molecular-weight polyether-containing compound, low-molecular-weight (number of molecular weight: normally several hundreds to several thousands) polyethylene glycol, polypropylene glycol, and polyether polyol are listed. As the low-molecular-weight polar compound, low-molecular-weight polyester polyol, adipate, phthalic ester, dimethyl carbonate, and propylene carbonate are listed.

Perchlorates hitherto used may explode when a shock is applied thereto. Thus normally, media such as the above-described low-molecular-weight compounds have been used. However, the salt used in the present invention is safe and compatible with the polymer composition described in claim 1. Thus the salt can be dispersed uniformly in the polymer composition without using the above-described low-molecular-weight compounds. The present inventors have found this fact owing to experiments conducted by them for many years and completed the present invention.

It is preferable that the polymer composition contains at least one kind of a copolymer selected from among the group of a polyoxyalkylene copolymer and a polyether block polyolefin copolymer. Thereby the salt is stabilized to a higher extent by oxygen atoms contained in the ether linkage. Thus the polymeric-type antistatic agent is capable of obtaining a lower electric resistance. Owing to other structures other than the ether linkage of the block, it is possible to secure compatibility of the block with other polymers. Thus it is possible to obtain preferable properties and moldability without deteriorating the properties of the other polymers. It is also preferable that in mixing the polymeric-type antistatic agent containing the polyether block polyolefin copolymer and the anion-containing salt having the fluoro group and the sulfonyl group with other kind of polymers such as a polyolefin thermoplastic elastomer or a styrene thermoplastic elastomer and kneading them at a high temperature and forming a product by injection molding or extrusion molding, a phase structure (percolation structure) advantageous for energization is formed in a matrix resin such as olefin resin to thereby reduce the electric resistance of the polymeric-type antistatic agent to a high extent.

In the present invention, a part of ions generated from the anion-containing salt is single-ionized with an anion adsorbent to stabilize the electric conduction of the polymeric-type antistatic agent and improve its conduction when the polymer composition contains a small amount of the salt.

As the anion adsorbent, it is possible to use known compounds such as synthesized hydrotalcite containing Mg and Al as its main component; Mg—Al-based, Sb-based, and Ca-based inorganic ion exchangers; and polymers or copolymers having an ion seat for fixing anions to chains thereof.

For example, the synthesized hydrotalcite ("Kyoward 2000" and "Kyoward 1000 produced by Kyowa Chemical Indusrty) and an anion-exchangeable ion exchange resin (trade name: Dianon DCA11, produced by Nippon Rensui Inc.) can be used.

In the polymeric-type antistatic agent of the first invention or the antistatic polymer composition, which will be described later, of the second invention using the polymeric-type antistatic agent, it is possible to appropriately use a crosslinking agent, a stabilizer, a filler, a pigment, a blowing agent, lubricant, an anti-fungus agent, an ultraviolet inhibitor, additives such as a charge prevention agent, and a processing aid.

It is preferable that in the polymeric-type antistatic agent of the present invention, not less than 0.01 nor more than 20 parts by weight of the anion-containing salt having the fluoro group and the sulfonyl group is mixed with 100 parts by weight of an entire polymer component contained in the polymeric-type antistatic agent. If the addition amount of the anion-containing salt having the fluoro group and the sulfonyl group is less than 0.01 parts by weight, the intended effect of improving the performance of the polymeric-type antistatic agent can be hardly obtained. On the other hand, if the addition amount is more than 20 parts by weight, the demerit of increasing the material cost is greater than the effect of improving the antistatic properties and the conductivity of the conductive elastomer composition.

The polymeric-type antistatic agent contains the anion-containing salt having the fluoro group and the sulfonyl group at favorably not less than 0.2 nor more than 10 parts by weight and more favorably not less than 0.4 nor more than six parts by weight.

By using a known method, the anion-containing salt having the fluoro group and the sulfonyl group is added to the polymeric-type charge prevention agent whose main component is the resin or/and the elastomer and to the thermoplastic resin having the polar group or/and the elastomer having the polar group without the intermediary of the medium consisting of the polyether-containing compound or the medium consisting of the low-molecular-weight polar compound whose number-average molecular weight is not more than 5000 (weight-average molecular weight is not more than 10000). For example, after the above-described components are dry-blended with a Henshell mixer or a tumbling mixer, they are fused and mixed with each other by mono-axial mixer, a biaxial extruder, a Banbury mixer or a kneader. To prevent deterioration of the polymer, the mixing work can be performed in an atmosphere where inactive gas such as nitrogen gas is present.

The polymeric-type antistatic agent of the first invention or the antistatic polymer composition of the second invention containing the polymeric-type antistatic agent are molded into products having various configurations such as a sheet, a film, a tube, and the like by using conventional molding methods, for example, pressing, injection molding, extrusion molding or calender molding. The polymeric-type antistatic agent or the antistatic polymer composition using the polymeric-type antistatic agent can be used as antistatic resinous compositions for paint by dissolving them in a solvent.

As the second invention, the present invention provides an antistatic (or conductive) polymer composition in which the polymeric-type antistatic agent containing the anion-containing salt having the fluoro group and the sulfonyl group is added to and mixed with one or more substances selected from among a thermoplastic polymer, a thermoplastic elastomer, and an unvulcanized rubber.

More specifically, it is preferable to selectively use any one of the following three methods to produce the antistatic (conductive) polymer composition containing the anion-containing salt (first component) having the fluoro group and the sulfonyl group, the polymer composition (second component) containing the polymeric-type charge prevention agent, the thermoplastic resin having the polar group or/and the elastomer having the polar group, and the composition (third component) containing one or more kinds of polymers selected from among the group of the thermoplastic polymer, the thermoplastic elastomer, and the unvulcanized rubber:

① Method of mixing and kneading the first component, the second component, and the third component all together ② Method of adding the first component to a composition obtained by preparing the second component, kneading or blending the first component and the composition, and mixing an obtained composition with the third component and kneading the composition and the third component ③ Adding the first component to a composition obtained by kneading or mixing a composition obtained by preparing the second component with a composition obtained by preparing the third component; and kneading the first component and the composition consisting of the second component and the third component.

It is possible to obtain the conductive or antistatic polymer composition very efficiently by carrying out any one of the above three methods. The method 2̂ is preferable to increase the conductivity efficiency of the salt. The methods 1̂ and 3̂ may be used in terms of the manufacturing cost and in dependence on the contents of the antistatic (conductive) polymer composition. The first component and the second component may be mixed with each other to form a master batch.

It is favorable that the antistatic (conductive) polymer composition contains not less than 0.1 parts by weight nor more than 65 parts by weight of the polymeric-type antistatic agent for the total weight of the polymers, namely, 100 parts by weight.

If the addition amount of the polymeric-type antistatic agent is less than 0.1 parts by weight, the antistatic (conductive) polymer composition is incapable of obtaining a sufficient antistatic performance. On the other hand, if the addition amount of the polymeric-type antistatic agent is more than 65 parts by weight, the effect of imparting antistatic properties to the antistatic (conductive) polymer composition cannot be increased, the manufacturing cost becomes high, and further the properties of the polymers may be deteriorated. The polymeric-type antistatic agent should be added to the polymers at more favorably not less than 0.5 nor more than 50 parts by weight and at most favorably not less than 2 parts by weight nor more than 30 parts by weight.

Even though the addition amount of the polymeric-type antistatic agent is small, the antistatic polymer composition is capable of realizing preferable antistatic properties without deteriorating the characteristics of the polymer and can be used as a resinous material or an elastomeric material having antistatic properties applicable to various products. The conductive polymer composition containing the thermoplastic polymer can be recycled and is flowable and thus has high moldability. Thus it is possible to reduce the manufacturing cost.

As the thermoplastic polymer of the second invention, including the polymer composition containing the polymeric-type charge prevention agent or/and the thermoplastic resin having the polar group or/and the elastomer having the polar group, known polymers can be used.

More specifically, it is possible to use olefin polymer (polyolefin, polypropylene, polybutane or the like), styrene polymer (polystyrene or the like), ethylene polymers (ethylene-vinyl acetate copolymer (EVA)), ethylene-methyl acrylate copolymer (EMA), ethylene-ethyl acrylate copolymer (EEA), ethylene-maleic anhydride copolymer, acrylonitrile-butadiene-styrene copolymer (ABS), acrylonitrile polymer (polyacrylonitrile, and the like), polyamide polymer (nylons such as nylon 6, nylon 66, nylon 610, nylon 11, nylon 12, and the like), polyacetal, saturated polyester (polyethylene terephthalate, polybutylene terephthalate, and all aromatic polyesters), unsaturated polyester, polyacrylate, polycarbonate, polyvinyl chloride, polyvinylidene chloride, fluorine polymers (polyvinyl fluoride (PVF)), tetrafluoroethylene-hexafluoropropylene copolymer, polyvinylidene fluoride, polytetrafluoroethylene (PTFE), tetrafluoroethylene-perfluoroalkyl vinyl ether copolymer, liquid crystal polyester, thermoplastic urethane resin, polysulfone, polyphenylene ether, and silicone polymers. These polymers can be used singly or in combination. Of these thermoplastic polymers, the olefin polymers and the styrene polymers are preferable because the olefin polymers and the styrene polymers are capable of providing higher antistatic property-imparting effect than the conventional charge prevention agents.

As the thermoplastic elastomer, the following known thermoplastic elastomers can be used: styrene thermoplastic elastomer, olefin thermoplastic elastomer (TPO), polyamide thermoplastic elastomer (TPAE), polyester thermoplastic elastomer (TPEE), urethane thermoplastic elastomer (TPU), vinyl chloride thermoplastic elastomer (TPVC), and fluorine-containing thermoplastic elastomer. More specifically, it is possible to use styrene-ethylene butylene-styrene block copolymer (SEBS), styrene-ethylene propylene-styrene block copolymer (SEPS), styrene-ethylene-ethylene propylene-styrene block copolymer (SEEPS), polyether-polyamide multi-block copolymer, and polyether-polyester (multi) block copolymer. These polymers can be used singly or in combination. Of these thermoplastic elastomers, the styrene thermoplastic elastomer and the olefin thermoplastic elastomer are preferable in that these polymers are capable of providing higher antistatic property-imparting effect than the conventional charge prevention agents.

As the unvulcanized rubber, known following rubbers can be used: natural rubber (NR), isoprene rubber (IR), butadiene rubber (BR), styrene butadiene rubber (SBR), butyl rubber (IIR), ethylene-propylene-diene rubber (EPDM), ethylene propylene rubber (EPM), chloroprene rubber (CR), acrylonitrile-butadiene rubber (NBR), chlorosulfonated polyethylene (CSM), Epichlorohydrin rubber (CO, ECO, GECO), chlorinated polyethylene, silicone rubber (Si), fluororubber, urethane rubber (U). These can rubbers be used singly or in combination. Of these rubbers, the butyl rubber (IIR), the ethylene-propylene-diene rubber (EPDM), and the ethylene propylene rubber (EPM) are preferable because these rubbers are resistant to heat.

As the third invention belonging to the second invention, the present invention provides the antistatic (conductive) polymer composition in which a crosslinkable rubber or/and a thermoplastic elastomer is dispersed by dynamic crosslinking.

Thereby the antistatic (conductive) polymer composition has rubberlike durability, elasticity, and flexibility; resinlike moldability, and excellent antistatic properties.

The antistatic polymer composition can be obtained as follows: After the crosslinkable rubber or/and the thermoplastic elastomer are dispersed in the thermoplastic resin or/and the thermoplastic elastomer or/and the unvulcanized rubber by dynamic crosslinking by an extruder or a kneader, the obtained composition is mixed with the polymeric-type antistatic agent kneaded in advance, while the obtained composition is being kneaded by the extruder or the kneader.

The heating temperature in the dynamic crosslinking operation is favorably 100° C. to 250° C. and more favorably 160° C. to 230° C. The heating time period is preferably 1 to 20 minutes. The heating temperature when the polymeric-type antistatic agent is mixed with the obtained composition is preferably 130° C. to 260° C. The heating time period is preferably 1 to 20 minutes.

As the extruder, it is possible to use a biaxial extruder and the like. As the kneader, a Banbury mixer and the like can be used.

In the case where the crosslinkable rubber or/and the thermoplastic elastomer are dispersed in the unvulcanized rubber by dynamic crosslinking, the polymeric-type antistatic agent is mixed with the obtained composition in a manner similar to the above-described manner. After the mixture is cooled, a vulcanizing agent, a vulcanizing accelerator and the like are added to the composition. Thereafter the mixture is molded and vulcanized to obtain a vulcanized rubber composition and products.

According to the above-described manufacturing method, the polymeric-type antistatic agent and the anion-containing salt having the fluoro group and the sulfonyl group contained therein are hardly distributed in a dynamically crosslinked domain but unevenly distributed to the matrix side of the antistatic polymer composition.

Therefore it is possible to prevent deterioration of the properties (rise of hardness, deterioration of compression set) of the antistatic (conductive) polymer composition and realize preferable moldability without adversely affecting the crosslinking of the rubber by the addition of the polymeric-type antistatic agent to the polymer component. Further it is unnecessary to increase the use amount of the polymeric-type antistatic agent and hence possible to reduce the material cost.

In the third invention, for imparting antistatic properties to the thermoplastic polymer and the thermoplastic elastomer by using the polymeric-type antistatic agent containing the anion-containing salt which has been added to the polymer composition without the intermediary of the medium consisting of the polyether-containing compound or the medium consisting of the low-molecular-weight polar compound whose number-average molecular weight is not more than 5000 (weight-average molecular weight is not more than 10000), it is preferable that the base component of the antistatic (conductive) polymer composition consists of a composition containing a compound (A), whose main component is styrene thermoplastic elastomer, in which a compound (B) containing a rubber component whose main component is EPDM is dispersed by dynamic crosslinking. Thereby it is possible to realize a low hardness and a low compression set and further rubberlike elasticity and flexibility and resinlike preferable moldability.

In the compound (B) containing the rubber component whose main component is EPDM, it is most preferable the rubber component consists of only the EPDM. In blending the EPDM with other rubbers, the mixing ratio of the EPDM to the entire rubber component is favorably not less than 50 wt % and more favorably not less than 80 wt %. Thereby it is possible to improve resistance to ozone, ultraviolet rays, and heat. As the other rubbers, diene rubber, butyl rubber, ethylene propylene rubber (EPM), and the like can be used. As the crosslinkable thermoplastic elastomer, it is possible to use styrene-isoprene-styrene block copolymer (SIS), styrene-butadiene-styrene block copolymer (SBS), and SIS and SBS partly hydrogenated. It is preferable to selectively hydrogenate the double bond of positions 1, 2 of the SBS to improve heat resistance.

It is favorable that the weight ratio between the styrene thermoplastic elastomer+the olefin resin and the rubber component containing the EPDM as its main component is 60:40 to 15:85. If the weight ratio of the rubber component is more than the above range, it is difficult to obtain preferable moldability. On the other hand, if the weight ratio of the rubber component is less than the above range, the compression set of the antistatic (conductive) polymer composition is liable to deteriorate. The weight ratio therebetween is more favorably 45:55 to 25:75.

The compound (A) contains not less than 15 parts by weight nor more than 500 parts by weight of a softener and favorably not less than 25 parts by weight nor more than 400 parts by weight thereof for 100 parts by weight of the rubber component. Thereby the antistatic (conductive) polymer composition has a proper degree of flexibility and elasticity.

If the compound (A) contains less than 15 parts by weight of the softener, the antistatic (conductive) polymer composition is liable to have a high hardness. On the other hand, if the compound (A) contains more than 500 parts by weight of the softener, the softener bleeds on the surface of the dynamically crosslinked composition or migrates to the rubber and inhibits crosslinking. Thereby the properties of the antistatic (conductive) polymer composition are liable to deteriorate.

The compound (A) contains not less than 1 part by weight nor more than 50 parts by weight, favorably not less than 2 parts by weight nor more than 40 parts by weight, and more favorably not less than 4 parts by weight nor more than 35 parts by weight of a resin containing the olefin resin as its main component for 100 parts by weight of the rubber component.

If the compound (A) contains less than 1 part by weight of the resin, it is impossible to confirm whether the effect of improving the processability has been obtained because the addition amount of the olefin resin is too small. On the other hand, if the compound (A) contains more than 50 parts by weight of the resin, a molded product of the polymer composition is liable to be high.

Olefin resins commercially available can be used singly or in combination. Polypropylene is particularly preferable because it has good processability, is capable of improving the strength of the antistatic (conductive) polymer composition, and is compatible with the EPDM.

The compound (B) contains not less than 15 parts by weight nor more than 600 parts by weight and favorably not less than 25 parts by weight nor more than 400 parts by weight of the softener for 100 parts by weight of the rubber component. Thereby the polymer composition has a proper degree of flexibility and elasticity.

If the addition amount of the softener is less than 15 parts by weight, a molded product is liable to have a high hardness. On the other hand, if the addition amount of the softener is more than 600 parts by weight, the softener bleeds on the surface of a dynamically crosslinked composition or inhibits crosslinking. Thereby the rubber component is not sufficiently crosslinked and thus the properties of the antistatic (conductive) polymer composition are liable to deteriorate. The weight of the rubber component means the weight of oil-non-extended rubber when the rubber component consists of the oil-non-extended rubber and the weight of only the rubber component obtained by subtracting the weight of an oil component from that of the oil-extended rubber when the rubber component consists of the oil-extended rubber.

As the softener, oil and plasticizer can be used. As the oil, it is possible to use mineral oils such as paraffin oil, naphthenic oil, aromatic series; and known synthetic oils consisting of oligomer of hydrocarbon series, and process oil. As the plasticizer, it is possible to use dioctyl phthalate (DOP), dibutyl phthalate (DBP), dioctyl sebacate (DOS), and dioctyl adipate (DOA).

It is preferable that the dynamic crosslinking is performed by resin crosslinking. A synthetic resin crosslinking agent allows rubber to allow rubber to make a crosslinking reaction by heating or the like. Unlike the case in which sulfur and a vulcanizing accelerator are used in combination, the synthetic resin crosslinking agent is preferable because owing to its use, blooming hardly occurs and the antistatic (conductive) polymer composition has a low compression set. The antistatic (conductive) polymer composition is allowed to have dimensional accuracy and long life. Phenol resin is particularly preferable. Crosslinking can be preferably made by using peroxides because owing to its use, blooming hardly occurs and allows the antistatic (conductive) polymer composition to have a low compression set. Sulfur may be used for crosslinking.

The resin crosslinking agent is added at favorably not less than 1 nor more than 50 parts by weight and more favorably not less than 8 nor more than 15 parts by weight to 100 parts by weight of the rubber component.

To accomplish a crosslinking reaction properly by using the resin crosslinking agent, a crosslinking activator may be used. As the crosslinking activator, metal oxides are used. Zinc oxide and zinc carbonate are particularly preferable.

To improve the mechanical strength of the antistatic (conductive) polymer composition, fillers may be used, provided that the addition thereof does not deteriorate colorability, the compression set, and hardness of the antistatic (conductive) polymer composition. An age resistor, wax, and the like may be used.

Hydrogenated styrene thermoplastic elastomers is preferable. The double bond of the hydrogenated styrene thermoplastic elastomer is saturated and thus has a low hardness and is durable. Since the double bond of the hydrogenated styrene thermoplastic elastomer is saturated, the hydrogenated styrene thermoplastic elastomer does not react with a crosslinking agent in dynamic crosslinking. Therefore the elastomer composition dynamically crosslinked is capable of displaying desired thermoplasticity.

It is possible to obtain a polymeric-type antistatic agent by mixing the anion-containing salt with a polymer having cyano group, instead of mixing the anion-containing salt with the polyoxyalkylene copolymer or the polyether block polyolefin copolymer.

It is also possible to obtain the antistatic polymer composition by forming the antistatic agent as a master batch and then mixing an identical or different kind of a polymer having the cyano group with the master batch.

From the above-described viewpoint, as the fourth invention belonging to the second invention, the present invention provides an antistatic (conductive) polymer composition by mixing a antistatic agent containing an anion-containing salt, having a fluoro group and a sulfonyl group, added to a polymer with an identical or different kind of a polymer having the cyano group.

As the polymer having the cyano group, it is preferable to use acrylonitrile-butadiene rubber (NBR), hydrogenated acrylonitrile-butadiene rubber, carboxyl-modified acrylonitrile-butadiene rubber, acrylonitrile butadiene-isoprene rubber (NBIR), liquid nitrile rubber (liquid acrylonitrile-butadiene rubber), and latices of these polymers. This is because these polymers can be mass-produced and hence commercially available at a low cost and with ease.

The conventional art has difficulty in reducing the electric resistance of low-nitrile acrylonitrile-butadiene rubbers, but the present invention is capable of effectively reducing its electric resistance by adding the anion-containing salt thereto. Because the low-nitrile acrylonitrile-butadiene rubbers have low glass transition temperatures (Tg), they have a low degree of dependence on environment in its viscoelasticity and electric resistance and show very favorable characteristics in the neighborhood of the room temperature. It is possible to make the degree of dependence on environment in its electric resistance of the low-nitrile acrylonitrile-butadiene rubbers lower than the moderate-high nitrile acrylonitrile-butadiene rubbers and high nitrile acrylonitrile-butadiene rubbers because it is possible to make the degree of dependence on environment in the mobility of molecules thereof in the region of practical use.

Therefore it is preferable that the polymer having the cyano group is of low-nitrile type in which the central value of the content of acrylonitrile is not more than 24 wt %.

The anion-containing salt may be added to a mixture of the polymer having the cyano group and polymers other than the polymer having the cyano group. But the mixture contains the polymer having the cyano group at favorably not less than 20 wt % and more favorably not less than 30 wt % of the entire polymer component. If the ratio of the polymer having the cyano group is less than 20 wt %, the antistatic (conductive) polymer composition is incapable of obtaining a sufficiently low electric resistance.

It is preferable that the anion-containing salt is added to the polymer having the cyano group to form a master batch. Thereby it is possible to make the volume resistivity of the antistatic (conductive) polymer composition uniform.

The electric resistance can be reduced by adding a very small amount of the anion-containing salt to the polymer. Thus when a necessary amount of the anion-containing salt is directly added to the polymer component, there is a possibility that an obtained concentration deviates from a desired concentration. Consequently there is a possibility that an obtained electric resistance deviates from a target electric resistance or problems occur in the concentration of the salt and the uniformity of the electric resistance.

The master batch can be formed by kneading the polymer having the cyano group and the anion-containing salt. But to improve processability in the kneading operation, it is preferable to add a processing aid such as stearic acid and the same fillers as those contained in an end composition to the polymer in addition to the anion-containing salt.

Many of the anion-containing salts are hygroscopic and are liable to adhere to a wall surface of an enclosed kneader, which makes it difficult to perform works. The anion-containing salt does not adhere to the wall surface of the enclosed kneader when it is prepared as a master batch. Thereby it is possible to improve processability and thus work efficiency and easy to store the master batch.

It is favorable that the content of the anion-containing salt of the master batch is not less than 1 wt % nor more than 40 wt %. If the content of the anion-containing salt is less than 1 wt %, there is a fear that owing to errors during measurement, the concentration of the anion-containing salt of the master batch deviates from a target concentration or that the concentration of the salt in the master batch becomes partly nonuniform. On the other hand, if the content of the anion-containing salt is more than 40 wt %, it is difficult to disperse the salt uniformly in the polymer because the content of the salt is too much. The content of the anion-containing salt of the master batch is more favorably not less than 2 wt % nor more than 30 wt % and most favorably not less than 5 wt % nor more than 15 wt %.

It is preferable that the acrylonitrile-butadiene rubber contains liquid acrylonitrile-butadiene rubber. In the case where the acrylonitrile-butadiene rubber containing the liquid acrylonitrile-butadiene rubber is used, the polymer chain becomes movable. Thus the polymer composition has excellent processability and ion transport efficiency becomes high and hence has a low volume resistivity. Further such liquid acrylonitrile-butadiene rubber is crosslinkable, bleeding hardly occurs. In addition, it can be extruded favorably. Thus it is possible to obtain a conductive roller and a conductive belt having a smooth surface. A mixture of high-molecular-weight NBR and liquid NBR can be preferably used because it is capable of preventing a photosensitive member from being stained and keeping the property of the polymer composition preferable. "Nipol DN223" produced by Zeon Corporation can be used.

As described above, after the polymeric-type antistatic agent is formed by using the polymer having the cyano group and the anion-containing salt having the fluoro group and the sulfonyl group, other polymer composition may be added to the polymeric-type antistatic agent. As the other polymer composition, it is possible to use a rubber component containing diene rubber as its main component and thermoplastic resins or/and a thermoplastic elastomer. For example, the rubber component containing the diene rubber as its main component may be co-crosslinked with a sulfur vulcanizing agent, a sulfur vulcanizing accelerator or a crosslinking agent of a peroxide to obtain a vulcanized rubber composition and molded rubber products.

A crosslinking agent, a vulcanizing accelerator, and a vulcanizing assistant are added to the polymer having the cyano group, the thermoplastic resins or/and the thermoplastic elastomer being kneaded to dynamically crosslink the polymer having the cyano group. Thereby the antistatic (conductive) thermoplastic elastomer composition is obtained. In this case, as the matrix resin, a polyamide thermoplastic elastomer or thermoplastic polyurethane is preferably used.

An appropriate amount of an electroconductive filler may be added so that the ionic-conductivity is not deteriorated. Known electroconductive fillers such as carbon black, electroconductive zinc white can be used.

As the vulcanizing system of the fourth invention, sulfur system is suitable as the vulcanizing system because it ralizes a low electric resistance and hardly stains the photosensitive member. As the vulcanizing accelerator, it is preferable to use dibenzothiazolyl disulfide and tetramethylthiuram monosulfide in combination. Instead of the dibenzothiazolyl disulfide, 2-mercaptobenzothiazole may be used. The vulcanizing agent such as sulfur is added to 100 parts by weight of the entire polymer component at not less than 0.2 nor more than 10 parts by weight, favorably at not less than 0.5 nor more than 5 parts by weight, and most favorably at not less than 1 nor more than 3 parts by weight.

The vulcanizing accelerator is added to 100 parts by weight of the entire polymer component at not less than 0.5 nor more than 8 parts by weight, favorably at not less than 1 nor more than 5 parts by weight, and most favorably at not less than 2 nor more than 4 parts by weight.

The vulcanization to be performed to obtain a vulcanized rubber composition, a known method can be used. For example, it is possible to accomplish vulcanization in a vulcanizing can pressurized by water vapor or use press vulcanization. A secondary vulcanization may be performed as necessary. It is possible to carry out a successive vulcanization method in dependence on a mixing ratio.

It is possible to accomplish vulcanization with peroxides. It is possible to prevent the photosensitive member from being stained by performing vulcanization with peroxides in combination with the secondary vulcanization. Considering that the antistatic (conductive) polymer composition is used for the conductive roller or the conductive belt for use in an electrophotographic mechanism, it is desirable to set conditions in which a sufficient amount of vulcanization can be obtained to prevent the conductive roller or the conductive belt from staining the photosensitive member and reduce the permanent compression set of the photosensitive member of the conductive roller or the conductive belt.

As an example of the methods of forming the antistatic (conductive) polymer composition of the fourth invention, the polymer having the cyano group, the master batch containing the anion-containing salt, the vulcanizing agent, and additives (vulcanizing accelerator, filler, age resistor and the like) to be used as necessary are fused and kneaded. Then fusing and kneading are performed by a known method. For example, by using a known rubber kneader such as an open roll or an enclosed kneader and the like, the components are kneaded at 20° C. to 130° C. for 2 to 10 minutes. It is preferable to use the enclosed kneader to secure safety in operation and knead a large amount of the material efficiently. Thereafter vulcanization is performed at 140° C. to 170° C. It is possible to form the master batch of the anion-containing salt, but the anion-containing salt may be kneaded with the components.

As the fifth invention belonging to the second invention, the present invention provides an antistatic (conductive) polymer composition, whose conduction is improved greatly, formed by adding a antistatic agent containing the anion-containing salt having the fluoro group and the sulfonyl group, and adding a polymer having an ester structure to a low-polar polymer composition consisting of any one of an olefin resin, an olefin thermoplastic elastomer, and a styrene thermoplastic elastomer.

It is preferable to use polyether block polyolefin as a polymer forming the antistatic agent, namely, as the medium of the salt. By using the polyether block polyolefin as the medium, the salt is stabilized to a higher extent by oxygen atoms contained in the ether linkage. Thus it is possible to obtain a lower electric resistance. Owing to structures other than the ether linkage in the block, it is possible to secure the compatibility of the polymer having the ester structure with other polymers (olefin resin, olefin thermoplastic elastomer, and styrene thermoplastic elastomer). Therefore the properties of the other polymers are hardly deteriorated and the obtained antistatic (conductive) polymer composition has favorable properties and moldability.

More specifically, the antistatic (conductive) polymer composition contains the following three components A, B, and C essentially:

(A): The low-polar polymer composition consisting of one polymer selected from among the olefin resin, the olefin thermoplastic elastomer, and the styrene thermoplastic elastomer or a mixture thereof;

(B): The anion-containing salt specified by the chemical formulas 1 through 3 shown below;

Chemical formula 1

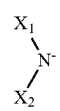

Chemical formula 2

$X_1\text{-}O^-$

Chemical formula 3

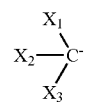

where each of $X_1$, $X_2$, and $X_3$ are identical to each other or different from each other and indicate a functional group including C, —F, and —SO$_2$— and having 1 to 8 carbon atoms.

(C): The polymer having the ester structure

The above-described low-polar polymer composition has a high electric resistance and is not compatible with the polymer, having the ether linkage, such as the polyether block polyolefin and the like that is used as the medium for the salt. Therefore, to obtain a desired conductivity, it is necessary to increase the addition amount of the salt and that of the polymer, having the ether linkage, such as the polyether block polyolefin that is used as the medium for the salt. By using the polymer having the ester structure in combination with the low-polar polymer, the above-described compatibility and electric conduction of the antistatic (conductive) polymer composition is improved and the addition amount of the salt and the polymer, having the ether linkage, such as the polyether block polyolefin that is used as the medium for the salt is reduced. The polymer having the ester structure has an operation of stabilizing cations generated from the salt.

The polymer having the ester structure shown by the above (C), vinyl acetate-ethylene copolymer, ethylene-vinyl acetate copolymer or a mixture of these two copolymers are listed. Above all, the vinyl acetate-ethylene copolymer, the ethylene-vinyl acetate copolymer or the mixture of these two copolymers containing not less than 40 wt % nor more than 90 wt % of vinyl acetate is preferable. These polymers cost ¥500 to ¥1000 per kilogram and thus are much less expensive than the above-described addition salt and the polyether block polyolefin. Thus these polymers are preferable in terms of reduction of the material cost.

The polymer having the ester structure is added at about 1 to 40 parts by weight to 100 parts by weight of the low-polar polymer composition. If the addition amount of the polymer having the ester structure is more than 40 parts by weight, the properties of the polymer composition deteriorate. That is, the moduli deteriorates and permanent compression set increases. If the addition amount of the polymer having the ester structure is less than 1 part by weight, it is impossible to display the compatible effect of making the low-polar polymer composition with the anion-containing salt shown by the chemical formulas 1 through 3 or/and with the polymer, having the ether linkage, such as the polyether block polyolefin that is used as the medium for the salt.

The polymer having the ester structure is added favorably at about 3 to about 30 parts by weight and more favorably at about 5 to about 25 parts by weight to 100 parts by weight of the low-polar polymer composition.

In the low-polar polymer composition shown by the above (A), polypropylene or polyethylene is used preferably as the olefin resin.

The following olefin thermoplastic elastomers are preferably used: (1) polyolefin in which rubber dynamically crosslinked with a crosslinking agent is dispersed, (2) olefin thermoplastic elastomer composed of a hard segment consisting of a crystalline phase and a soft segment consisting of an amorphous phase, and (3) olefin thermoplastic elastomer, described in above (2), partly crosslinked with an organic peroxide or the like.

The following styrene thermoplastic elastomers are preferably used: (1) styrene thermoplastic elastomer in which rubber dynamically crosslinked with a crosslinking agent is dispersed, (2) styrene thermoplastic elastomer composed of a hard segment consisting of polymers of styrene monomers and a soft segment consisting of polymers of olefin monomers, and (3) styrene thermoplastic elastomer, described in above (2), partly crosslinked with an organic peroxide or the like.

As described above, the thermoplastic resin or/and the thermoplastic elastomer in which crosslinkable rubber is dynamically crosslinked and dispersed is suitably used as the low-polar polymer composition. These low-polar polymer compositions have rubberlike durability, elasticity, and flexibility, and resinlike moldability. Thus the antistatic (conductive) polymer composition containing the low-polar polymer composition has high performance, as described in detail below.

More specifically, the anion-containing salt shown by the chemical formulas 1 through 3 and the polymer such as the polyether block polyolefin, having the ether linkage, which is used as the medium for the anion-containing salt are hardly included in a domain of the low-polar polymer composition dynamically crosslinked but are unevenly distributed in the matrix of the polymer composition. Therefore crosslinking of the rubber is not adversely affected by the addition of the anion-containing salt and the polymer such as the polyether block polyolefin, having the ether linkage, which is used as the medium for the anion-containing salt. Consequently it is possible to prevent the properties of the antistatic (conductive) polymer composition containing these components from deteriorating, restrain a reduction of the hardness and permanent compression set thereof, and realize preferable moldability and processability.

In the olefin thermoplastic elastomer, ethylene-propylene rubber (EPM), ethylene-propylene-diene rubber (EPDM) or butyl rubber are listed as rubbers that are dynamically crosslinked with a crosslinking agent, with the rubbers being dispersed in the polyolefin. While the polyolefin and the rubber such as the EPDM are being kneaded, a crosslinking agent capable of crosslinking the rubber is added to the mixture and the rubber is finely dispersed in the polyolefin while the crosslinking is progressing. Thereby the olefin thermoplastic elastomer is obtained.

Although the styrene thermoplastic elastomer is not limited to specific one, hydrogenated styrene thermoplastic elastomer is preferable. For example, styrene-isoprene-styrene block copolymer (SIS) and styrene-butadiene-styrene block copolymer (SBS) are preferable.

Of the styrene thermoplastic elastomer, the ethylene-propylene rubber (EPM), the ethylene-propylene-diene rubber (EPDM), and the butyl rubber and the like are crosslinkable. The above-described dynamically crosslinkable elastomer is obtained by adding a rubber-crosslinkable crosslinking agent to the rubber while the rubber and the styrene thermoplastic elastomer are being kneaded and finely dispersing the rubber in the styrene thermoplastic elastomer.

It is preferable that the main component of the low-polar polymer composition consists of a mixture of two or three kinds of the three kinds of the polymers described in the above (A). It is preferable to mix the styrene thermoplastic elastomer and the olefin resin with each other.

It is preferable that the weight ratio of the rubber component containing the EPDM as its main component to the styrene thermoplastic elastomer and the olefin resin is 2/3 to 17/3. To obtain favorable moldability, the weight ratio of the former to the latter is preferably not more than 17/3. To maintain the permanent compression set, the weight ratio of the former to the latter is preferably not less than 2/3.

It is preferable that in the polymer composition, a compound (C2) containing a rubber component containing EPDM as its main component is dispersed by dynamic crosslinking in a compound (C1) containing the styrene thermoplastic elastomer and the olefin resin.

The polymer composition is described in detail below.

In addition to the styrene thermoplastic elastomer, the compound (C1) contains the olefin resin at not less than 1 part by weight nor more than 50 parts by weight, favorably at not less than 2 parts by weight nor more than 40 parts by weight, and most favorably at not less than 4 parts by weight nor more than 35 parts by weight for 100 parts by weight of the rubber component.

To improve processability, it is preferable that the addition amount of the olefin resin is not less than 1 part by weight.

To prevent the rise of the hardness of a product formed by molding the polymer composition, it is preferable that the addition amount of the olefin resin is not more than 50 parts by weight. Olefin resins commercially available can be used. The olefin resins can be used singly or in combination. In terms of processability of the polymer composition, its strength, and the compatibility with the EPDM, polypropylene is particularly preferable as the olefin resin.

In the compound (C2) containing the rubber component whose main component is EPDM, it is preferable the rubber component consists of the EPDM. In blending the EPDM with other rubbers, the mixing ratio of the EPDM to the entire rubber component is favorably not less than 50 wt % and more favorably not less than 80 wt %. Thereby it is possible to improve resistance to ozone, ultraviolet rays, and heat. As the other rubbers, diene rubber, butyl rubber, ethylene propylene rubber (EPM), and the like can be used.

It is preferable to add a softener to the compound (C1) and the compound (C2). Thereby it is possible to form the polymer composition having a proper degree of flexibility and elasticity. The softener is added to the compound (C1) at favorably not less than 15 parts by weight nor more than 500 parts by weight and more favorably not less than 25 parts by weight nor more than 400 parts by weight thereof for 100 parts by weight of the rubber component contained in the compound (C2). The softener is added to the compound (C2) at favorably at not less than 15 parts by weight nor more than 600 parts by weight and favorably not less than 25 parts by weight nor more than 400 parts by weight for 100 parts by weight of the rubber component. This range of the addition amount of the softener is set to prevent the softener from bleeding on the surface of a dynamically crosslinked composition or from migrating to the rubber and inhibiting crosslinking. Thereby it is possible to prevent deterioration of the properties of the compound (C1) and the compound (C2). The weight of the rubber component in the compound (C2) or the part by weight of the rubber component in the compound (C2) in specifying the amount of the olefin resin and the softener contained in the compound (C1) mean the weight of oil-non-extended rubber when the rubber component consists of the oil-non-extended rubber and the weight of only the rubber component obtained by subtracting the weight of an oil component from that of the oil-extended rubber when the rubber component consists of the oil-extended rubber.

As the softener, oil or a plasticizer similar to those described above can be used.

It is preferable that the dynamic crosslinking of the rubber in the olefin thermoplastic elastomer and the styrene thermoplastic elastomer is performed by resin crosslinking, as described above.

It is preferable that the anion-containing salt shown by the chemical formulas 1 through 3 of the above-described (B) is added at not less than 0.01 nor more than 20 parts by weight to 100 parts by weight of the low-polar polymer composition.

As the method of manufacturing the antistatic (conductive) polymer composition of the fifth invention, the following manufacturing methods (a), (b), and (c) are used:

(a) The anion-containing salt shown by the chemical formulas 1 through 3 and/or the composition containing the salt, the polymer having the ester structure, and the low-polar polymer composition are kneaded all together.

(b) After the anion-containing salt shown by the chemical formulas 1 through 3 and/or the composition containing the salt are added to the polymer having the ester structure, they are kneaded or mixed with one another. After the composition obtained is added to the low-polar polymer composition, these compositions are kneaded.

(c) The polymer having the ester structure and the low-polar polymer composition are kneaded or mixed with one another to obtain a composition. After the anion-containing salt shown by the chemical formulas 1 through 3 and/or the composition containing the salt are added to the composition, these compositions are kneaded.

It is preferable that the anion-containing salt shown by the chemical formulas 1 through 3 is added to the polymer such as the polyether block polyolefin having the ether linkage and uniformly dispersed therein.

It is possible to color the antistatic (conductive) polymer composition of each of the second through fifth invention and unnecessary to use a large amount of the antistatic agent and the low-molecular-weight medium therefor. Thus the thermoplastic resin and the thermoplastic elastomer can be used suitably for products such as the conductive roller, the conductive belt, the paper-feeding roller for office appliances.

In the third invention, the antistatic properties and the electric conduction can be secured efficiently by unevenly distributing a small amount of the high-performance polymeric-type antistatic agent in the thermoplastic elastomer composition having a permanent compression set as low as that of a vulcanized rubber. Because only a small amount of the polymeric-type antistatic agent is added to the thermoplastic elastomer composition, other properties of the antistatic (conductive) polymer composition such as the permanent compression set, hardness, and the like are not deteriorated. Thereby it is possible to manufacture the above-described products which can be used practically and recycled.

Since the materials for the antistatic (conductive) polymer composition do not contain chlorine, the entire antistatic (conductive) polymer composition does not contain chlorine. Thereby it is possible to prevent a metal surface from being corroded, rusted or stained, and toxic gases such as hydrogen chloride and harmful substances such as dioxin from generating when the antistatic (conductive) polymer composition is burnt to discard it.

As products formed from the polymeric-type antistatic agent or the antistatic (conductive) polymer composition containing the polymeric-type antistatic agent, of the present invention, it is possible to list parts of electronic equipment, apparatus for manufacturing electronic parts, parts of household appliances, parts of office appliances, IC tray, communication apparatus, housing parts, parts of optical apparatus, parts of vehicles, building materials, floor materials, tires, hoses, packing films, packing materials, sealing materials, gloves, and synthesized leather. These products are used for those requiring high antistatic performance and high electric conduction.

The polymer composition of the present invention can be used suitably for the conductive roller (transfer roller, charging roller, developing roller, toner supply roller) for office appliances and conductive belt (transfer belt, intermediate transfer belt, fixing belt) for office appliances required to have a uniform electric resistance and semiconductivity because the conductive roller and the conductive belt have exchange with toner and the like when they are used with an electric field applied thereto; the paper-feeding roller and the paper-feeding belt, for office appliances, which is apt to be charged by friction in separating and feeding a large number of paper; and a driving roller in which static electricity is liable to accumulate, because it drives the intermediate transfer belt which rotates while feeding paper and toner image.

The polymer composition of the present invention has high antistatic performance. Thus the polymer composition is capable of preventing accumulation of static electricity on rollers and belts and thus preventing images from becoming nonuniform.

By using the antistatic (conductive) polymer composition, of the fourth invention or the method of manufacturing the above-described antistatic polymer composition, the present invention provides a shoe sole, an adhesive agent, a fuel hose, a hose such as an oil-resistant hose, an oil seal, a packing, a gasket, a diaphragm, a fiber-processing roller, a textile roller, gloves, a printing roller, and a printing blanket. Further, especially the present invention provides a conductive roller and belt having a low electric resistance and a mechanical property. The conductive polymer composition of the present invention has a high-performance conductive in the normal condition (normal temperature and humidity) and in the low temperature and humidity, therefor has an effect of charge prevention on environment. In result, rubber products used under the low temperature and humidity are manufactured by the polymer composition preferably, because a problem is not occurred by the static electricity.

The conductive roller and the conductive belt are formed by molding the conductive polymer composition. The conductive polymer composition has a low volume resistivity and hardness and does not stain the photosensitive member. Further blooming and bleeding do not occur in the conductive polymer composition. Therefore the conductive roller composed of the conductive polymer composition can be suitably used as a transfer roller, a charging roller, a toner supply roller, and a developing roller.

The conductive roller can be produced by using conventional methods. For example, the conductive polymer composition (kneaded components) is preformed tubularly with a single-axis extruder. Then the preform is vulcanized at 160° C. for 10 to 70 minutes. Thereafter a metal shaft is inserted into a hollow portion of the vulcanized tube. After the surface of the rubber is polished, the rubber is cut to a predetermined size to obtain a roller. An optimum vulcanizing time period should be set by using a vulcanization testing rheometer (for example, Curelastometer). The vulcanization temperature may be set around 160° C. in dependence on necessity.

The conductive belt can be formed from the antistatic (conductive) polymer composition of the present invention described in claim 15 by using conventional methods. For example, the antistatic (conductive) elastomer composition (kneaded components) is molded in the shape of a belt by an extrusion machine. Then the preform is vulcanized at 160° C. for 10 to 70 minutes with the preform fitted in a mandrel (vulcanizing core). The vulcanizing time period can be set around 160° C. in dependence on necessity. In dependence on necessity, the conductive belt may have a coating layer, consisting of a coating agent such as fluorine, urethane or the like, formed on the peripheral surface thereof so that the conductive belt can be used suitably as a transfer belt, a transport belt, an intermediate transfer belt.

It is favorable that the antistatic (conductive) polymer composition of the second through fifth invention has a volume resistivity not more than $10^{11.0}$ Ω·cm or/and a surface resistivity not more than $10^{11.0}$Ω, when the volume resistivity and the surface resistivity are measured at a temperature of 23° C. and a relative humidity of 55% with a voltage of 1000 applied thereto in accordance with the method specified in JIS K6911. If the volume resistivity of the antistatic (conductive) polymer composition is more than $10^{11.0}$ Ω·cm, antistatic products composed thereof are incapable of securing preferable electric conduction or antistatic properties and cannot be put to practical use.

The conductive roller or the conductive belt composed of the antistatic (conductive) polymer composition has a low efficiency in its transfer, charging, and toner supply operation and hence cannot be put into practical use. It is more favorable that the antistatic (conductive) polymer composition has a volume resistivity not less than $10^{5.0}$ Ω·cm nor more than more than $10^{10.5}$ Ω·cm, i.e., it is favorable that the antistatic (conductive) polymer composition is semiconductive. It is most favorable that the antistatic (conductive) polymer composition has a volume resistivity not less than $10^{6.0}$ Ω·cm nor more than more than $10^{10.5}$ Ω·cm

If the surface resistivity of the antistatic (conductive) polymer composition is more than $10^{11.0}$ Ω·cm, it is impossible to obtain a sufficient antistatic effect. In this case, a paper-feeding roller, formed from the antistatic (conductive) polymer composition, for use in an ink jet printer causes a shear in printing. The surface resistivity of the antistatic (conductive) polymer composition is more favorably not less than $10^{5.0}$ Ω·cm nor more than $10^{10.5}$ Ω·cm and most favorably not less than $10^{6.0}$ Ω·cm nor more than $10^{10.0}$ Ω·cm.

The antistatic (conductive) polymer composition has a volume resistivity favorably and a surface resistivity not more than $10^{12.5}$ Ω·cm and $10^{12.5}$Ω, more favorably not more than $10^{12.0}$ Ω·cm and $10^{12.0}$Ω, and most favorably not more than $10^{11.5}$ Ω·cm and $10^{11.5}$Ω respectively, when the volume resistivity is measured at a temperature of 10° C. and a relative humidity of 15%.

In the case where the antistatic (conductive) polymer composition of the fourth invention is used for a conductive roller or a conductive belt, it has favorably not more than $10^{9.5}$ (Ω·cm) more favorably not more than $10^{9.0}$ (Ω·cm), and more favorably not less than $10^{8.5}$ Ω·cm) in its volume resistivity specified in JIS K6911, when the resistivity is measured at a temperature of 23° C. and a relative humidity of 55% (normal temperature and humidity) or at a temperature of 10° C. and a relative humidity of 15% (low temperature and humidity) with 500V being applied to the conductive roller or the conductive belt.

Although the NBR which is the representative of the polymer having the cyano group has a volume resistivity of $10^{10.0}$ (Ω·cm) to $10^{11.0}$ (Ω·cm) when it is measured in the above-described condition, the present invention is intended to impart a higher degree of electric conduction and antistatic performance.

If the volume resistivity is more than $10^{9.5}$(Ω·cm), the conductive roller or the conductive belt has a low efficiency in its transfer, charging, and toner supply operation, although the degree of efficiency depends on the kind, use, and a electrophotographic system. Hence the conductive roller or the conductive belt cannot be put into practical use. If electric conduction is not imparted to a polymer composition or imparted by the conventional method, the polymer composition is liable to have a low electric resistance at a low temperature and humidity. The lower the volume resistivity, the better. The lower limit value of the electric resistance is about $10^{5.0}$(Ω·cm). In the case where the antistatic (conductive) polymer composition is used for other industrial products which require to be prevented from being statically charged, it is necessary to set the volume resistivity close to the above value.

It is favorable that a product formed from the above-described antistatic (conductive) polymer composition and particularly a product formed from the above-described antistatic (conductive) polymer composition of the third invention has a permanent compression set not more than 30% when the compression set is measured at a temperature of 70° C. for 22 to 24 hours at a compression rate of 25% in accordance with Permanent set testing methods for rubber, vulcanized or thermoplastic specified in JIS K6262. If the compression set is more than 30%, conductive (antistatic) products such as the conductive roller or the conductive belt formed from the molded conductive (antistatic) polymer composition, for use in a copying apparatus, a printer, a facsimile, and the like have a large dimensional change. Thus the conductive roller and the like cannot be practically used. It is more favorable that the compression set measured in the above-described conditions is not more than 25%. The smaller the compression set, the better.

BRIEF DESCRIPTION OF THE DRAWINGS

FIG. 8 is an explanatory view for explaining the effect of the fourth invention, in which

DETAILED DESCRIPTION OF THE PREFERRED EMBODIMENTS

The embodiments of the present invention will be described below with reference to the drawings.

Figure 1:
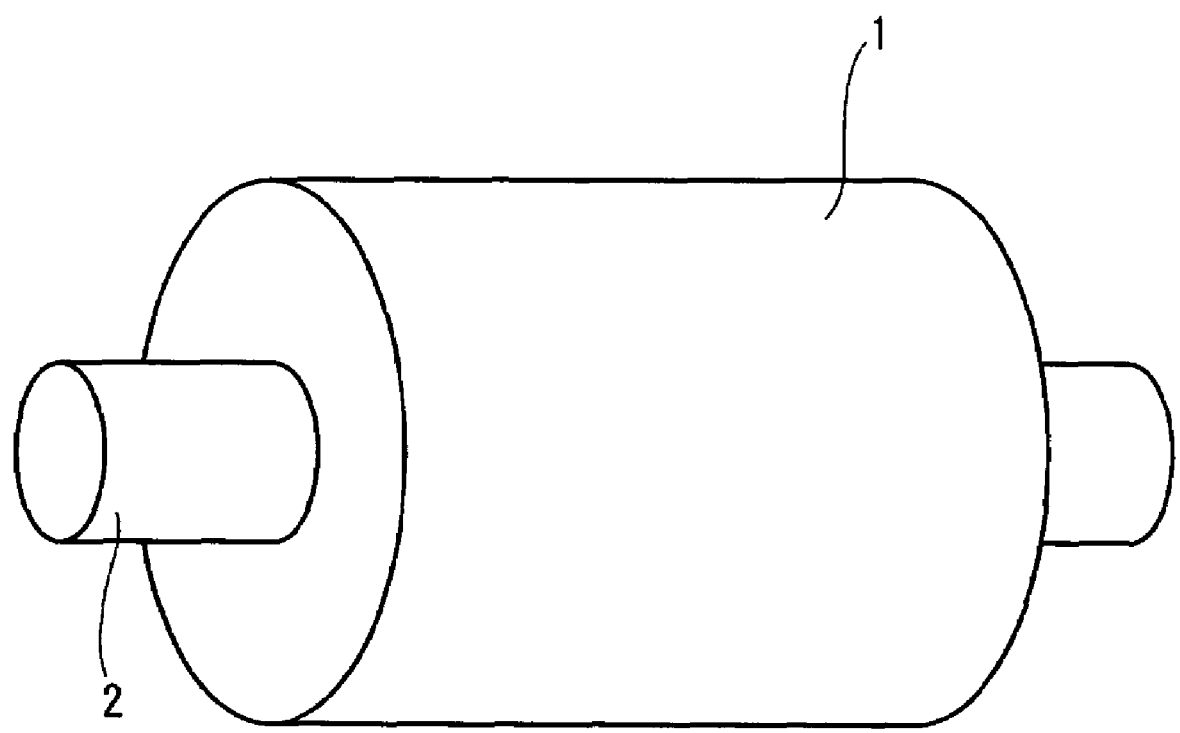
FIG. 1 is a schematic view showing a conductive roller formed by molding a conductive polymer composition of the present invention.

FIG. 1 shows a conductive roller 1 composed of the antistatic polymer composition of the third invention, as described in claim 9, of the second invention relating to the conductive and antistatic polymer composition containing the polymeric-type antistatic agent of the first invention. The tubular conductive roller 1 consists of a polymer composition having a composition described below. A metal shaft 2 is inserted into a hollow portion of the conductive roller 1 by press fit or the conductive roller 1 and the metal shaft 2 are bonded to each other with an adhesive agent.

The conductive polymer composition consists of a styrene thermoplastic elastomer (TPV), which is dynamically crosslinked, which is used as its polymer and the polymeric-type antistatic agent added to the TPV.

The polymeric-type antistatic agent contains a polymer composition consisting of a polymeric-type charge prevention agent whose main component is a resin or/and an elastomer; and at least one anion-containing salt uniformly dispersed in the polymer composition without the intermediary of a medium selected from among the group of a low molecular weight polyether-containing compound and a low-molecular-weight polar compound. These compounds are not fixed by crosslinking and have a number-average molecular weight not more than 5000 and a weight-average molecular weight not more than 10000. The above-described anion-containing salt is selected from among the salts shown by the chemical formulas 1 through 3 described previously and has a fluoro group and a sulfonyl group.

Three parts by weight of the polymeric-type charge prevention agent is added to 100 parts by weight of the styrene TPV.

5.3 parts by weight of the anion-containing salt having the fluoro group and the sulfonyl group is added to 100 parts by weight of an entire resinous component contained in the composition of the polymeric-type charge prevention agent.

More specifically, a polyether/polyolefin block copolymer is used as the polymeric-type charge prevention agent. Lithium-bis (trifluoromethanesulfonyl) imide is used as the anion-containing salt having the fluoro group and the sulfonyl group.

The styrene TPV consists of a compound (A) and a compound (B) dispersed in the compound (A) by dynamic crosslinking. The compound (A) contains 20 parts by weight of styrene thermoplastic elastomer, 15 parts by weight of polypropylene (PP) which is an olefin resin, and 35 parts by weight of oil. The compound (B) contains oil-extended EPDM in which 65 parts by weight of a rubber component are contained.

The crosslinking agent consists of 2.0 parts by weight of a phenol resinous crosslinking agent and 5.9 of another kind of the phenol resinous crosslinking agent. As a crosslinking activator, 3.3 parts by weight of zinc oxide is used.

The conductive polymer composition having the antistatic properties has a permanent compression set of 18%, when the compression set is measured at a temperature of 70° C. for 22 to 24 hours at a compression rate of 25% in accordance with Permanent set testing methods for rubber, vulcanized or thermoplastic specified in JIS K6262. The conductive polymer composition has a volume resistivity of $10^{9.9}$($\Omega$·cm) and a surface resistivity of $10^{10.1}$($\Omega$), when the volume resistivity and the surface resistivity are measured at a temperature of 23° C. and a relative humidity of 55% with a voltage of 1000, applied thereto in accordance with the method specified in JIS K6911. The conductive polymer composition has a hardness of 46, when the hardness is measured at a temperature of 23° C. and a relative humidity of 55% with a voltage of 1000 applied thereto in accordance with the method specified in durometer hardness test type A of JIS K6253.

The conductive polymer composition secures sufficient electric resistance-controlling performance (low electric resistance) by unevenly distributing a very small amount (about 3%) of the polymeric-type antistatic agent (containing mixture of polymeric-type charge prevention agent and salt) in the matrix phase by utilizing dynamic crosslinking. It will be understood that the conductive polymer composition of the present invention is distinguished over the conventional one in comparison with the conductive polymer composition of the comparison example 12 that will be described later.

The method of producing the conductive roller 1 is described below.

The compound (A), the compound (B), and additives are kneaded at a predetermined temperature for a predetermined period of time by using an extruder or a kneader. After the rubber is dispersed in the compound (A) by dynamic crosslinking, a required amount of the polymeric-type antistatic agent is added to the mixture of the above-described components. All the components are kneaded at a predetermined temperature for a predetermined period of time by using the extruder or the kneader again to obtain a conductive polymer composition. The obtained conductive polymer composition is extruded tubularly while it is being heated to a required temperature. It is possible to perform the dynamic crosslinking at a front half of a biaxial extruder and feed the polymeric-type antistatic agent to a portion of the biaxial extruder halfway between the front half thereof and the rear half thereof to mix the polymeric-type antistatic agent with the other components at the rear half thereof. Thereby it is possible to improve productivity and save the energy necessary for the production.

The polymeric-type antistatic agent consisting of the polymeric-type charge prevention agent and the anion-containing salt having the fluoro group and the sulfonyl group are kneaded in advance to form a master batch.

The conductive roller 1 is formed from the antistatic polymer composition having antistatic properties of the third invention, described in claim 9, of the second invention relating to the conductive and antistatic polymer composition containing the polymeric-type antistatic agent of the first invention. Therefore the conductive roller 1 has rubberlike durability, elasticity, and flexibility; resinlike moldability; and excellent antistatic properties. Further the conductive roller 1 does not generate toxic gases in discarding it. That is, it does not pollute environment. Further because the conductive roller is thermoplastic, it can be recycled. Because the electric characteristic of the conductive roller is adjusted without using carbon black, the conductive polymer composition can be colored easily.

Figure 2:
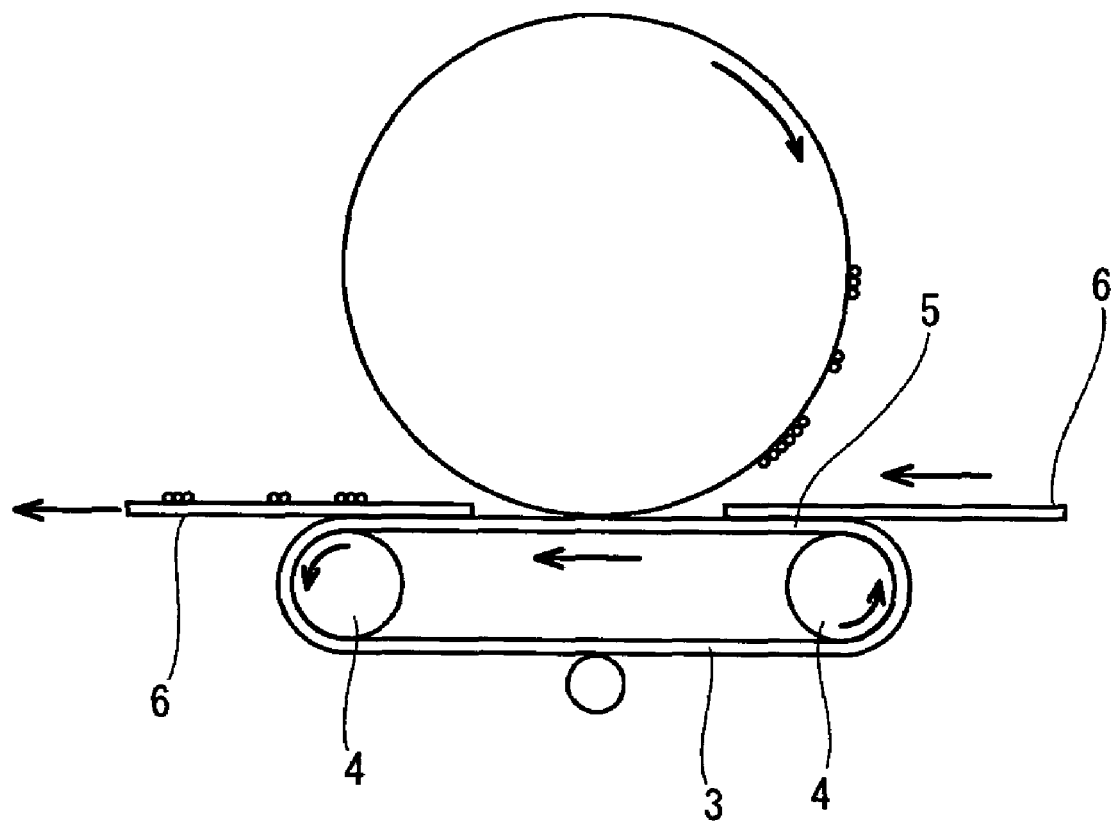
FIG. 2 is a schematic view showing a conductive belt formed by molding the conductive polymer composition of the present invention.

As shown in FIG. 2, a conductive belt 3 such as a transfer belt may be formed from the conductive polymer composition by using a resin extruder or the like. The conductive belt 3 is tight-stretched by two or more pulleys 4. The conductive belt 3 serves as a means for delivering a sheet 6 such as paper and a toner image by movably holding it on a straight portion 5 thereof disposed at its upper side. The conductive belt 3 transfers a toner image formed on a photosensitive member to paper.

In addition to the first embodiment, the polymeric-type antistatic agent can be used by mixing it with at least one polymer material selected from among a thermoplastic polymer, a thermoplastic elastomer, and an unvulcanized rubber. As the main component of the polymer composition forming the polymeric-type antistatic agent of the first invention, it is possible to use known copolymers such as a polyoxyalkylene copolymer. In addition to the above-described polymeric-type charge prevention agent, it is possible to use a resin or/and an elastomer having a polar group for the polymer composition.

As described above, as the anion-containing salt having the fluoro group and the sulfonyl group, it is possible to use an alkali metal salt of tris (trifluoromethanesulfonyl) methide and an alkali metal salt of trifluoromethanesulfonic acid. As the anion having the fluoro group and the sulfonyl group, it is possible to use the anions shown by the above-described chemical formulas 1 through 3. Above all, it is possible to use at least one anion selected from among bis (fluoroalkylsulfonyl) imide ion, tris (fluoroalkylsulfonyl) methide ion, and fluoroalkylsulfonic acid ion. In addition, it is possible to form various salts by combining these anions with cations of any one of alkali metals, group 2A metals, transition metals, amphoteric metals, and those shown by the chemical formulas 4 and 5.

In addition to the above-described TPV, various kinds of thermoplastic elastomers can be used. As the crosslinkable component, the above-described crosslinkable thermoplastic elastomer composition and rubbers can be used. The kind of the styrene thermoplastic elastomer and that of the olefin resin may be altered appropriately. Further the kind and amount of each of the components of the conductive polymer composition can be set appropriately.

In addition to the conductive roller, the conductive belt, the paper-feeding roller, the paper-feeding belt, and the driving roller for office appliances, the following products can be formed from the polymer composition: parts of electronic apparatuses, apparatuses for manufacturing electronic parts, parts of household appliances, parts of office appliances, communication apparatuses, housing parts, parts of optical apparatus appliances, parts of vehicles, building materials, floor materials, tires, hoses, packing films, packing materials, sealing materials, gloves, and synthesized leather.

The examples of the polymer composition of the second invention and the third invention having antistatic properties and the comparison examples are described in detail below.

In the examples 1 through 3 and the comparison examples 1 through 6, paper-feeding rollers composed of the conductive polymer composition were evaluated.

In the examples 4 and the comparison examples 1, 6 through 8, conductive rollers composed of the conductive polymer composition were evaluated.

In the examples 5 through 7 and the comparison examples 9 through 15, IC trays (flat and lattice-shaped tray used to transport, store or heat-treating IC packages which are semiconductive electronic parts in manufacturing process thereof) composed of the conductive polymer composition were evaluated.

By using the materials shown in tables 1 and 2 and a method (will be described in detail later) similar to that of the first embodiment, a roller for an office appliance and a slab sheet for evaluating properties of the conductive polymer composition were prepared in the example 1.

TABLE 1

|  | E1 | E2 | E3 | E4 | E5 | E6 | E7 |
| --- | --- | --- | --- | --- | --- | --- | --- |
| Styrene TPV | 100 | 100 | 100 | 100 |  |  |  |
| Olefin resin |  |  |  |  | 100 | 100 |  |
| Hydrogenated styrene TPE2 |  |  |  |  |  |  | 100 |

TABLE 1-continued

|  | E1 | E2 | E3 | E4 | E5 | E6 | E7 |
|---|---|---|---|---|---|---|---|
| Polymeric-type antistatic agent 1 | 3.0 | 6.0 | 3.0 | 18 | 10.0 | | |
| Salt 1 | 0.16 | 0.060 | 0.16 | 0.94 | 0.53 | | |
| Anion adsorbent 1 | | | 0.031 | | | | |
| Ethylene oxide-propylene oxide copolymer | | | | | | 10 | 10 |
| Salt 1 | | | | | | 0.53 | 0.53 |
| Amount of anion-containing salt having fluoro group and sulfonyl group | 5.3 | 1.0 | 5.3 | 5.3 | 5.3 | 5.3 | 5.3 |
| Volume resistivity $\log_{10} \rho v \Omega \cdot$ cm(normal temperature and humidity) | 9.9 | 9.2 | 9.6 | 7.5 | 10.6 | 11.4 | 10.2 |
| Surface resistivity $\log_{10} \rho s\, \Omega$ (normal temperature and humidity) | 10.1 | 9.6 | 9.8 | 7.8 | 9.9 | 10.6 | 9.5 |
| Volume resistivity $\log_{10} \rho v \Omega \cdot$ cm(low temperature and humidity) | 11.0 | 10.2 | 10.7 | 8.0 | 11.6 | 11.9 | 10.8 |
| Surface resistivity $\log_{10} \rho s \Omega$ (low temperature and humidity) | 11.0 | 11.0 | 10.7 | 8.9 | 10.8 | 11.3 | 10.2 |
| $\Delta\log_{10} \rho v\, \Omega \cdot$ cm((low temperature and humidity) - (normal temperature and humidity) | 1.1 | 1.0 | 1.1 | 0.5 | 1.1 | 0.5 | 0.6 |
| $\Delta\log_{10} \rho s\, \Omega$ ((low temperature and humidity) - (normal temperature and humidity)) | 0.9 | 1.4 | 0.9 | 1.1 | 0.9 | 0.7 | 0.7 |
| Hardness | 46 | 48 | 46 | 54 | — | — | — |
| Compression set | 18 | 22 | 18 | 25 | — | — | — |
| Test of examining whether photosensitive member has been stained | ○ | ○ | ○ | ○ | — | — | — |
| Blooming/breeding | ○ | ○ | ○ | ○ | ○ | ○ | ○ |
| Moldability | ○ | ○ | ○ | ○ | ○ | ○ | ○ |
| Reusableness | ○ | ○ | ○ | ○ | ○ | ○ | ○ |
| Circumferential nonuniformity | — | — | — | 1.2 | — | — | — |
| Operational suitability test of transfer roller | — | — | — | ○ | — | — | — |
| Test for evaluating printing made by paper-feeding roller | ○ | ○ | ○ | — | — | — | — |
| Colorability | | | | | ○ | ○ | ○ |
| Cost | | | | | ○ | ○ | ○ |
| | Paper supply | Paper supply | Paper supply | Electric conduction | IC tray | IC tray | IC tray | where E denotes example.

TABLE 2

|  | CE1 | CE2 | CE3 | CE4 | CE5 |
|---|---|---|---|---|---|
| Styrene TPV | 100 | 100 | 100 | 100 | 100 |
| Olefin resin | | | | | |
| Hydrogenated styrene TPE2 | | | | | |
| Ionic conductivity TPE | | | | | |
| Polymeric-type antistatic agent 1 | | | 3.0 | 5.0 | |
| Ethylene oxide-propylene oxide copolymer | | | | | |
| Polymeric-type antistatic agent 2 | | | | | 3.0 |
| Carbon | | | | | 9.0 |
| Amount of anion-containing salt having fluoro group and sulfonyl group | 0.0 | 0.0 | 0.0 | 0.0 | 0.0 |
| Volume resistivity $\log_{10} \rho v \Omega \cdot$ cm(normal temperature and humidity) | 15.6 | 13.9 | 10.1 | 12.6 | 9.9 |
| Surface resistivity $\log_{10} \rho s\, \Omega$ (normal temperature and humidity) | 15.0 | 13.3 | 10.3 | 12.1 | 9.5 |
| Volume resistivity $\log_{10} \rho v \Omega \cdot$ cm(low temperature and humidity) | 17.1 | 15.6 | 12.1 | 13.4 | 10.5 |
| Surface resistivity $\log_{10} \rho s \Omega$ (low temperature and humidity) | 16.7 | 15.2 | 12.3 | 12.8 | 10.1 |
| $\Delta \log_{10} \rho v\, \Omega \cdot$ cm((low temperature and humidity) - (normal temperature and humidity)) | 1.5 | 1.8 | 2.0 | 0.8 | 0.6 |
| $\Delta \log_{10} \rho s\, \Omega$ ((low temperature and humidity) - (normal temperature and humidity)) | 1.7 | 1.9 | 2.0 | 0.6 | 0.6 |
| Hardness | 46 | 46 | 51 | 47 | 54 |
| Compression set | 16 | 19 | 27 | 17 | 22 |
| Blooming/breeding | ○ | ○ | ○ | ○ | ○ |
| Test of examining whether photosensitive member has been stained | ○ | ○ | ○ | ○ | ○ |
| Moldability | ○ | ○ | ○ | ○ | ○ |
| Reusableness | ○ | ○ | ○ | ○ | ○ |
| Circumferential nonuniformity | 1.2 | — | — | — | — |
| Operational suitability test of transfer roller | ○ | — | — | — | — |
| Test for evaluating printing made by paper-feeding roller | x | x | Δ | x | ○ |
| | Paper supply and electric conduction | Paper supply | Paper supply | Paper supply | Paper supply |

|  | CE6 | CE7 | CE8 | CE9 | CE10 |
|---|---|---|---|---|---|
| Styrene TPV | | 100 | 100 | | |
| Olefin resin | | | | 100 | 100 |
| Hydrogenated styrene TPE2 | | | | | |
| Ionic conductivity TPE | 100 | | | | |

TABLE 2-continued

| | | | | | |
|---|---|---|---|---|---|
| Polymeric-type antistatic agent 1 Ethylene oxide-propylene oxide copolymer | | | 18 | | 10 |
| Polymeric-type antistatic agent 2 | | | | | |
| Carbon | | | | 4.5 | |
| Amount of anion-containing salt having fluoro group and sulfonyl group | 0.0 | 0.0 | 0.0 | 0.0 | 0.0 |
| Volume resistivity $\log_{10} \rho v \Omega \cdot$ cm (normal temperature and humidity) | 9.3 | 10.2 | 8.9 | 15.7 | 13.6 |
| Surface resistivity $\log_{10} \rho s \Omega$ (normal temperature and humidity) | 8.5 | 10.1 | 8.4 | 14.7 | 13.0 |
| Volume resistivity $\log_{10} \rho v \Omega \cdot$ cm (low temperature and humidity) | 9.8 | 12.1 | 9.0 | 17.3 | 15.8 |
| Surface resistivity $\log_{10} \rho s \Omega$ (low temperature and humidity) | 9.1 | 11.9 | 8.5 | 16.9 | 15.4 |
| $\Delta \log_{10} \rho v \Omega \cdot$ cm ((low temperature and humidity) - (normal temperature and humidity)) | 0.5 | 1.9 | 0.1 | 1.6 | 2.3 |
| $\Delta \log_{10} \rho s \Omega$ ((low temperature and humidity) - (normal temperature and humidity)) | 0.5 | 1.8 | 0.1 | 2.2 | 2.4 |
| Hardness | 27 | 55 | 49 | — | — |
| Compression set | 50 | 31 | 23 | — | — |
| Blooming/breeding | x | o | o | o | o |
| Test of examining whether photosensitive member has been stained | x | o | o | — | — |
| Moldability | o | o | Δ | o | o |
| Reusableness | o | o | o | o | o |
| Circumferential nonuniformity | 1.2 | 1.2 | 2.6 | — | — |
| Operational suitability test of transfer roller | x (Photosensitive member was stained) | x | Δ | — | — |
| Test for evaluating printing made by paper-feeding roller | x (Paper was stained) | — | — | — | — |
| Colorability | | | | o | o |
| Cost | | | | o | o |
| | Paper supply and electric conduction | Electric conduction | Electric conduction | IC tray | IC tray |

| | CE11 | CE12 | CE13 | CE14 | CE15 |
|---|---|---|---|---|---|
| Styrene TPV | | | | | |
| Olefin resin | 100 | 100 | | | |
| Hydrogenated styrene TPE2 | | | 100 | 100 | 100 |
| Ionic conductivity TPE | | | | | |
| Polymeric-type antistatic agent 1 Ethylene oxide-propylene oxide copolymer | | | | 10 | |
| Polymeric-type antistatic agent 2 | 10 | 22 | | | |
| Carbon | | | | | 12 |
| Amount of anion-containing salt having fluoro group and sulfonyl group | 0.0 | 0.0 | 0.0 | 0.0 | 0.0 |
| Volume resistivity $\log_{10} \rho v \Omega \cdot$ cm (normal temperature and humidity) | 12.8 | 10.2 | 15.9 | 15.6 | 10.5 |
| Surface resistivity $\log_{10} \rho s \Omega$ (normal temperature and humidity) | 12.2 | 10.0 | 15.5 | 14.8 | 10.1 |
| Volume resistivity $\log_{10} \rho v \Omega \cdot$ cm (low temperature and humidity) | 13.6 | 11.0 | 16.9 | 16.6 | 10.6 |
| Surface resistivity $\log_{10} \rho s \Omega$ (low temperature and humidity) | 13.2 | 10.7 | 16.5 | 16.0 | 10.2 |
| $\Delta \log_{10} \rho v \Omega \cdot$ cm ((low temperature and humidity) - (normal temperature and humidity)) | 0.8 | 0.8 | 0.9 | 1.0 | 0.1 |
| $\Delta \log_{10} \rho s \Omega$ ((low temperature and humidity) - (normal temperature and humidity)) | 1.0 | 0.8 | 1.0 | 1.2 | 0.1 |
| Hardness | — | — | — | — | — |
| Compression set | — | — | — | — | — |
| Blooming/breeding | o | o | o | o | o |
| Test of examining whether photosensitive member has been stained | — | — | — | — | — |
| Moldability | o | o | o | o | o |
| Reusableness | o | o | o | o | o |
| Circumferential nonuniformity | — | — | — | — | — |
| Operational suitability test of transfer roller | — | — | — | — | — |
| Test for evaluating printing made by paper-feeding roller | — | — | — | — | — |
| | o | o | o | o | x |
| | o | x | o | o | x |
| | IC tray | IC tray | IC tray | IC tray | IC tray | where CE denotes comparison example.

In tables 1 and 2, the numerical values showing amounts of the components are parts by weight. "The amount of the anion-containing salt having the fluoro group and the sulfonyl group" is shown by part by weight for 100 parts by weight of the polymeric-type charge prevention agent or 100 parts by weight of the thermoplastic resin or/and the elastomer having the polar group specified by claim 1 or 3. The detail of the components, used for the conductive polymer composition, shown in tables 1 and 2 is as follows:

Styrene TPV: consisting of the following components in table 3.

Olefin resin: polypropylene, "Novatech PP BC6" produced by Nippon Polychem Inc.

Hydrogenated styrene TPE2: SEEPS, styrene content: 65 wt %, "Septon" produced by Kuraray Co., Ltd.

Ionic-conductive TPE: thermoplastic elastomer composition containing chlorine and ester plasticizer, "Elastage ES2801A" produced by Toso.

Polymeric-type charge prevention agent 1: polyether-polyolefin block copolymer, "Pelestat 300" produced by Sanyo Kasei Kogyo Inc.

Salt 1: lithium-bis (trifluoromethanesulfonyl) imide. The salt 1 was used by dispersing it in the polymeric-type charge prevention agent 1 or an ethylene oxide-propylene oxide copolymer.

Anion adsorbent 1 (single-ionized): synthesized hydrotalcite "Kyoward-1000" produced by Kyowa Chemical Industry.

Ethylene oxide-propylene oxide copolymer: "Zeospan 8100" produced by Zeon Corporation.

Polymeric-type charge prevention agent 2: A monohydrate of sodium perchlorate was added to a composition consisting of nylon 12 and a polyether block nylon 12 copolymer, IRGASTAT P18 produced by Chiba Specialty Chemicals.

Carbon: "Ketchen Black EC" produced by Ketchen Black International

TABLE 3

| Contents of composition of styrene TPV | |
|---|---|
| Rubber | 65 |
| Hydrogenated styrene TPE1 | 20 |
| Olefin resin | 15 |
| Softener | 100 |
| Crosslinking agent 1 | 2.0 |
| Crosslinking agent 2 | 5.9 |
| Crosslinking activator | 3.3 |

The detail of the components, used for the conductive polymer composition, shown in table 3 is as follows:

Rubber: EPDM, "Esprene 670F" (paraffin oil 100% oil-extended) (content of rubber and amount of oil in oil-extended rubber are shown in column of rubber and column of softener respectively) produced by Sumitomo Chemical Co., Ltd.

Hydrogenated styrene TPE1: SEEPS, "Septon 4077" produced by Kuraray Co., Ltd., styrene content: 30 wt %.

Olefin resin "Novatech PP BC6" produced by Nippon Polychem Inc.

Softener: paraffin oil ("Diana Process Oil PW-380" produced by Idemitsu Kosan Co., Ltd.) (content: 35 parts by weight other than oil contained in oil-extended rubber)

Crosslinking agent 1: "Tacky Roll 250-III" produced by Taoka Chemical Co., Ltd.

Crosslinking agent 2: "Tacky Roll 201" produced by Taoka Chemical Co., Ltd.

Crosslinking activator: Zinc oxide white produced by Mitsui Metal Industries, Ltd.

Evaluation of Paper-Feeding Roller Formed from Conductive Polymer Composition

Formation of Pellet of Styrene TPV

After the styrene thermoplastic elastomer was swollen in a softener, the swelled styrene thermoplastic elastomer and a pellet of the olefin resin were kneaded by using a biaxial extruder at 160° C. to 220° C. for one to 20 minutes to form a pellet of a mixture (compound) of the styrene thermoplastic elastomer, the olefin resin, and the softener. Thereafter the pellet, pelletized rubber (EPDM), a reactive phenol resin serving as a resin crosslinking agent, required additives such as a zinc oxide, an age resistor, and a filler were supplied to the biaxial extruder and were kneaded for one to 20 minutes while they were being heated at 160° C. to 230° C. to dynamically crosslink the rubber. The extruded kneaded composition was cooled to obtain a pellet consisting of the components shown in table 3.

Formation of master batch (polymeric-type antistatic agent of the first invention) consisting of anion-containing salt, having fluoro group and sulfonyl group, added to polymeric-type charge prevention agent or thermoplastic elastomer or/and elastomer having polar group.

After the pellet of the thermoplastic elastomer or/and the elastomer having the polar group and the anion-containing salt having the fluoro group and the sulfonyl group were dry-blended with a Henshell mixer or a tumbling mixer, they were supplied to the biaxial extruder and kneaded for one to 20 minutes while they were being heated at 140° C. to 220° C. The extruded kneaded composition was cooled with water to obtain a pellet of the polymeric-type antistatic agent.

Formation of Antistatic(Conductive) Polymer Composition of Third Invention

After the pellet of the styrene TPV and that of the polymeric-type antistatic agent prepared by the above-described method were dry-blended with the Henshell mixer or the tumbling mixer, they were supplied to the biaxial extruder and kneaded for one to 20 minutes while they were being heated at 140° C. to 220° C. The extruded kneaded composition was cooled with water to obtain a pellet of the antistatic(conductive) polymer composition.

The kneading was all conducted by using the biaxial extruder manufactured by Kobe Seiko Inc. at a rotational speed 200 rpm. Instead, the kneading may be performed with a kneader or a Banbury mixer.

The pellet of the antistatic (conductive) polymer composition, which was obtained in this manner was supplied to a resin extruder to extrude it tubularly while it was being heated at 180° C. to 240° C. The tube was cut to a predetermined size to obtain a paper-feeding roller. The roller had an inner diameter of 31 mm, an outer diameter of 36 mm, and a width of 17 mm.

EXAMPLES 1 THROUGH 4

The styrene TPV was used as the polymer. An anion adsorbent was used in the example 3.

EXAMPLES 5 AND 6

As the polymer, the olefin resin was used instead of the styrene TPV.

EXAMPLE 7

As the polymer, the styrene TPE2 was used instead of the styrene TPV.

The polymer composition of each of the examples was formed as the antistatic(conductive) polymer composition of the present invention. Other components and the amount thereof of each of the examples were set as shown in table 1.

COMPARISON EXAMPLES 1 THROUGH 15

The polymer composition of each of the comparison examples 1 through 15 was formed not as the antistatic (conductive) polymer composition of the present invention. The polymer composition of each of the comparison examples 1 through 15 did not contain the anion-containing salt having the fluoro group and the sulfonyl group. The components and amount thereof of each of the comparison examples 1 through 15 were set as shown in table 2.

Evaluation of the polymer composition of each of the examples and the comparison examples was made on various properties thereof by using methods that will be described later. Tables 1 and 2 show results of the evaluations.

Test for Evaluating Printing

The paper-feeding roller of each of the examples and comparison examples was mounted on an ink jet printer BJ S300 manufactured by Canon to print a specified format. The results of the printing done by using the paper-feeding rollers were evaluated by checking whether ink was uniformly applied to paper. To this end, the surface of paper was observed with a video microscope. If a static electricity is generated by the paper-feeding roller, a uniform image is not formed. The evaluation of the printed results were made at a normal temperature (23° C.) and humidity (relative humidity: 55%) and a low temperature (10° C.) and humidity (relative humidity: 15%).

The lower the electric resistance, the better. It can be said that a region having a surface resistivity not more than $10^{11}(\Omega)$ is effective for preventing the roller from being charged. Thus the roller having the surface resistance value in this region does not cause a nonuniform image to be formed.

O: Nonuniform image was not formed at normal temperature and humidity and also at low temperature and humidity.

Δ: Nonuniform image was not formed at normal temperature and humidity, but nonuniform image was formed at low temperature and humidity.

X: Nonuniform image was formed at normal temperature and humidity.

The pellet of the antistatic polymer composition was molded by using an injection molding machine to form slab sheets of 130 mm×130 mm×2 mm and specimens for measuring compression set specified in JIS described below to evaluate the volume resistivity (volume specific resistance) (Ω·cm), surface resistivity (surface resistance) (Ω), hardness, compression set, whether photosensitive member was stained, and blooming/bleeding.

In a manner described later, evaluations were made on Moldability and whether the slab sheets (specimens) could be recycled.

Evaluation of Conductive Roller (Transfer Roller) Formed from Conductive Polymer Composition The pellet of the conductive polymer composition was supplied to the resin extruder to extrude it tubularly while it was being heated at 180° C. to 240° C. After a metal shaft was inserted into the tube and bonded thereto, the tube was cut to a predetermined size and polished to form a conductive roller (transfer roller) of each of the example 4 and comparison examples 1, 6 through 8 for a laser beam printer of Laser Jet 4050 type produced by Hulet Packard Inc. The rubber part of the conductive roller had an inner diameter of 6 mm, an outer diameter of 14 mm, and a length of 218 mm.

Operational Suitability Test of Transfer Roller

The roller of each of the examples and the comparison examples was set on the laser beam printer to print photographic data and character data.

O: Good images were obtained from the photographic data and the character data.

Δ: Although there was no problem on the formed image of the character data, roughness was observed on the formed image of the photographic data when it was checked with a magnifying glass.

X: roughness was observed on the formed image of the photographic data and the character data because images were bad.

Circumferential Nonuniformity of Electric Resistance

Figure 3:
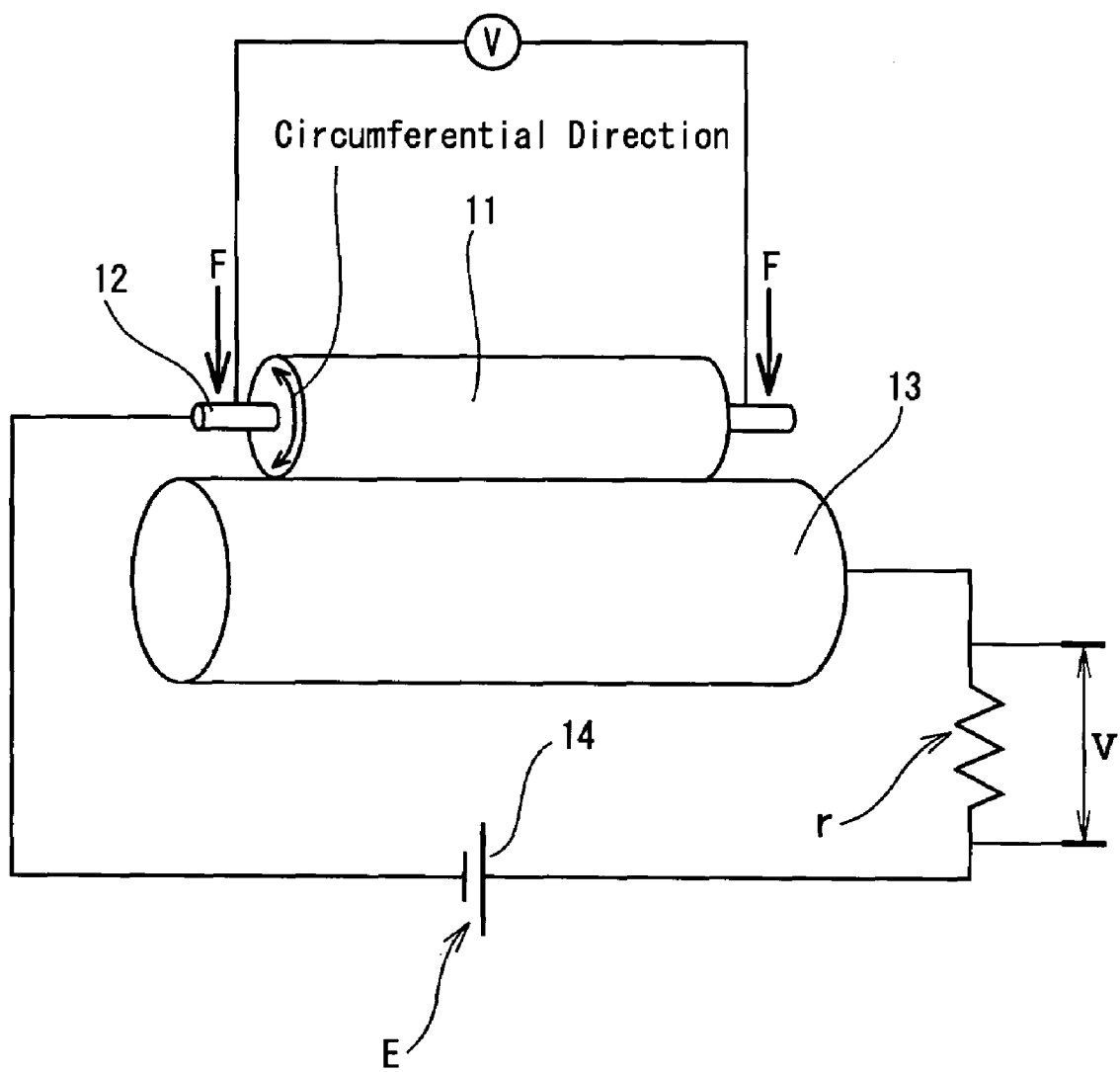
FIG. 3 shows the method of measuring circumferential nonuniformity of the electric resistance of the conductive roller.

As shown in FIG. 3, at a temperature of 23° C. and a relative humidity of 55%, a conductive roller 11 having a metal shaft 12 inserted therethrough was mounted on an aluminum drum 13 having an outer diameter of 30 mmφ, with the conductive roller 11 in contact with the aluminum drum 13. The leading end of a conductor, having an internal electric resistance of r (100Ω to 10Ω), which was connected to the positive side of a power source 14 was connected to one end surface of the aluminum drum 13. The leading end of the conductor connected to the negative side of the power source 14 was connected to one end surface of the metal shaft 12 of the conductive roller 11.

A voltage applied to the internal electric resistance of r was detected. The detected voltage was V. The value of the internal electric resistance r was adjusted in such a way that the significant digits of measured values were as large as possible in conformity to the level of the electric resistance of the conductive roller 11.

Supposing that a voltage applied to the apparatus is E, the electric resistance R of the rubber roller is: $R=r\times E/(V-r)$. Because the term of (−r) is regarded as being slight, $R=r\times E/V$.

A load F of 500 g was applied to both ends of the metal shaft 12. The aluminum drum 13 was rotated at 30 rpm to rotate the conductive roller. While the conductive roller was rotating, a voltage of E=1 kV was applied between the metal shaft and the aluminum drum to compute circumferential nonuniformity (ratio of maximum electric resistance in circumferential direction to minimum electric resistance in circumferential direction) of the electric resistance of the conductive roller. The value indicating the circumferential nonuniformity is favorably in the range of 1.0 to 1.3 and more favorably in the range of 1.0 to 1.2.

The properties of the conductive polymer composition were evaluated in the form of the solid roller in the examples and the comparison examples. However, the properties of the conductive polymer composition may be evaluated in the form of a foamed roller formed by using known resin-foaming methods. Further the properties of the conductive polymer composition may be evaluated in the form of conductive rollers such as a driving roller, a charging roller, and a developing roller in addition to the transfer roller.

Similarly to the above-described "evaluation of paper-feeding roller formed from conductive polymer composition", slab sheets each having a dimension of 130 mm×130 mm×2 mm and specimens for measuring the compression set of the conductive polymer compositions in accordance with the method specified in JIS were prepared for each of the examples and the comparison examples by using an injection molding machine to evaluate the volume resistivity (volume specific resistance) (Ω·cm), surface resistivity (surface resistance) (Ω), hardness, compression set, stain of photosensitive member, and blooming/bleeding of the conductive polymer composition.

In a manner described below, evaluations were made on moldability and reusableness of the conductive polymer composition.

In the conductive roller of the comparison example 6, a pellet commercially available was purchased. The pellet was supplied to a resin extruder to extrude it tubularly while it was being heated at 150° C. to 180° C. The tube was cut to a predetermined size to obtain a paper-feeding roller or a transfer roller by using a method similar to that described above.

Slab sheets having a dimension of 130 mm×130 mm×2 mm and specimens for measuring the compression set of the conductive polymer compositions in accordance with the method specified in JIS were prepared for each of the examples and the comparison examples in the same manner as that described above by using the injection molding machine.

Evaluation of IC Tray Formed from Antistatic(Conductive) Polymer Composition

The pellet of the antistatic(conductive) polymer composition of the third invention was supplied to an injection molding machine to mold it into an IC tray, while it was being heated at 180° C. to 240° C. The IC tray had a length of 300 mm, a width 150 mm, and a thickness of 6 mm. Fifty (5×10) IC packages can be mounted on the tray. In addition, slab sheets each having a dimension of 130 mm×130 mm×2 mm were prepared in the same manner as that described above by injection molding.

Colorability

The colorability of the IC tray of each of the examples 5 through 7 and the comparison examples 9 through 15 was evaluated on the following basis. The IC tray on which the fundamental colors (red, green, yellow, white, and blue) could be colored by using organic pigments and inorganic pigments was rated as passable (O), whereas the IC tray on which the fundamental colors could not be colored was rated as not passable (X).

Cost

The total of the material cost of each of the examples 5 through 7 and the comparison examples 9 through 15 formed into the IC tray was evaluated on the following basis.

O: less than 2.5 times as high as the cost of the base resin (examples 9 and 13)

X: not less than 2.5 times as high as the cost of the base resin

Hardness

To examine the hardness of the conductive(antistatic) polymer composition of the examples 1 through 4 and the comparison examples 1 through 8 formed into the paper-feeding roller or the conductive roller, the hardness of the above-described permanent compression set-measuring specimens was tested by the durometer of type E in accordance with the requirement of "method of testing hardness of vulcanized rubber and thermoplastic rubber" specified in JIS K6253.

It is preferable that the hardness of the paper-feeding roller is not more than 50 and that the hardness of the conductive roller is not more than 55.

Measurement of Permanent Compression Set

To examine the permanent compression set of the conductive(antistatic) polymer composition of the examples 1 through 4 and the comparison examples 1 through 8 formed into the paper-feeding roller or the conductive roller, the compression set of the above-described compression set-measuring specimens were measured at 70° C. for 22 to 24 hours at a compression rate of 25% in accordance with the requirement of "method of testing permanent strain of vulcanized rubber and thermoplastic rubber" specified in JIS K6262.

Volume Specific Resistance

The volume specific resistance of each of the above-described slab sheets (130 mm×130 mm×2 mm) was measured at 23° C. and a relative humidity of 55% (normal temperature and humidity) and at 10° C. and a relative humidity of 15% (low temperature and humidity) by using an ultrahigh resistance meter R-8340A manufactured by Advantest Corporation. The measuring method conformed to the method of measuring the volume resistivity (volume specific resistance) specified in JIS K6911. The applied voltage was 1000V. Tables show the volume specific resistance of each slab sheet by common logarithm $\log_{10}\rho_v$ ($\Omega$·cm). The difference $\Delta \log_{10}\rho_v$($\Omega$·cm) between the common logarithm at the low temperature and humidity and the common logarithm at the normal temperature and humidity, namely, $\log_{10}\rho_v$(10° C., relative humidity: 15%)–$\log_{10}\rho_v$(23° C., relative humidity: 55%) was also computed. The results are shown in tables.

Surface Resistivity

The volume resistivity of each of the above-described slab sheets (130 mm×130 mm×2 mm) was measured at 23° C. and a relative humidity of 55% (normal temperature and humidity) and at 10° C. and a relative humidity of 15% (low temperature and humidity) by using an ultrahigh resistance meter R-8340A manufactured by Advantest Corporation. The measuring method conformed to the method of measuring the volume resistivity (volume specific resistance) specified in JIS K6911. The applied voltage was 1000V. Tables show the volume specific resistance of each slab sheet by common logarithm $\log_{10}\rho_s\Omega$·cm. The difference $\Delta \log_{10}\rho_s\Omega$·cm between the common logarithm at the low temperature and humidity and the common logarithm at the normal temperature and humidity, namely, $\log_{10}\rho_s$(10° C., relative humidity: 15%)–$\log_{10}\rho_s$(23° C., relative humidity: 55%) was also computed. The results are shown in tables.

Test of Examining Whether Photosensitive Member was Stained

Whether the conductive(antistatic) polymer composition of each of the examples 1 through 4 and the comparison examples 1 through 8 formed into the paper-feeding roller or the conductive roller stained a photosensitive member was examined by the following method:

Slab sheets were stored for one week at 32.5° C. and at a relative humidity of 90%, with the slab sheets pressed against a photosensitive member set in a cartridge (cartridge type C4127X) of a laser beam printer of Laser Jet 4050 type produced by Hewlett-Packard Company. After each slab sheet was removed from the photosensitive member, half-tone printing was carried out by the laser beam printer accommodating the photosensitive member. Whether or not sheets of paper on which the half-tone printing was carried out had been stained was checked visually to make evaluations by the following three criteria:

O: On printed paper no stain was observed with the naked eye.

Δ: Low degree of stain (After 5 or less sheets of paper were printed, stains on the paper were hardly observed and thus there is no problem in use).

X: High degree of stain (After not less than 5 sheets of paper were printed, stains on the paper could be still recognized with the naked eye).

Blooming and Bleeding

After the slab sheets were left at the normal temperature and humidity (temperature: 23° C. and at relative humidity: 55%) for one week, the surfaces thereof were checked with the naked eye to check whether blooming or bleeding occurred.

O: Blooming nor bleeding occurred.

X: Blooming or bleeding occurred.

Moldability

The pellet of the composition of each of the examples 1 through 4 and the comparison examples 1 through 8 was molded by an extruder to evaluate the moldability thereof on the following basis.

O: Good extruded surface was obtained.

Δ: Bad extruded surface was obtained. Unless the extrusion speed was reduced to such an extent (not more than 1 cm/second) that productivity could not be secured, the pellet could not be molded preferably.

X: Extrusion molding could not be accomplished.

The moldability of the conductive polymer composition of each of the examples 5 through 7 and the comparison examples 9 through 14 was evaluated on the IC tray formed by molding each pellet by an injection molding machine on the following basis.

O: Good extruded surface was obtained.

Δ: Although molding could be made, the surface of the IC tray was rough.

X: The IC tray could not be formed by the injection molding.

Evaluation of Whether Conductive Polymer Composition can be Recycled

After the metal shaft or the metal shaft of each of the paper-feeding rollers and the transfer rollers prepared as described above was removed therefrom, the polymer composition having the antistatic properties was pulverized by a pulverizer. Each IC tray was cut to fragments by the pulverizer after stain of the surface thereof was removed.

The fragments of the conductive polymer composition obtained in this manner were supplied to the resin extruder or the injection molding machine to form the paper-feeding roller, the transfer roller, and the IC tray in the above-described manner. Whether these rollers formed in this manner could be recycled was checked. The rollers that could be recycled were rated as good (O). The rollers that could not be recycled were was rated as bad (X).

As shown in table 1, the conductive polymer composition of each of the example 1 through 7 had sufficient antistatic properties and electrically conductive and showed preferable values in the properties thereof. The performance of the conductive polymer composition of each of the example 1 through 3 was evaluated highly in the printing test. It was confirmed that they were suitable as the paper-feeding roller. The conductive polymer composition of the example 4 had good results in the operational suitability test of transfer roller. The conductive polymer composition of each of the examples 5 through 7 was excellent in colorability. Further the material cost thereof was appropriate. Thus it was confirmed that they were suitable for products such as the IC tray requiring antistatic performance. It was also confirmed that the conductive polymer composition is capable of securing antistatic performance sufficiently by adding a small amount of the polymeric-type antistatic agent to a large amount of the polyolefin (examples 5,6), a large amount of the styrene resin (example 7) or a large amount of the elastomer resin containing the elastomer containing the polyolefin or the styrene resin, although the conventional art is incapable of dosing so.

On the other hand, as shown in table 2, the conductive polymer composition of each of the comparison examples 1, 2, and 4 had a high electric resistance respectively. Thus they cannot be put to practical use. The conductive polymer composition of the comparison example 3 had a high electric resistance at the low temperature and humidity. Thus each of the paper-feeding rollers formed from the conductive polymer composition and was rated low in the printing test. The conductive polymer composition of the comparison example 3 had a comparatively high hardness. Thus it cannot be put to practical use. The conductive polymer composition of the comparison example 5 had a low electric resistance but had a high hardness. That is, it did not have values indicating preferable properties. The paper-feeding roller having this hardness has a low friction coefficient and is hence inadequate in feeding paper. The conductive roller formed from the conductive polymer composition of the comparison example 6 had bleeding and a high compression set and stained the photosensitive member. Thus it cannot be put to practical use. Another problem of the conductive polymer composition of the comparison example 6 is that it contained chlorine and phthalic ester.

The conductive roller formed from the conductive polymer composition of the comparison example 7 had a high electric resistance (volume resistivity) and hardness. Thus a preferable image was not formed by the use of the conductive roller. The conductive polymer composition had a comparatively high compression set. The conductive polymer composition of the comparison example 8 has a large variation (circumferential nonuniformity on roller) in its electric resistance. The moldability of the conductive polymer composition was not good. The conductive polymer composition of each of the comparison examples 9, 10, 11, 13, and 14 had a high electric resistance. Although the conductive polymer composition of the comparison example 12 had a proper electric resistance, it had a high cost. The conductive polymer composition of the comparison example could not be colored. An integrated circuit could be seen through the IC tray from the conductive polymer composition.

An embodiment of the polymer composition of the fourth invention having antistatic properties (electric conduction) will be described below.

The polymer composition of the fourth invention having antistatic properties contains a polymer having a cyano group as an elastomer having a polar group; and not less than 0.01 parts by weight nor more than 20 parts by weight of a salt, having at least one kind of anions, selected from among the above-described chemical formulas 1 through 3, which is added to the polymer without the intermediary of a medium such as a low molecular weight polyether-containing compound or a low-molecular-weight polar compound not fixed by crosslinking and having a number-average molecular weight not more than 5000 (weight-average molecular weight is not more than 10000).

More specifically, as the polymer having the cyano group, 100 parts by weight of low-nitrile acrylonitrile-butadiene rubber is used. The conductive polymer composition contains no other polymer components. As the anion-containing salt, 1 part by weight of lithium-bis (trifluoromethanesulfonyl) imide which is a salt having anions of bis (fluoroalkyl-sulfonyl) imide is used.

The conductive polymer composition contains the following components used for 100 parts by weight of the acrylonitrile-butadiene rubber: 1.5 parts by weight of a vulcanizing agent (sulfur), 1.5 parts by weight of vulcanizing accelerator 1 (dibenzothiazolyl disulfide), 0.5 parts by weight of a vulcanizing accelerator 2 (tetramethylthiuram monosulfide), 20 parts by weight of an inorganic filler (light calcium carbonate), 5 parts by weight of zinc oxide, and 1 part by weight of stearic acid.

The anion-containing salt is mixed with the acrylonitrile-butadiene rubber to form a master batch. The master batch contains 10 wt % of the anion-containing salt. By using the master batch, the antistatic (conductive) polymer composition of the fourth invention having a desired concentration (1 part by weight for 100 parts by weight of entire polymer component) is obtained.

That is, the acrylonitrile-butadiene rubber, the master batch, the vulcanizing agent, the vulcanizing accelerator, the vulcanizing accelerator, the inorganic filler, the zinc oxide, and the stearic acid are fused, kneaded, and vulcanized by using a known rubber kneader such as an enclosed kneader. Thereby the polymer composition can be used as the conductive roller, the conductive belt, rubber products, and the like.

For example, the kneaded material is preformed tubularly by using a single-axis extruder. Then the preform is vulcanized at 160° C. for 10 to 70 minutes. Thereafter a metal shaft to which a hot-melt adhesive agent has been applied is inserted into the tubular preform. Then the tubular preform is bonded to the metal shaft by heating it. After the surface of the rubber into which the metal shaft has been inserted is polished, the rubber is cut to a predetermined size to obtain a conductive roller. The obtained conductive roller having the shaft inserted therethrough is cylindrical and has a configuration similar to that of the conductive roller shown in FIG. 1.

The obtained conductive roller has an appropriately low volume resistivity, does not have bleeding or blooming, does not stain the photosensitive member, and has a low compression set and hardness. Therefore the conductive roller has a dimensional stability and is durable.

In the embodiment of the fourth invention, the conductive polymer composition is formed into the conductive roller to be used as the transfer roller. The conductive polymer composition can be formed into the conductive roller to be used as a charging roller, a developing roller, and a toner supply roller. The conductive polymer composition may be formed into the conductive roller to be used as a foamed roller by adding blowing agents to the polymer component of the conductive polymer composition.

It is also possible to form a conductive belt such as a transfer belt from the conductive polymer composition of the embodiment of the fourth invention. As shown in FIG. 2, the conductive belt can be used as the conductive belt 3 of the embodiment of the third invention.

Figure 4:
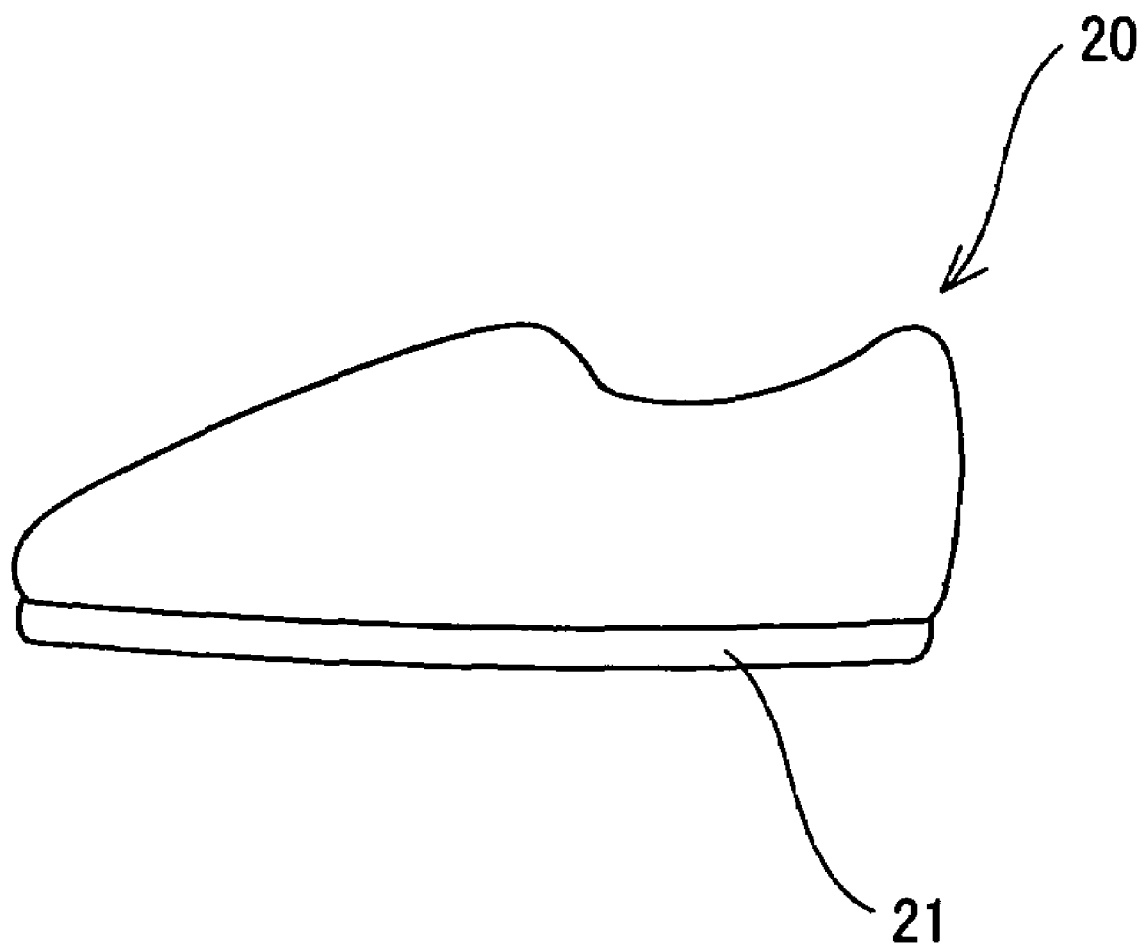
FIG. 4 is a schematic view showing a shoe sole formed by molding the conductive polymer composition of the present invention.

FIG. 4 shows a shoe 20 having a sole 21 formed by molding the polymer composition of an embodiment of the fourth invention. As shown in FIG. 4, the sheet-shaped sole 21 has the same configuration as that of the bottom surface of the shoe 20 and is disposed to cover the area of the shoe 20 that contacts the ground. It is necessary that the sole 21 is disposed at least one portion of the bottom surface of the shoe 20. As the method of vulcanizing and molding the conductive polymer composition, press molding or molding by using an injection molding machine for rubber is normally adopted. But other methods may be used. It is preferable that the polymer composition contains vinyl chloride (PVC) or a mixture of NBR and PVC commercially available to improve the weatherability of the sole 21.

The antistatic polymer composition of the fourth invention may be formed as an adhesive agent by dissolving the polymer composition in a solvent of ketone (for example, acetone) or ester (for example, DOP) and add a phenol resin, an age resistor, and a filler to the solvent as necessary. In this case, a solvent adhesive agent is formed. In the case where a surface active agent, a vulcanizing agent, an age resistor, and a filler are added to latex, a solvent-based adhesive agent is formed. By carrying out these methods, nitrile rubber adhesive agent is formed.

Figure 5:
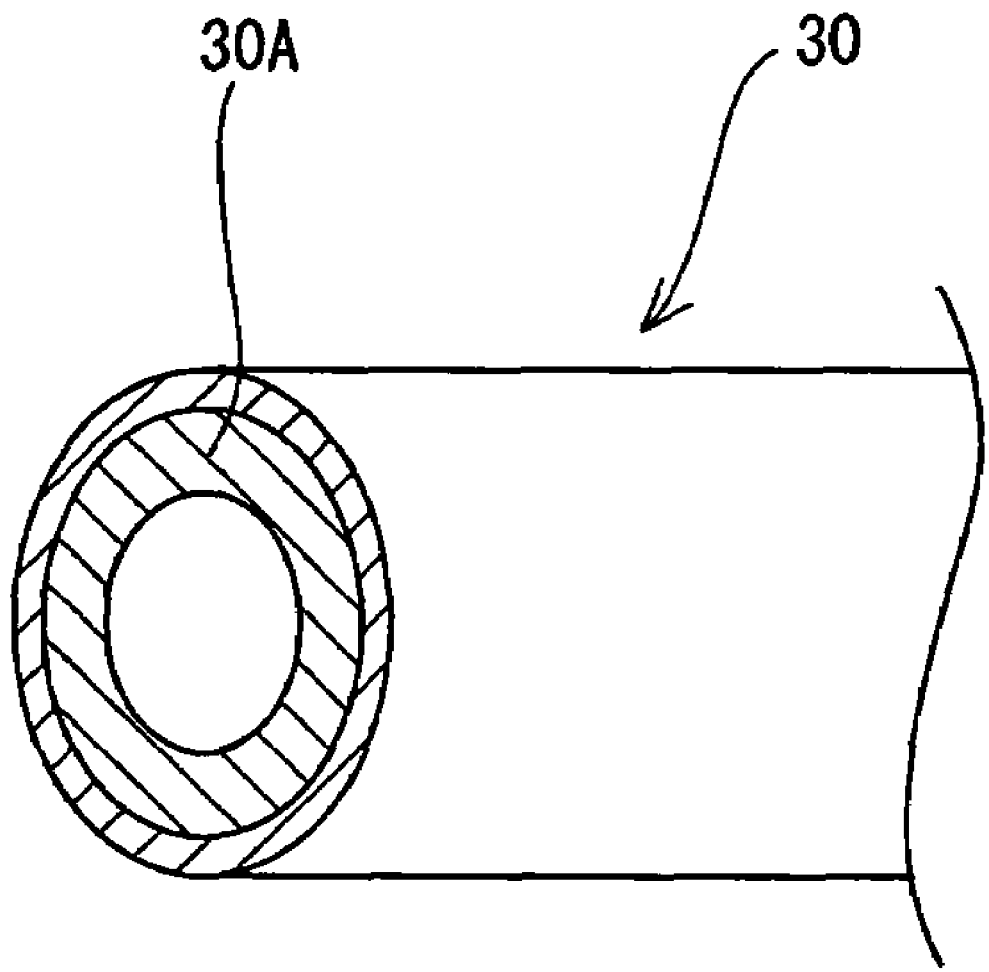
FIG. 5 is a schematic view showing a hose formed by molding the conductive polymer composition of the present invention.

FIG. 5 shows a hose 30 formed from the antistatic polymer composition of an embodiment of the fourth invention. As shown in FIG. 5, the antistatic (conductive) polymer composition of the fourth invention is used as an innermost layer 30A of the hose 30 having a multi-layer construction. The hose 30 can be used preferably as fuel hoses for vehicles and oil-resistant hoses. The hose 30 can be used as acid-resistant and alkali-resistant hoses in various forms. As in the case of the sole 21 of the shoe 20, it is preferable that the polymer composition for the hose 30 contains vinyl chloride (PVC) or a mixture of NBR and PVC commercially available to improve the weatherability of the hose 30. To secure resistance to oil, fuels, and chemicals, it is also preferable that the polymer composition for the hose 30 contains NBR of moderate-high nitrile, high nitrile or extremely high nitrile as the polymer having the cyano group.

Figure 6:
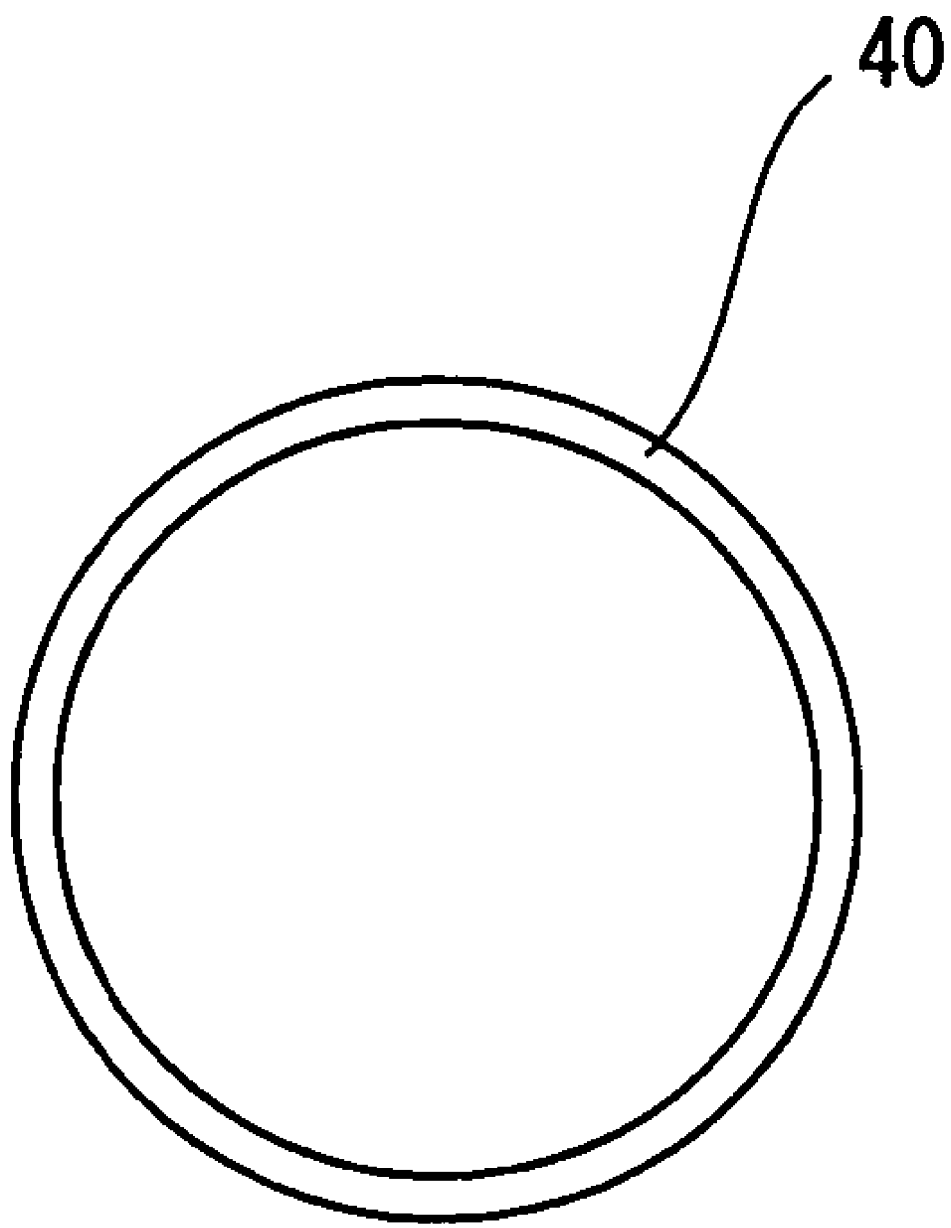
FIG. 6 is a schematic view showing an oil seal formed by molding the conductive polymer composition of the present invention.

FIG. 6 shows an oil seal formed from the antistatic polymer composition of the fourth invention. The oil seal is formed as an annular O-ring 40. The oil seal is used mainly at the rotary portion of industrial machines to prevent lubricating oil and the like from leaking to the outside. Similarly to the O-ring 40, the annular oil seal can be used as packing for enhancing sealing performance. The configuration and size of the oil seal can be set appropriately. As in the case of the sole 21 and the hose 30, it is preferable that the polymer composition for the oil seal contains vinyl chloride (PVC) to improve the weatherability of the oil seal. To secure resistance to oil, it is also preferable that the polymer composition for the oil seal contains NBR of moderate-high nitrile, high nitrile or extremely high nitrile as the polymer having the cyano group.

Figure 7A:
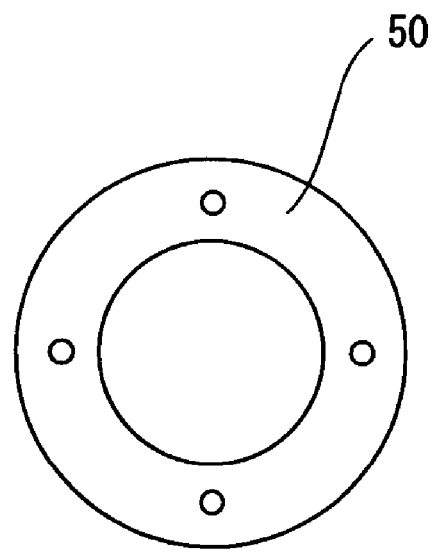
FIG. 7A is a schematic view showing a gasket formed by molding the conductive polymer composition of the present invention.

FIG. 7A shows a gasket 50 formed from the antistatic polymer composition of the fourth invention. The gasket 50 is annular and thin to use it as a seal at a joining portion of apparatuses used at high temperature and pressure or low temperature and pressure.

Figure 7B:
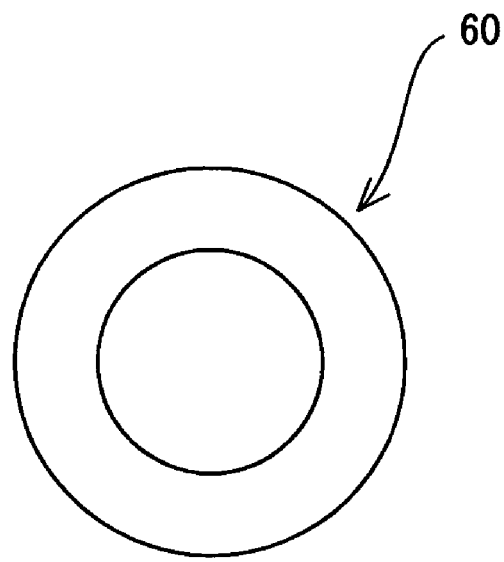
FIG. 7B is a schematic view showing a diaphragm formed by molding the conductive polymer composition of the present invention.

FIG. 7B shows a diaphragm 60 formed from the antistatic polymer composition of the fourth invention. The diaphragm 60 is approximately disk-shaped and used for vehicles, control apparatuses, household appliances, and household electric appliances.

In addition, the conductive polymer composition of the fourth invention can be formed into fiber-processing rollers, textile rollers, gloves, printing rollers, printing blankets, and the like.

In addition to the above-described polymer, as the polymer having the cyano group, it is possible to use hydrogenated acrylonitrile-butadiene rubber, carboxyl-modified acrylonitrile-butadiene rubber, acrylonitrile butadiene-isoprene copolymer rubber (NBIR), liquid nitrile rubber, and one or more latices of these polymers. In addition, it is also preferable to use NBR of intermediate, moderate-high, high or extremely high nitrile. The polymer composition of the fourth invention may contain other polymers.

As the anion-containing salt, it is possible to use salts having tris (fluoroalkylsulfonyl) methide ion, fluoroalkylsulfonic acid ion, and the like or use a mixture of these substances. The anion-containing salt may be used not as a master batch but by adding it to other components.

The examples of the fourth invention and the comparison examples are described below in detail.

The materials having the components shown in tables 4 and 5 were used for examples 8 through 18 and the comparison examples 16 through 21. Conductive rollers, property-evaluating slab sheets, and hardness-measuring specimens were prepared.

The components of the conductive polymer composition of each of the examples and the comparison examples were kneaded at the mixing amounts shown in tables 4 and 5 by an enclosed kneader.

Each of the lithium-bis (trifluoromethanesulfonyl) imide, the lithium trifluoromethanesulfonate, the lithium-tris (trifluoromethanesulfonyl) methide, and quaternary ammonium salt of perchloric acid A-902 was mixed with acrylonitrile-butadiene rubber in advance to form a master batch respectively containing 10 wt % of each of these salts. The conductive polymer composition of each of the examples and the comparison examples was prepared by using these master batches respectively. In the case of the salt whose mixing amount exceeded 2 parts by weight, the conductive polymer composition was prepared by adding a necessary amount of the salt to the polymer without using the master batch. The master batch also contained 1 part by weight of stearic acid and 20 parts by weight of light calcium carbonate for 100 parts by weight of the rubber contained in the master batch. Thereby preferable processability could be obtained when the each salt was added to the acrylonitrile-butadiene rubber. In kneading the master batch, other additives, and remaining NBR, the amount of the stearic acid and that of the light calcium carbonate of the master batch were not counted. It made the composition shown in tables 4 and 5 as a whole. In the example 18, a necessary amount of an anion adsorbent was contained in the master batch. By using the master batch, the conductive polymer composition of the example 18 shown in table 4 was obtained. The amount of the stearic acid and that of the soft calcium were the same as those of the other examples.

Each conductive polymer composition taken out of the kneader as a ribbon was supplied to an extruder of 60 mmφ whose temperature was adjusted to 40° C. to extrude it tubularly. After the obtained raw rubber tube was cut to a predetermined size, it was vulcanized at a predetermined temperature to obtain a vulcanized rubber rube. In the examples and the comparison examples, the vulcanizing temperature and the vulcanizing time period were set to 160° C. and 10 to 70 minutes respectively. The vulcanizing condition was adjusted appropriately with reference to the data of $t_{95}$(minutes) of a Curelastometer.

After a hot-melt adhesive agent is applied to a shaft having the same configuration as that of the transfer roller mounted on a laser beam printer of Laser Jet 4050 type produced by Hulet Packard Inc., the shaft was inserted into the obtained vulcanized rubber tube and bonded thereto by heating them. The surface of the rubber was polished to obtain the roller having a target dimension. The roller had an outer diameter of 14 mmφ, an inner diameter (shaft diameter) of 6 mmφ, and an axial length of 218 mm. The roller had the same dimension as that of the transfer roller mounted on the laser beam printer of Laser Jet 4050 type produced by Hulet Packard Inc.

Rubber taken out as a ribbon from a kneader was extruded by a roller head extruder so that the rubber was sheet-shaped. After it was put in a die to press-vulcanize it at 160° C. for an optimum period of time to obtain slab sheets for evaluating properties and hardness-measuring specimens.

The conductive polymer composition taken out as a ribbon from the kneader was supplied to the extruder to extrude it in the shape of an endless belt. Thereafter it was put in a vulcanizing to vulcanize it at 160° C. for 10 to 70 minutes. Then the surface of the vulcanized conductive polymer composition was polished to obtain a conductive belt having a thickness of 0.50±0.05 mm.

TABLE 4

| Ingredients | Detail of ingredients (name(=commercial name) & maker) | | E8 | E9 | E10 |
|---|---|---|---|---|---|
| Acrylonitrile butadiene rubber 1 | Nipol DN401LL | Zeon Corporation | 100 | 100 | 100 |
| Acrylonitrile butadiene rubber 2 | Nipol DN223 | Zeon Corporation | | | |
| Inorganic filler 1 | Light calcium carbonate | Maruo Calcium Co., Ltd. | 20 | 20 | 20 |
| Zinc oxide | Zinc oxide white | Mitsui Metal Industries, Ltd. | 5 | 5 | 5 |
| Stearic acid | 4931 | Uniqema Australia | 1 | 1 | 1 |
| Lithium-bis (trifluoromethanesulfonyl) imide | | | 1 | 2 | 5 |
| Lithium trifluoromethanesulfonate | | | | | |
| Lithium tris(trifluoromethanesulfonyl) methide | | | | | |
| Anion adsorbent | Kyoward 1000 | Kyowa Chemical Industry | | | |
| Vulcanizing agent 1 | Powdered sulfur | Tsurumi Kagaku Kogyo | 1.5 | 1.5 | 1.5 |
| Vulcanizing accelerator 1 | Nocceler DM | Ouchishinko Chemical Industrial Co., Ltd. | 1.5 | 1.5 | 1.5 |
| Vulcanizing accelerator 2 | Nocceler TS | Ouchishinko Chemical Industrial Co., Ltd. | 0.5 | 0.5 | 0.5 |
| Hardness (compression-caused increase point or decrease point is given in parentheses) | | | 43(−1) | 42(−2) | 44(±0) |
| Volume resistivity $\log_{10} \rho v \Omega \cdot$ cm (normal condition) | | | 8.1 | 7.9 | 7.4 |
| Volume resistivity $\log_{10} \rho v \Omega \cdot$ cm (low temperature and humidity) | | | 8.6 | 8.2 | 7.9 |
| Degree of dependence of volume resistivity on environment $\Delta \log_{10} \rho v \: \Omega \cdot$ cm | | | 0.7 | 0.5 | 0.5 |
| Test of examining whether photosensitive member has been stained | | | ○ | ○ | ○ |
| Blooming/breeding | | | Did not occur | Did not occur | Did not occur |
| Content (wt %) of chlorine or bromine | | | 0.00 | 0.00 | 0.00 |

TABLE 4-continued

| Ingredients | Detail of ingredients (name=commercial name) & maker | | E11 | E12 | E13 |
|---|---|---|---|---|---|
| Acrylonitrile butadiene rubber 1 | Nipol DN401LL | Zeon Corporation | 100 | 100 | |
| Acrylonitrile butadiene rubber 2 | Nipol DN223 | Zeon Corporation | | | 100 |
| Inorganic filler 1 | Light calcium carbonate | Maruo Calcium Co., Ltd. | 20 | 20 | 20 |
| Zinc oxide | Zinc oxide white | Mitsui Metal Industries, Ltd. | 5 | 5 | 5 |
| Stearic acid | 4931 | Uniqema Australia | 1 | 1 | 1 |
| Lithium-bis(trifluoromethanesulfonyl) imide | | | 10 | 0.25 | 1 |
| Lithium trifluoromethanasulfonate | | | | | |
| Lithium tris(trifluoromethanesulfonyl) methide | | | | | |
| Anion adsorbent | Kyoward 1000 | Kyowa Chemical Industry | | | |
| Vulcanizing agent 1 | Powdered sulfur | Tsurumi Kagaku Kogyo | 1.5 | 1.5 | 1.5 |
| Vulcanizing accelerator 1 | Nocceler DM | Ouchishinko Chemical Industrial Co., Ltd. | 1.5 | 1.5 | 1.5 |
| Vulcanizing accelerator 2 | Nocceler TS | Ouchishinko Chemical Industrial Co., Ltd. | 0.5 | 0.5 | 0.5 |
| Hardness (compression-caused increase point or decrease point is given in parentheses) | | | 43(−1) | 43(−1) | 33(−2) |
| Volume resistivity $\log_{10} \rho v \Omega \cdot cm$ (normal condition) | | | 7.2 | 8.7 | 7.9 |
| Volume resistivity $\log_{10} \rho v \Omega \cdot cm$ (low temperature and humidity) | | | 7.8 | 9.2 | 8.5 |
| Degree of dependence of volume resistivity on environment $\Delta \log_{10} \rho v \Omega \cdot cm$ | | | 0.7 | 0.9 | 0.9 |
| Test of examining whether photosensitive member has been stained | | | ○ | ○ | ○ |
| Blooming/breeding | | | Did not occur | Did not occur | Did not occur |
| Content (wt %) of chlorine or bromine | | | 0.00 | 0.00 | 0.00 |

| Ingredients | Detail of ingredients (name=commercial name) & maker | | E14 | E15 | E16 |
|---|---|---|---|---|---|
| Acrylonitrile butadiene rubber 1 | Nipol DN401LL | Zeon Corporation | | | 100 |
| Acrylonitrile butadiene rubber 2 | Nipol DN223 | Zeon Corporation | 100 | 100 | |
| Inorganic filler 1 | Light calcium carbonate | Maruo Calcium Co., Ltd. | 20 | 20 | 20 |
| Zinc oxide | Zinc oxide white | Mitsui Metal Industries, Ltd. | 5 | 5 | 5 |
| Stearic acid | 4931 | Uniqema Australia | 1 | 1 | 1 |
| Lithium-bis(trifluoromethanesulfonyl) imide | | | 5 | 10 | |
| Lithium trifluoromethanesulfonate | | | | | |
| Lithium tris(trifluoromethanesulfonyl) methide | | | | | 1 |
| Anion adsorbent | Kyoward 1000 | Kyowa Chemical Industry | | | |
| Vulcanizing agent 1 | Powdered sulfur | Tsurumi Kagaku Kogyo | 1.5 | 1.5 | 1.5 |
| Vulcanizing accelerator 1 | Nocceler DM | Ouchishinko Chemical Industrial Co., Ltd. | 1.5 | 1.5 | 1.5 |
| Vulcanizing accelerator 2 | Nocceler TS | Ouchishinko Chemical Industrial Co., Ltd. | 0.5 | 0.5 | 0.5 |
| Hardness (compression-caused increase point or decrease point is given in parentheses) | | | 32(−3) | 34(−1) | 43(−1) |
| Volume resistivity $\log_{10} \rho v \Omega \cdot cm$ (normal condition) | | | 7.3 | 7.0 | 7.9 |
| Volume resistivity $\log_{10} \rho v \Omega \cdot cm$ (low temperature and humidity) | | | 7.7 | 7.5 | 8.3 |
| Degree of dependence of volume resistivity on environment $\Delta \log_{10} \rho v \Omega \cdot cm$ | | | 0.6 | 0.7 | 0.6 |
| Test of examining whether photosensitive member has been stained | | | ○ | ○ | ○ |
| Blooming/breeding | | | Did not occur | Did not occur | Did not occur |
| Content (wt %) of chlorine or bromine | | | 0.00 | 0.00 | 0.00 |

| Ingredients | Detail of ingredients (name=commercial name) & maker | | E17 | E18 |
|---|---|---|---|---|
| Acrylonitrile butadiene rubber 1 | Nipol DN401LL | Zeon Corporation | 100 | 100 |
| Acrylonitrile butadiene rubber 2 | Nipol DN223 | Zeon Corporation | | |
| Inorganic filler 1 | Light calcium carbonate | Maruo Calcium Co., Ltd. | 20 | 20 |
| Zinc oxide | Zinc oxide white | Mitsui Metal Industries, Ltd. | 5 | 5 |
| Stearic acid | 4931 | Uniqema Australia | 1 | 1 |
| Lithium-bis(trifluoromethanesulfonyl) imide | | | | |
| Lithium trifluoromethanesulfonate | | | 1 | 1 |
| Lithium tris(trifluoromethanesulfonyl) methide | | | | |
| Anion adsorbent | Kyoward 1000 | Kyowa Chemical Industry | | 0.2 |
| Vulcanizing agent 1 | Powdered sulfur | Tsurumi Kagaku Kogyo | 1.5 | 1.5 |
| Vulcanizing accelerator 1 | Nocceler DM | Ouchishinko Chemical Industrial Co., Ltd. | 1.5 | 1.5 |

TABLE 4-continued

| | | | | |
|---|---|---|---|---|
| Vulcanizing accelerator 2 | Nocceler TS | Ouchishinko Chemical Industrial Co., Ltd. | 0.5 | 0.5 |
| Hardness (compression-caused increase point or decrease point is given in parentheses) | | | 44(±0) | 44(±0) |
| Volume resistivity $\log_{10} \rho v \Omega \cdot cm$ (normal condition) | | | 8.6 | 8.3 |
| Volume resistivity $\log_{10} \rho v \Omega \cdot cm$ (low temperature and humidity) | | | 9.1 | 8.8 |
| Degree of dependence of volume resistivity on environment $\Delta \log_{10} \rho v \Omega \cdot cm$ | | | 0.9 | 0.9 |
| Test of examining whether photosensitive member has been stained | | | ○ | ○ |
| Blooming/breeding | | | Did not occur | Did not occur |
| Content (wt %) of chlorine or bromine | | | 0.00 | 0.00 | where E denotes example.

TABLE 5

| Ingredients | Detail of ingredients (name=commercial name) & maker | | CE16 | CE17 |
|---|---|---|---|---|
| Acrylonitrile butadiene rubber 1 | Nipol DN401LL | Zeon Corporation | 100 | |
| Acrylonitrile butadiene rubber 2 | Nipol DN223 | Zeon Corporation | | 100 |
| Inorganic filler 1 | Light calcium carbonate | Maruo Calcium Co., Ltd. | 20 | 20 |
| Zinc oxide | Zinc oxide white | Mitsui Metal Industries, Ltd. | 5 | 5 |
| Stearic acid | 4931 | Uniqema Australia | 1 | 1 |
| Quaternary ammonium salt not containing chlorine | KP4729 | Kao Corporation | | |
| Quaternary ammonium salt of perchloric acid | A-902 | Japan Carlit Co., Ltd. | | |
| High-performance ionic-conductive plasticizer | | | | |
| Vulcanizing agent 1 | Powdered sulfur | Tsurumi Kagaku Kogyo | 1.5 | 1.5 |
| Vulcanizing accelerator 1 | Nocceler DM | Ouchishinko Chemical Industrial Co., Ltd. | 1.5 | 1.5 |
| Vulcanizing accelerator 2 | Nocceler TS | Ouchishinko Chemical Industrial Co., Ltd. | 0.5 | 0.5 |
| Hardness | | | 44(±0) | 35(±0) |
| Volume resistivity $\log_{10} \rho v \Omega \cdot cm$ (normal condition) | | | 10.1 | 9.5 |
| Volume resistivity $\log_{10} \rho v \Omega \cdot cm$ (low temperature and humidity) | | | 10.7 | 10.4 |
| Degree of dependence of volume resistivity on environment $\Delta \log_{10} \rho v \Omega \cdot cm$ | | | 1.2 | 1.6 |
| Test of examining whether photosensitive member has been stained | | | ○ | ○ |
| Blooming/breeding | | | Did not occur | Did not occur |
| Content (wt %) of chlorine or bromine | | | 0.00 | 0.00 |

| Ingredients | Detail of ingredients (name=commercial name) & maker | | CE18 | CE19 |
|---|---|---|---|---|
| Acrylonitrile butadiene rubber 1 | Nipol DN401LL | Zeon Corporation | 100 | 100 |
| Acrylonitrile butadiene rubber 2 | Nipol DN223 | Zeon Corporation | | |
| Inorganic filler 1 | Light calcium carbonate | Maruo Calcium Co., Ltd. | 20 | 20 |
| Zinc oxide | Zinc oxide white | Mitsui Metal Industries, Ltd. | 5 | 5 |
| Stearic acid | 4931 | Uniqema Australia | 1 | 1 |
| Quaternary ammonium salt not containing chlorine | KP4729 | Kao Corporation | 10 | |
| Quaternary ammonium salt of perchloric acid | A-902 | Japan Carlit Co., Ltd. | | 2 |
| High-performance ionic-conductive plasticizer | | | | |
| Vulcanizing agent 1 | Powdered sulfur | Tsurumi Kagaku Kogyo | 1.5 | 1.5 |
| Vulcanizing accelerator 1 | Nocceler DM | Ouchishinko Chemical Industrial Co., Ltd. | 1.5 | 1.5 |
| Vulcanizing accelerator 2 | Nocceler TS | Ouchishinko Chemical Industrial Co., Ltd. | 0.5 | 0.5 |
| Hardness | | | 46(+2) | 45(+1) |
| Volume resistivity $\log_{10} \rho v \Omega \cdot cm$ (normal condition) | | | 9.2 | 9.1 |
| Volume resistivity $\log_{10} \rho v \Omega \cdot cm$ (low temperature and humidity) | | | 10.0 | 9.8 |
| Degree of dependence of volume resistivity on environment $\Delta \log_{10} \rho v \Omega \cdot cm$ | | | 1.5 | 1.1 |
| Test of examining whether photosensitive member has been stained | | | x | ○ |
| Blooming/breeding | | | Bleeding occurred | Did not occur |
| Content (wt %) of chlorine or bromine | | | 0.00 | 0.16 |

| Ingredients | Detail of ingredients (name=commercial name) & maker | | CE20 | CE21 |
|---|---|---|---|---|
| Acrylonitrile butadiene rubber 1 | Nipol DN401LL | Zeon Corporation | 100 | 100 |
| Acrylonitrile butadiene rubber 2 | Nipol DN223 | Zeon Corporation | | |
| Inorganic filler 1 | Light calcium carbonate | Maruo Calcium Co., Ltd. | 20 | 20 |
| Zinc oxide | Zinc oxide white | Mitsui Metal Industries, Ltd. | 5 | 5 |
| Stearic acid | 4931 | Uniqema Australia | 1 | 1 |
| Quaternary ammonium salt not containing chlorine | KP4729 | Kao Corporation | | |
| Quaternary ammonium salt of perchloric acid | A-902 | Japan Carlit Co., Ltd. | | |
| High-performance ionic-conductive plasticizer | | | 5 | 10 |
| Vulcanizing agent 1 | Powdered sulfur | Tsurumi Kagaku Kogyo | 1.5 | 1.5 |
| Vulcanizing accelerator 1 | Nocceler DM | Ouchishinko Chemical Industrial Co., Ltd. | 1.5 | 1.5 |
| Vulcanizing accelerator 2 | Nocceler TS | Ouchishinko Chemical Industrial Co., Ltd. | 0.5 | 0.5 |
| Hardness | | | 38(−6) | 34(−10) |

TABLE 5-continued

| | | |
|---|---|---|
| Volume resistivity $\log_{10} \rho v \Omega \cdot cm$ (normal condition) | 7.8 | 7.5 |
| Volume resistivity $\log_{10} \rho v \Omega \cdot cm$ (low temperature and humidity) | 8.2 | 7.8 |
| Degree of dependence of volume resistivity on environment $\Delta \log_{10} \rho v \Omega \cdot cm$ | 0.6 | 0.7 |
| Test of examining whether photosensitive member has been stained | x | x |
| Blooming/breeding | Bleeding occurred | Bleeding occurred to high extent |
| Content (wt %) of chlorine or bromine | 0.00 | 0.00 | where CE denotes comparison example.

In tables 4 and 5, the numerical values showing the amount of the components are parts by weight.

In tables 4 and 5, acrylonitrile-butadiene rubber 1 is low-nitrile NBR in which the content (central value) of acrylonitrile was 18.0%. Acrylonitrile-butadiene rubber 2 is moderate-high nitrile NBR in which the content (central value) of the acrylonitrile was 31.5%. Liquid NBR was added to high-molecular weight NBR at the rate of 50 phr to form the acrylonitrile-butadiene rubber 2.

The following anion-containing salts were added to the acrylonitrile-butadiene rubber without the intermediary of the medium such as the low molecular weight polyether-containing compound or the low-molecular-weight polar compound not fixed by crosslinking and having the number-average molecular weight not more than 5000 (weight-average molecular weight is not more than 10000):

lithium-bis (trifluoromethanesulfonyl) imide: $((CF_3SO_2)_2NLi)$, lithium trifluoromethanesulfonate: $((CF_3SO_3)_2Li)$, and lithium-tris (trifluoromethanesulfonyl) methide $((CF_3SO_2)_3CLi)$.

The lithium-bis (trifluoromethanesulfonyl) imide is also used as the salt 1 as shown in table 1. The lithium-bis (trifluoromethanesulfonyl) imide was synthesized by using a known method of allowing reaction of perfluoroalkylsulfonyl halide with an alkali metal salt of N-trimethylsilylperfluoroalkylsulfonyl imide.

The known method is disclosed in Japanese Patent Publication No. 1-38781, Japanese Patent Application Laid-Open No. 9-173856, Japanese Registered Patent No. 3117369, Japanese Patent Application Laid-Open No. 11-209338, Japanese Patent Application Laid-Open No. 2000-86617, Japanese Patent Application Laid-Open No. 2001-139540, and Japanese Patent Application Laid-Open No. 2001-288193.

The lithium trifluoromethanesulfonate was synthesized by using a known method such as an electrolytic fluorinating method of dissolving alkyl sulfonic acid in hydrogen fluoride anhydride and replacing hydrogen of the alkyl chain with fluorine by performing electrolysis.

The known method is disclosed in Japanese Patent Application Laid-Open No. 5-339768 and Japanese Patent Application Laid-Open No. 2001-322975.

The lithium-tris (trifluoromethanesulfonyl) methide was synthesized by using a known method of synthesizing bis (perfluoroalkylsulfonyl) methane by reaction of methylmagnesium halide (Grignard reagent) with perfluoroalkylsulfonyl halide, then reacting the bis (perfluoroalkylsulfonyl) methane with the Grignard reagent and the perfluoroalkylsulfonyl halide to form tris (perfluoroalkylsulfonyl) methane, and thereafter reacting the tris (perfluoroalkylsulfonyl) methane with an alkali metal compound.

The known method is disclosed in U.S. Pat. No. 5,554,664, Japanese Patent Application Laid-Open No. 200-219692, and Japanese Patent Application Laid-Open No. 2000-226392.

As the quaternary ammonium salt not containing chlorine, "KP-4729" (salt of glucono-lactone) which is a quaternary ammonium salt not containing halogen was used. As the quaternary ammonium salt of perchloric acid, trimethylalkylammonium perchlorate (trade name: A-902) was used.

As the vulcanizing accelerator 1, dibenzothiazolyl disulfide was used. As the vulcanizing accelerator 2, tetramethylthiuram monosulfide was used.

EXAMPLES 8 THROUGH 18

As shown in table 4, the conductive polymer composition of each the examples 8 through 12 and 16 through 18 contained 0.25 to 10 parts by weight of the anion-containing salt added to 100 parts by weight of low-nitrile NBR without the intermediary of the medium, not fixed by crosslinking, such as the low-molecular-weight polyether-containing compound or the low-molecular-weight polar compound whose number-average molecular weight is not more than 5000 (weight-average molecular weight is not more than 10000). As the anion-containing salt, the lithium-bis (trifluoromethanesulfonyl) imide, the lithium trifluoromethanesulfonate or the lithium-tris (trifluoromethanesulfonyl) methide was used. The conductive polymer composition of the example 18 contained synthesized hydrotalcite (Kyoward 1000 produced by Kyowa Chemical Industry) as an anion adsorbent.

The antistatic(conductive) polymer composition of each the examples 13 through 15 contained 1 to 10 parts by weight of the anion-containing salt added to 100 parts by weight of the moderate-high NBR which was formed by adding liquid NBR to high-molecular-weight NBR at the rate of 50 phr. The anion-containing salt was added to the moderate-high NBR without the intermediary of the medium, not fixed by crosslinking, such as the low-molecular-weight polyether-containing compound or the low-molecular-weight polar compound whose number-average molecular weight is not more than 5000 (weight-average molecular weight is not more than 10000). As the anion-containing salt, the lithium-bis (trifluoromethanesulfonyl) imide was used.

COMPARISON EXAMPLES 16 THROUGH 21

The polymer composition of each of the comparison examples 16 through 21 indicated in table 5 was different from the antistatic(conductive) polymer of the present invention. The anion-containing salt was not used for the polymer composition of the comparison examples 16 and 17. The anion-containing salt was not used for the polymer composition of the comparison example 18 but the quaternary ammonium salt not containing chlorine was used therefor. The anion-containing salt was not used for the polymer composition of the comparison example 19 but the quaternary ammonium salt of perchloric acid was used therefor. The polymer composition of each of the comparison examples 20 and 21 contained the lithium-bis (trifluoromethanesulfonyl) imide as the anion-containing salt by using the dibutoxyethoxyethyl adipate which was the low-molecular-weight polar compound as the medium. More specifically, a high-performance ionic-conductive plasticizer was formed by dissolving 20 wt % of the lithium-bis (trifluoromethanesulfonyl) imide in the dibutoxyethoxyethyl adipate.

By using the conductive polymer composition of each of the examples and the comparison examples formed as described above, a conductive roller, a slab sheet, and a specimen formed from each conductive polymer composition, the properties thereof were measured and evaluations were made for the obtained results.

The method of examining the hardness, whether the photosensitive member was stained, and occurrence of blooming and blooming was carried out in the same method as that described above.

Volume Resistivity

The volume resistivity of each of the above-described slab sheets having a dimension of 130 mm×130 mm×2 mm was measured at 23° C. and a relative humidity of 55% (normal temperature and humidity) by using an ultrahigh resistance meter R-8340A manufactured by Advantest Corporation. The measuring method conformed to the method of measuring the volume resistivity specified in JIS K6911. The applied voltage was 500V. Tables 4 and 5 show the volume resistivity of each slab sheet by common logarithm $\log_{10}\rho_v$ ($\Omega \cdot cm$).

Degree of Dependence of Volume Resistivity on Environment

In addition to the above-described environment, the volume resistivity $\log_{10}\rho_v(\Omega \cdot cm)$ was computed at a constant temperature of 10° C. and a constant relative humidity of 15% and further at a constant temperature of 32.5° C. and a constant relative humidity of 90%. Based on an equation $\Delta \log_{10}\rho_v = \log_{10}\rho_v$(temperature: 10° C., relative humidity: 15%)$-\log_{10}\rho_v$(temperature: 32.5° C., relative humidity: 90%), the degree of dependence of the volume resistivity on environment was computed.

In addition to the above-described common logarithm of the volume resistivity in the normal condition $\log_{10}\rho_v$ ($\Omega \cdot cm$), tables 4 and 5 show the value of the volume resistivity $\log_{10}\rho_v(\Omega \cdot cm)$ at the low temperature of 10° C. and the low relative humidity of 15% and the degree of dependence of the volume resistivity on environment:

$\Delta \log_{10}\rho_v = \log_{10}\rho_v$(temperature: 10° C., relative humidity: 15%)$-\log_{10}\rho_v$(temperature: 32.5° C., relative humidity: 90%).

The volume resistivity at the low temperature and relative humidity is favorably not more than $10^{9.5}(\Omega \cdot cm)$ more favorably not more than $10^{9.0}(\Omega \cdot cm)$, and most not more than favorably $10^{8.5}$ ($\Omega \cdot cm$).

The value of $\Delta \log_{10}\rho_v$ is favorably not more than 1.1, more favorably not more than 1.0, and most favorably not more than 0.8.

Content of Chlorine or Bromine

The content (wt %) of chlorine or bromine of the composition of each of the examples and the comparison examples was computed.

As indicated in table 4, the conductive polymer composition of each of the examples 8 through 18 had a low value of 7.0 to 9.2 in the common logarithm of the volume resistivity thereof at the normal temperature and humidity and at the low temperature and humidity and low values of 0.5 to 0.9 in $\Delta \log_{10}\rho_v = \log_{10}\rho_v$(temperature: 10° C., relative humidity: 15%)$-\log_{10}\rho_v$(temperature: 32.5° C., relative humidity: 90%) indicating the degree of dependence of the volume resistivity on environment. The evaluation on the test of examining whether the photosensitive member was stained was rated as passable O. That is, the conductive polymer composition of each of the examples 8 through 18 did not stain the photosensitive member. The hardness of the conductive polymer compositions was in the range of 32 to 43 degrees. They had very little change in the properties thereof by the addition of the salt to the polymer component.

As described above, it was confirmed that the conductive (antistatic) polymer composition of each of the examples 8 through 18 had excellent characteristics. That is, each conductive polymer composition had a low volume resistivity and degree of dependence of its volume resistivity on environment, did not stain the photosensitive member nor generate blooming and bleeding, had a low hardness, and had very little change in the properties thereof by the addition of the salt to the polymer component.

The volume resistivity of the low-nitrile NBR contained in the conductive (antistatic) polymer composition of each of the examples 8 through 12 and 16 through 18 could be reduced effectively, although it is difficult for the conventional art to reduce the volume resistivity of the low-nitrile NBR. Because the low-nitrile NBR has a low glass transition temperature (Tg), it has a low degree of dependence on environment in its viscoelasticity and electric resistance and shows very favorable characteristics in the neighborhood of the room temperature. Thus the conductive polymer composition of each of the examples 8 through 12 and 16 through 18 is excellent in this respect.

The conductive (antistatic) polymer composition of each of the examples 13 through 15 contains the acrylonitrile-butadiene rubber containing liquid acrylonitrile-butadiene rubber. In the case where the acrylonitrile-butadiene rubber containing the liquid acrylonitrile-butadiene rubber is used, the polymer chain becomes movable. Thus the conductive polymer composition has excellent processability and ion transport efficiency becomes high. Hence the conductive polymer composition has a low volume resistivity. Further the conductive polymer composition can be extruded favorably. Thus it is possible to form a conductive roller and a conductive belt having a smooth surface from the conductive polymer composition of each of the examples 13 through 15. Further owing to the use of the mixture of high-molecular-weight NBR and the liquid NBR for the conductive polymer composition of each of the examples 13 through 15, a photosensitive can be prevented from being stained and the property of the rubber composition can be kept preferably.

The conductive (antistatic) polymer composition of each of the examples 13 through 15 contains the moderate-high nitrile NBR which causes the degree of dependence of the volume resistivity on environment to be high, as shown by the conductive polymer composition of the comparison example 17. However, by using at least one kind of the anion-containing salt selected from among the chemical formulas 1 through 3 for the conductive polymer composition of each of the examples 13 through 15, each conductive polymer composition has improvement over the conventional conductive polymer composition in the degree of dependence of its volume resistivity on environment without deteriorating its properties and the performance of staining the photosensitive member very little.

Since the conductive (antistatic) polymer composition of the example 18 contains the anion adsorbent, a part of ions generated from the anion-containing salt is single-ionized with the anion adsorbent. Thereby the electric conduction of the conductive polymer composition can be stabilized, and the electric conduction of the conductive polymer composition containing a small amount of the salt can be improved. Thus the conductive polymer composition of the example 18 is superior to that of the comparison example 17 because the former has a lower volume resistivity than the latter containing the same components as those of the former except that the latter does not contain the anion adsorbent.

In the conductive polymer composition of each of the examples 8, 9, 12, 13, 16, 17, and 18, the anion-containing salt was mixed with the polymer component to form a master batch which contained the polymer and 10 wt % of the anion-containing salt. The master batch also contains stearic acid serving as a processing aid and light calcium carbonate or the like to be contained in the end polymer composition. Therefore high kneading processability can be obtained. That is, the anion-containing salt can be mixed uniformly with the other components. Since the enclosed kneader is used in forming the master batch, it is possible to secure safety in a kneading operation and knead a large amount of components at a time. Thus the conductive polymer composition can be produced with high efficiency.

The conductive polymer composition of each of the examples 8 through 18 did not contain chlorine or bromine. Thus as shown in table 4, the content of chlorine or bromine was zero in any of the conductive polymer compositions. Therefore toxic gases such as hydrogen chloride and harmful substances such as dioxin are not generated, when the conductive polymer composition is burnt to discard it.

As shown in table 5, the electric resistance of the conductive polymer composition of each of the comparison examples 16 through 19 was not low, especially at the low temperature and humidity, thus the conductive polymer compositions had a problem in the electric conduction and antistatic performance thereof.

The conductive polymer composition of the comparison example 16 had the same components and mixing ratio as those of the examples 8 through 12, 16, and 17 except that the former did not contain the anion-containing salt. The conductive polymer composition of the comparison example 17 had the same components and mixing ratio as those of the examples 13 through 15 except that the conductive polymer composition of the comparison example 12 did not contain the anion-containing salt.

The conductive polymer composition of the comparison example 18 had the same components and mixing ratio as those of the examples 8 through 12, 16, and 17 except that the conductive polymer composition of the comparison example 18 did not contain the anion-containing salt but instead contained the quaternary ammonium salt not containing chlorine. However, the conductive polymer composition of the comparison example 18 generated bleeding and stained the photosensitive member. In addition, the conductive polymer composition of the comparison example 18 had a high volume resistivity at the low temperature and humidity.

The conductive polymer composition of the comparison example 19 had the same components and mixing ratio as those of the examples 8 through 12, 16, and 17 except that the conductive polymer composition of the comparison example 19 did not contain the anion-containing salt but instead contained the quaternary ammonium salt of perchloric acid. However, the conductive polymer composition of the comparison example 19 contained chlorine and stained the photosensitive member to some extent. In addition, the conductive polymer composition of the comparison example 19 had a high volume resistivity at the low temperature and humidity.

The conductive polymer composition of each of the comparison examples 20 and 21 had a sufficiently low volume resistivity, but contained dibutoxyethoxyethyl adipate as the medium for dispersing the anion-containing salt therein. The dibutoxyethoxyethyl adipate is a low-molecular-weight polar compound not fixed by crosslinking and having a number-average molecular weight not more than 5000 (weight-average molecular weight is not more than 10000). Thus the conductive polymer composition of each of the comparison examples 20 and 21 generated bleeding and stained the photosensitive member. Moreover they had a very low hardness owing to the use of the dispersion medium.

Figure 8A:
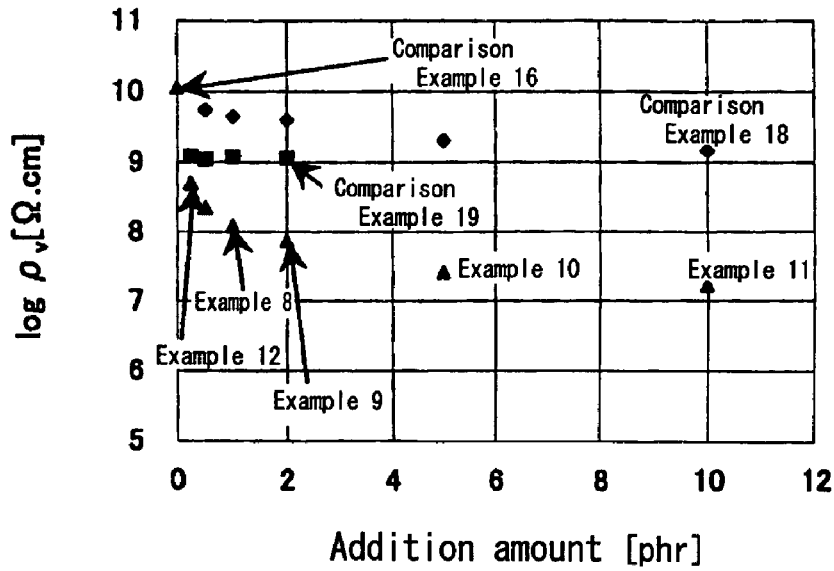
FIG. 8A shows the relationship between addition amounts of salts and volume resistivities in a normal temperature and humidity.
Figure 8B:
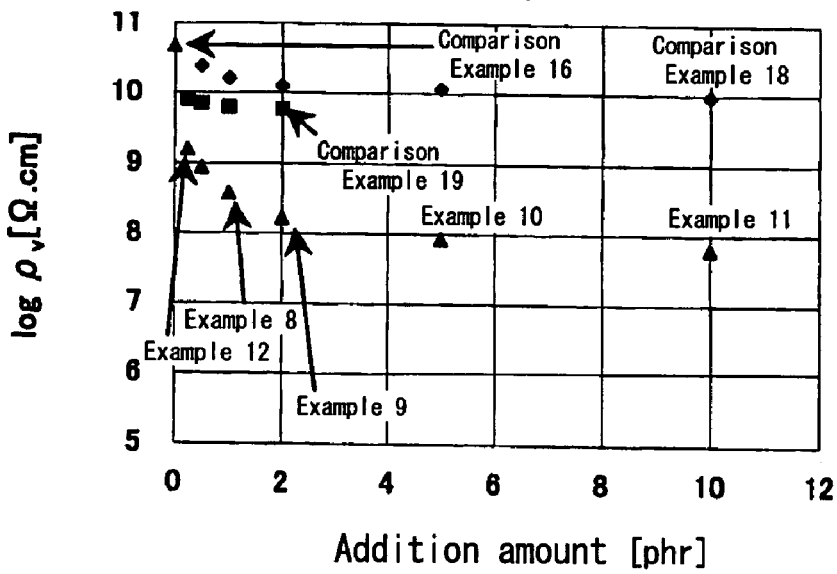
FIG. 8B shows the relationship between addition amounts of salts and volume resistivities at a low temperature and humidity.

The relationship between addition amounts of representative salts and the volume resistivities of the conductive polymer compositions is graphed based on the data of the examples and the comparison examples. In FIG. 8A, the volume resistivities of the conductive polymer compositions in the normal condition (temperature: 23° C., relative humidity: 55%) are graphed. In FIG. 8B, the volume resistivities of the conductive polymer compositions at the low temperature and humidity (temperature: 10° C., relative humidity: 15%) are graphed.

As shown in FIG. 8A, the quaternary ammonium salt of perchloric acid of the comparison example 19 is capable of reducing the volume resistivity of the conductive polymer composition by using a small amount thereof. But the quaternary ammonium salt of perchloric acid is incapable of reducing the volume resistivity, even if the addition amount thereof is increased. The quaternary ammonium salt not containing chlorine of the comparison example 18 has a low degree of performance in reducing the volume resistivity of the conductive polymer composition. Thus it is necessary to use a large amount of the quaternary ammonium salt not containing chlorine. Further the quaternary ammonium salt not containing chlorine is incapable of reducing the volume resistivity sufficiently.

On the other hand, as shown in FIG. 8A, the salts of the examples are capable of reducing the volume resistivities of the conductive polymer compositions greatly by using a small amount thereof. As shown in FIG. 8B, the salts of the examples reduces the degree of dependence of the volume resistivity on environment and the volume resistivity sufficiently at the low temperature and humidity.

In FIGS. 8A and 8B, ▲ indicates the data of the lithium-bis (trifluoromethanesulfonyl) imide (example); ♦ indicates the data of the quaternary ammonium salt not containing chlorine, KP-4729 (comparison example); and ■ indicates the data of the quaternary ammonium salt of perchloric acid A-902 (comparison example).

The embodiments of the fifth invention is described below.

The polymer composition of the fifth invention is molded by heating it at 180° C. to 240° C. with an injection molding machine to form an IC tray as described in the first embodiment. In embodiments, the conductive roller 1 of the first embodiment shown in FIG. 1 and the conductive belt shown in FIG. 2 are formed from the polymer composition.

The polymer composition consists of a mixture of a component (A) consisting of a low-polar polymer composition; a component (B) consisting of the anion-containing salt specified by the above-described chemical formulas 1 through 3 or/and a polymer, containing the anion-containing salt, such as polyether block polyolefin having an ether linkage; and a component (C) consisting of a polymer having an ester structure.

The component (A) consists of polypropylene resin. The component (B) consists of a composition containing 95 parts by weight of the polyether block polyolefin and 5 parts by weight of the lithium-bis (trifluoromethanesulfonyl) imide or potassium-bis (trifluoromethanesulfonyl) imide specified by the chemical formulas 1 through 3. The component (C) consists of vinyl acetate-ethylene copolymer or ethylene-vinyl acetate copolymer or a mixture of these copolymers.

Regarding the mixing ratio among the three components, not less than 0.01 nor more than 20 parts by weight of the component (B), namely, the anion-containing salt specified by the chemical formula 1, not less than 0.05 nor more than 80 parts by weight of the polymer such as polyether block polyolefin having the ether linkage, and not less than one nor more than 40 parts by weight of the polymer of the component (C) are added to 100 parts by weight of the component (A).

A pellet obtained by kneading the three components is molded into IC trays by known molding methods such as an injection molding method or an extrusion molding method. As the component (A), instead of the polypropylene resin, the styrene thermoplastic elastomer dynamically crosslinked (styrene TPV) is molded into the conductive roller 1 shown in FIG. 1 and the conductive belt 3 shown in FIG. 2.

The polymer composition of each of examples 19 through 29 of the embodiment of the fifth invention and that of each of the comparison examples 22, 23, and reference examples 1, 2 were formed as shown in table 6. Sheets each having a thickness of 2 mm, a length of 130 mm, and a width of 130 mm were formed by molding each polymer composition by an injection molding machine. The surface resistivity of each sheet was measured by the following method and evaluated.

TABLE 6

|  | E19 | E20 | E21 | E22 | E23 | E24 | E25 | E26 |
|---|---|---|---|---|---|---|---|---|
| Polypropylene | 100 | 100 | 100 | 100 | 100 | 100 | 100 | 100 |
| Styrene TPV |  |  |  |  |  |  |  |  |
| Composition(*) containing salt having anion shown by chemical formula 1 | 5.26 | 5.26 | 5.26 | 5.26 | 5.26 | 5 26 | 5.26 | 10.53 |
| Ethylene-vinyl acetate copolymer or vinyl acetate-ethylene copolymer |  |  |  |  |  |  |  |  |
| Levapren 400 | 10.00 |  |  |  |  |  |  |  |
| Levapren 600HV |  | 10.00 |  |  |  |  |  |  |
| Levapren 800HV |  |  | 10.00 |  |  | 5.00 | 20.00 | 20.00 |
| Levapren VP KA8815 |  |  |  | 10.00 |  |  |  |  |
| Sumikaflex RP-100S |  |  |  |  | 10.00 |  |  |  |
| Surface resistivity | 12.86 | 11.76 | 10.80 | 12.96 | 12.26 | 12.28 | 10.27 | 9.38 |

|  | E27 | E28 | E29 | CE22 | CE23 | RE1 | RE2 |
|---|---|---|---|---|---|---|---|
| Polypropylene | 100 | 100 |  | 100 |  | 100 |  |
| Styrene TPV |  |  | 100 |  | 100 |  | 100 |
| Composition(*) containing salt having anion shown by chemical formula 1 | 15.79 | 5.26 | 1.79 | — | — | 5.26 | 1.79 |
| Ethylene-vinyl acetate copolymer or vinyl acetate-ethylene copolymer |  |  |  |  |  |  |  |
| Levapren 400 |  |  |  |  |  |  |  |
| Levapren 600HV |  |  |  |  |  |  |  |
| Levapren 800HV | 10.00 | 10.00 | 3.3 |  |  |  |  |
| Levapren VP KA8815 |  |  |  |  |  |  |  |
| Sumikaflex RP-100S |  |  |  |  |  |  |  |
| Surface resistivity | 9.01 | 11.30 | 10.84 | 15.27 | 15.03 | 14.86 | 13.85 | where E denotes example.
where CE denotes comparison example.
where RE denotes reference example.
*In examples 19 through 27, 29, reference example 1, 2, 5 wt % of lithium-bis (trifluoromethanesulfonyl) imide was added to "Pelestat 300" at 150° C. by using a biaxial extruder. A pellet obtained by cooling the mixture was used.
In example 28, 5 wt % of potassium-bis (trifluoromethanesulfonyl) imide was added to "Pelestat 300" at 150° C. by using the biaxial extruder. A pellet obtained by cooling the mixture was used.

EXAMPLE 19

The following substances were added to 100 parts by weight of polypropylene ("Novatech PP BC6 produced by Nippon Polychem.) which is an olefin resin used as the low-polar polymer composition: 5.26 parts by weight of a composition containing 5 parts by weight of polyether block polyolefin ("Pelestat 300" produced by Sanyo Kasei Kogyo) and 0.26 parts by weight of lithium-bis (trifluoromethanesulfonyl) imide and 10 parts by weight of an ethylene-vinyl acetate copolymer ("Lebaprene 400 (content of vinyl acetate: 40 wt %) produced by Bayer Inc.) The components were kneaded by a biaxial extruder (produced by Kobe Seiko Inc.). The obtained pellet was molded by an injection molding machine into a sheet having a thickness of 2 mm, and into an IC tray having a length of 300 mm, a width of 150 mm, and a thickness of 6 mm.

EXAMPLES 20 THROUGH 23

In the example 20, as the vinyl acetate-ethylene copolymer, "Lebaprene 600HV" (content of vinyl acetate: 60 wt %) produced by Bayer Inc. was used. In the example 21, as the vinyl acetate-ethylene copolymer, "Lebaprene 800HV" (content of vinyl acetate: 80 wt %) produced by Bayer Inc. was used. In the example 22, as the vinyl acetate-ethylene acetate copolymer, "Lebaprene VP KA8815" (content of vinyl acetate: 60 wt %, pre-vulcanized grade) produced by Bayer Inc. was used. In the example 23, as the vinyl acetate-ethylene acetate copolymer, "Sumikaflex RP-100S" produced by Sumitomo Chemical Co., Ltd. was used.

Except the kind of the vinyl acetate-ethylene acetate copolymer was different from that of the example 19, the polymer composition of each of the examples 20 through 23 was formed into a sheet and an IC tray in the same method as that used in the example 19.

EXAMPLES 24 THROUGH 27

Except that "Lebaprene 800HV" (content of vinyl acetate: 80 wt %) produced by Bayer Inc. was used as the vinyl acetate-ethylene acetate copolymer and the mixing amount of each component was as shown in table 6, the polymer composition of each of the examples 24 through 27 was formed into a sheet and an IC tray by using the same method as that used in the example 19.

EXAMPLE 28

"Lebaprene 800HV" (content of vinyl acetate: 80 wt %) produced by Bayer Inc. was used as the vinyl acetate-ethylene acetate copolymer. Instead of the composition containing 5 parts by weight of the polyether block polyolefin ("Pelestat 300" produced by Sanyo Kasei Kogyo) and 0.26 parts by weight of the lithium-bis (trifluoromethanesulfonyl) imide, a composition containing 5 parts by weight of the polyether block polyolefin ("Pelestat 300" produced by Sanyo Kasei Kogyo Inc.) and 0.26 parts by weight of the potassium-bis (trifluoromethanesulfonyl) imide added to the polyether block polyolefin was used.

Except the above point, a sheet and an IC tray were from the polymer composition by using the same method as that used in the example 19.

EXAMPLE 29

The following substances were added to 100 parts by weight of styrene TPV, having the components shown in table 7, obtained by performing crosslinking in the above-described method: 1.79 parts by weight of a composition containing 1.7 parts by weight of the "Pelestat 300" and 0.09 parts by weight of the lithium-bis (trifluoromethanesulfonyl) imide and 3.3 parts by weight of "Lebaprene 800HV". The components were kneaded by a biaxial extruder at 200° C. for two minutes. The obtained pellet was molded by an injection molding machine into a sheet having a thickness of 2 mm. A tube for a conductive roller was formed from the pellet by using a resin extruder. The tube was bonded to a metal shaft with an adhesive agent to form the conductive roller. The pellet was cylindrically shaped by using the resin extruder and cut to obtain a conductive belt. The pellet was extruded into the conductive roller and the conductive belt at 210 to 230° C.

TABLE 7

| Contents of composition of styrene TPV | |
|---|---|
| Rubber | 65 |
| Hydrogenated styrene TPE1 | 20 |
| Olefin resin | 15 |
| Softener | 100 |
| Crosslinking agent 1 | 2.0 |
| Crosslinking agent 2 | 5.9 |
| Crosslinking activator | 3.3 |

The detail of the components, used for the conductive polymer composition, shown in table 7 is as follows:

Rubber: EPDM, "Esprene 670F" (paraffin oil 100% oil-extended) (content of rubber and amount of oil in oil-extended rubber are shown in column of rubber and column of softener respectively) produced by Sumitomo Chemical Co., Ltd.

Hydrogenated styrene TPE1: SEEPS, "Septon 4077" produced by Kuraray Co., Ltd., styrene content: 30 wt %

Olefin resin "Novatech PP BC6" produced by Nippon Polychem Inc.

Softener: paraffin oil ("Diana Process Oil PW-380" produced by Idemitsu Kosan Co., Ltd.) (content: 35 parts by weight other than oil contained in oil-extended rubber)

Crosslinking agent 1: "Tacky Roll 250-III" produced by Taoka Chemical Co., Ltd.

Crosslinking agent 2: "Tacky Roll 201" produced by Taoka Chemical Co., Ltd.

Crosslinking activator: Zinc oxide white produced by Mitsui Metal Industries, Ltd.

COMPARISON EXAMPLE 22

An IC tray and a sheet were formed from 100 parts by weight of polypropylene in the same method as that used in the example 19.

REFERENCE EXAMPLE 1

Except that the ethylene-vinyl acetate was not used for the conductive polymer composition, an IC tray and a sheet were formed in the same method as that used in the example 19.

COMPARISON EXAMPLE 23

The styrene TPV was molded in the same method as that used in the example 29.

REFERENCE EXAMPLE 2

Except that the "Lebaprene 800HV" was not used, a polymer composition similar to that of the example 29 was formed. The pellet thereof was molded in the same method as that used in the example 29.

Measurement of Surface Resistivity

The surface resistivity was measured in the same method as that used in the first embodiment.

As apparent from table 6, the surface resistivity of the conductive polymer composition of each of the examples and the comparison examples was larger than $10^{13}\Omega$: The surface resistivity of the comparison example 22, the reference example 1, the comparison example 23, and the reference example 2 were $10^{15.27}\Omega$, $10^{14.86}\Omega$, $10^{15.03}\Omega$ and $10^{13.85}\Omega$ respectively. On the other hand, the conductive polymer composition of each of the examples 19 through 29 was much less than $10^{13}\Omega$. More specifically, the conductive polymer compositions of the examples 19 through 29 had a surface resistivity in the range of $10^{9.01}\Omega$ to $10^{12.96}\Omega$. It was confirmed that the conductive polymer composition of each of the examples 19 through 29 had performance of reducing the surface resistivity.

It could be also confirmed that the present invention provides molded products, the conductive roller, and the conductive belt at low costs because the conductive polymer composition can be provided with a sufficient antistatic performance and a low electric resistance at a low cost by using a small addition amount (1.8 to 5.3 parts by weight) of the anion-containing salt specified by the chemical formulas 1 through 3 and the polymer such as the polyether block polyolefin, having the ether linkage, which is used as the medium for the anion-containing salt.

As shown by the examples of the fifth invention, in adding the polymer having the ester structure to the low-polar polymer to improve the compatibility between the anion-containing salt specified by the chemical formulas 1 through 3 or/and the polymer such as the polyether block polyolefin, having the ether linkage, which is used as the medium for the anion-containing salt, it is possible to reduce the addition amount of the expensive anion-containing salt specified by the chemical formula 1 or/and the polymer such as the polyether block polyolefin, having the ether linkage, which is used as the medium for the anion-containing salt. Thus it is possible to reduce the manufacturing cost of the conductive polymer composition. Further it is possible to prevent the generation of bleeding or blooming because the low-molecular-weight polyether-containing compound or the low-molecular-weight polar compound is not used for the conductive polymer composition. Moreover the conductive (antistatic) polymer composition secures a low permanent compression set and hardness and superior electric conduction. Since carbon black is not used for the conductive polymer composition, the conductive polymer composition is applicable to products that are required to be transparent or colored.

In the case where the thermoplastic elastomer in which the rubber component is dispersed by dynamic crosslinking is used as the low-polar polymer composition, the anion-containing salt specified by the chemical formula 1 or/and the polymer such as the polyether block polyolefin, having the ether linkage, which is used as the medium for the anion-containing salt are hardly mixed with the dynamically crosslinked rubber component and are unevenly distributed mainly in the matrix of the polymer composition. Therefore the crosslinking of the rubber is not adversely affected by the addition of the anion-containing salt and the polymer such as the polyether block polyolefin, having the ether linkage, which is used as the medium for the anion-containing salt. Consequently it is possible to prevent deterioration of the properties (change of hardness, deterioration of permanent compression set, and the like) of the conductive polymer composition containing these components and realize preferable moldability and processability.

Since the materials for products formed from the conductive polymer composition do not contain chlorine, the entire conductive polymer composition does not contain chlorine. Thereby it is possible to prevent a metal surface from being corroded, rusted or stained. Further toxic gases such as hydrogen chloride and harmful substances such as dioxin are generated when the conductive polymer composition is burnt to discard it.

What is claimed is:

1. A polymeric antistatic agent comprising:
a polymer composition containing a polymeric charge prevention agent containing a resin or/and an elastomer as a main component thereof; or/and a thermoplastic resin having a polar group or/and an elastomer having said polar group; wherein said polymer composition contains a polyether block polyolefin copolymer, and
an anion-containing salt, having a fluoro group and a sulfonyl group, which is added dispersedly in said polymer composition without intermediary of a medium consisting of a low-molecular-weight polyether-containing compound or low-molecular-weight polar compound whose number-average molecular weight is not more than 5000.

2. The polymeric antistatic agent according to claim 1, wherein said anion-containing salt having said fluoro group and said sulfonyl group is a salt having at least one kind of an anion selected from chemical formulas 1 and 3 shown below:

chemical formula 1

chemical formula 3 where $X_1$, $X_2$, and $X_3$ denote functional groups containing C, —F, and —$SO_2$— and having one to eight carbon atoms.

3. The polymeric antistatic agent according to claim 1, wherein not less than 0.01 parts by weight nor more than 20 parts by weight of said anion-containing salt having said fluoro group and said sulfonyl group is added to total 100 parts by weight of an entire thermoplastic resin or/and an entire elastomer of said polymer composition.

4. The polymeric antistatic agent according to claim 1, wherein said polymer composition contains at least one kind of a copolymer selected from among a group of a polyether block polyolefin copolymer or a polyoxyalkylene copolymer.

5. The polymeric antistatic agent according to claim 2, wherein said anion-containing salt consists of a salt having at least one kind of an anion selected from among a group of a bis (fluoroalkylsulfonyl) imide ion, a fluoroalkylsulfonic acid ion, and a tris (fluoroalkylsulfonyl) methide ion.

6. The polymeric antistatic agent according to claim 1, wherein said anion-containing salt is a salt having a cation of any one of alkali metals, group 2A metals, transition metals, and amphoteric metals and an anion having a fluoro group and a sulfonyl group.

7. The polymeric antistatic agent according to claim 5, wherein said anion-containing salt is a salt selected from among a group of an alkali metal salt of bis (trifluoromethanesulfonyl) imide, an alkali metal salt of tris (trifluoromethanesulfonyl) methide, and an alkali metal salt of trifluoromethanesulfonic acid.

8. The polymeric antistatic agent according to claim 1, containing a polymer having a cyano group at not less than 20 parts by weight of an entire polymer component of said polymeric antistatic agent.

9. An antistatic polymer composition containing not less than 0.1 parts by weight nor more than 65 parts by weight of a polymeric antistatic agent, added to total 100 parts by weight of said one or more kinds of polymers selected from among a group of a thermoplastic polymer, a thermoplastic elastomer, and an unvulcanized rubber, wherein said polymeric antistatic agent comprises a polymer composition containing a polymeric charge prevention agent containing a resin or/and an elastomer as a main component thereof; or/and a thermoplastic resin having a polar group or/and an elastomer having said polar group; and an anion-containing salt, having at least one kind of an anion selected from chemical formulas 1 and 3 shown below, which is added dispersedly in said polymer composition without intermediary of a medium consisting of a low-molecular-weight polyether-containing compound or low-molecular-weight polar compound whose number-average molecular weight is not more than 5000,

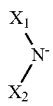

chemical formula 1

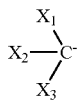

chemical formula 3 where $X_1$, $X_2$, and $X_3$ denote functional groups containing C, —F, and —$SO_2$— and having one to eight carbon atoms, wherein said polymer composition contains a polyether block polyolefin copolymer.

10. The antistatic polymer composition according to claim 9, containing a polymer having a cyano group at not less than 20 parts by weight of an entire polymer component of said antistatic polymer composition.

11. The antistatic polymer composition according to claim 10, wherein said polymer having said cyano group is of a low-nitrile type in which a central value of a content of acrylonitrile is not more than 24 wt %.

12. The antistatic polymer composition according to claim 10, wherein said anion-containing salt is mixed with said polymer having said cyano group to form a master batch.

13. The antistatic polymer composition according to claim 12, wherein a content of said anion-containing salt contained in said master batch is not less than one wt % nor more than 40 wt %.

14. The antistatic polymer composition according to claim 9, comprising:
a low-polar polymer composition consisting of any one of an olefin resin, an olefin thermoplastic elastomer, and a styrene thermoplastic elastomer or a mixture of said olefin resin, said olefin thermoplastic elastomer, and said styrene thermoplastic elastomer; and
a polymer having an ester structure.

15. The antistatic polymer composition according to claim 14, containing not less than one part by weight nor more than 40 parts by weight of said polymer having said ester structure and not less than 0.01 nor more than 20 parts by weight of said anion-containing salt specified by said chemical formulas 1 and 3 for 100 parts by weight of said low-polar polymer composition.

16. The antistatic polymer composition according to claim 14, wherein said olefin resin consists of polypropylene or polyethylene;
said olefin thermoplastic elastomer consists of rubber and polyolefin in which said rubber dynamically crosslinked with a crosslinking agent is dispersed; and
said styrene thermoplastic elastomer consists of rubber and styrene thermoplastic elastomer in which said rubber dynamically crosslinked with a crosslinking agent is dispersed.

17. The antistatic polymer composition according to claim 14, containing said salt with intermediary of polyether block polyolefin.

18. The antistatic polymer composition according to claim 9, having a permanent compression set not more than 30% when said permanent compression set is measured at a temperature of 70° C. for 22 to 24 hours at a permanent compression rate of 25% in accordance with Permanent set testing methods for rubber, vulcanized or thermoplastic specified in JIS K6262; and a volume resistivity not more than $10^{11.0}(\Omega \cdot cm)$ or/and a surface resistivity not more than $10^{11.0}(\Omega)$, when said volume resistivity or/and said surface resistivity are measured at a temperature of 23° C. and a relative humidity of 55% with a voltage of 1000 applied thereto in accordance with the method specified in JIS K6911.

19. An antistatic polymer composition containing not less than 0.1 parts by weight nor more than 65 parts by weight of a polymeric antistatic agent added to total 100 parts by weight of so one or more kinds of polymers selected from among a group of a thermoplastic polymer, a thermoplastic elastomer, and an unvulcanized rubber, wherein a crosslinkable rubber or/and a thermoplastic elastomer are dispersed by dynamic crosslinking, and said polymeric antistatic agent comprises a polymer composition containing a polymeric charge prevention agent containing a resin or/and an elastomer as a main component thereof; or/and a thermoplastic resin having a polar group or/and an elastomer having said polar group; and an anion-containing salt, having a fluoro group and a sulfonyl group, which is added dispersedly in said polymer composition without intermediary of a medium consisting of a low-molecular-weight polyether-containing compound or low-molecular-weight polar compound whose number-average molecular weight is not more than 5000, wherein said polymer composition contains a polyether block polyolefin copolymer.

20. The antistatic polymer composition according to claim 19, wherein a compound (B) containing a rubber component whose main component is EPDM is dispersed by dynamic crosslinking in a compound (A) containing a styrene thermoplastic elastomer as a main component thereof.

21. The antistatic polymer composition according to claim 20, wherein said compound (A) contains not less than 15 parts by weight nor more than 500 parts by weight of a softener and not less than one part by weight nor more than 50 parts by weight of a resin containing an olefin resin as a main component thereof for 100 parts by weight of said rubber component; and said compound (B) contains not less than 15 parts by weight nor more than 600 parts by weight of a softener for 100 parts by weight of said rubber component.

22. A polymeric antistatic agent containing a polymer having a cyano group at not less than 20 parts by weight of an entire polymer component of said polymeric antistatic agent, wherein said polymeric antistatic agent comprises a polymer composition containing a polymeric charge prevention agent containing a resin or/and an elastomer as a main component thereof; or/and a thermoplastic resin having a polar group or/and an elastomer having said polar group; and an anion-containing salt, having a fluoro group and a sulfonyl group, which is added dispersedly in said polymer composition without intermediary of a medium consisting of a low-molecular-weight polyether-containing compound or low-molecular-weight polar compound whose number-average molecular weight is not more than 5000, wherein said polymer composition contains a polyether block polyolefin copolymer.

23. The polymeric antistatic agent according to claim 22, wherein said polymer having said cyano group consists of one or more rubbers selected among a group of acrylonitrile butadiene rubber, hydrogenated acrylonitrile butadiene rubber, carboxylic acrylonitrile butadiene rubber, acrylonitrile butadiene-isoprene rubber (NBIR), liquid nitrile rubber, and latices of said rubbers.

24. The polymeric antistatic agent according to claim 22, wherein said anion-containing salt is mixed with said polymer having said cyano group to form a master batch.

* * * * *